US008591944B2

(12) United States Patent  
Padval et al.

(10) Patent No.: US 8,591,944 B2
(45) Date of Patent: Nov. 26, 2013

(54) SOLID DISPERSION FORMULATIONS AND METHODS OF USE THEREOF

(75) Inventors: Mahesh V. Padval, Needham, MA (US); Jeff T. Gautschi, Bend, OR (US); Daniel T. Smithey, Bend, OR (US); Marshall D. Crew, Bend, OR (US); Abizer Harianawala, Acton, MA (US)

(73) Assignee: Zalicus Pharmaceuticals Ltd., Vancouver (CA)

(*) Notice: Subject to any disclaimer, the term of this patent is extended or adjusted under 35 U.S.C. 154(b) by 0 days.

(21) Appl. No.: 13/414,369

(22) Filed: Mar. 7, 2012

(65) Prior Publication Data

US 2013/0035345 A1    Feb. 7, 2013

Related U.S. Application Data

(60) Provisional application No. 61/450,479, filed on Mar. 8, 2011, provisional application No. 61/485,405, filed on May 12, 2011.

(51) Int. Cl.  
*A61K 9/10* (2006.01)

(52) U.S. Cl.  
USPC ............................ 424/465; 424/464; 424/484

(58) Field of Classification Search  
None  
See application file for complete search history.

(56) References Cited

U.S. PATENT DOCUMENTS

| | | | |
|---|---|---|---|
| 3,288,795 A | 11/1966 | Irikura et al. | |
| 3,445,464 A | 5/1969 | Jucker et al. | |
| 3,531,480 A | 9/1970 | Jucker et al. | |
| 4,188,485 A | 2/1980 | Kukla | |
| 4,411,904 A | 10/1983 | Pattison | |
| 4,751,230 A | 6/1988 | Lavielle et al. | |
| 4,766,116 A | 8/1988 | Tatsuoka et al. | |
| 4,766,125 A | 8/1988 | Van Daele | |
| 4,782,071 A | 11/1988 | Butler et al. | |
| 4,883,797 A | 11/1989 | Foguet et al. | |
| 4,918,073 A | 4/1990 | Rüger et al. | |
| 5,292,726 A | 3/1994 | Ashton et al. | |
| 5,344,830 A | 9/1994 | Mills et al. | |
| 5,386,025 A | 1/1995 | Jay et al. | |
| 5,391,552 A | 2/1995 | Inazu et al. | |
| 5,428,038 A | 6/1995 | Chatterjee et al. | |
| 5,623,051 A | 4/1997 | Catterall et al. | |
| 5,624,677 A * | 4/1997 | El-Rashidy et al. | .......... 424/435 |
| 5,646,149 A | 7/1997 | Hellberg et al. | |
| 5,703,071 A | 12/1997 | Itoh et al. | |
| 5,866,574 A | 2/1999 | Okamura et al. | |
| 6,011,035 A | 1/2000 | Snutch et al. | |

(Continued)

FOREIGN PATENT DOCUMENTS

EP    0344603 A1    12/1989

OTHER PUBLICATIONS

U.S. Appl. No. 13/414,390, filed Mar. 7, 2012, Padval et al.  
U.S. Appl. No. 13/494,545, filed Jun. 12, 2012, Padval et al.

(Continued)

*Primary Examiner* — Anand Desai  
*Assistant Examiner* — Melissa Mercier  
(74) *Attorney, Agent, or Firm* — Clark & Elbing LLP

(57) ABSTRACT

The present invention relates to formulations and methods for increasing the bioavailability of 1-(4-benzhydrylpiperazin-1-yl)-3,3-diphenylpropan-1-one, 1-(3,3-diphenylpropanoyl) piperazine, or a salt thereof. In particular, the formulation can include one or more pharmaceutically acceptable matrix polymers to form a solid dispersion, e.g., a spray dried dispersion or a hot melt extrusion.

29 Claims, 13 Drawing Sheets

(56) References Cited

U.S. PATENT DOCUMENTS

| | | | |
|---|---|---|---|
| 6,090,631 A | 7/2000 | Catterall et al. |
| 6,218,538 B1 | 4/2001 | Downs et al. |
| 6,251,918 B1 | 6/2001 | Hu et al. |
| 6,267,945 B1 | 7/2001 | Zamponi |
| 6,294,533 B1 | 9/2001 | Snutch et al. |
| 6,310,058 B1 | 10/2001 | Miller et al. |
| 6,310,059 B1 | 10/2001 | Snutch |
| 6,323,243 B1 | 11/2001 | Rafferty et al. |
| 6,362,174 B1 | 3/2002 | Rafferty et al. |
| 6,387,897 B1 | 5/2002 | Snutch |
| 6,458,781 B1 | 10/2002 | Connor et al. |
| 6,492,375 B2 | 12/2002 | Snutch |
| 6,605,608 B1 | 8/2003 | Seko et al. |
| 6,610,717 B2 | 8/2003 | Nakajo et al. |
| 6,617,322 B2 | 9/2003 | Snutch |
| 6,763,607 B2 | 7/2004 | Beyerinck et al. |
| 6,815,447 B2 | 11/2004 | Chaudhari et al. |
| 6,841,680 B2 | 1/2005 | Chapdelaine et al. |
| 6,943,168 B2 | 9/2005 | Snutch et al. |
| 6,949,554 B2 | 9/2005 | Snutch et al. |
| 6,951,860 B2 | 10/2005 | Mehanna et al. |
| 6,951,862 B2 | 10/2005 | Snutch et al. |
| 6,973,741 B2 | 12/2005 | Beyerinck et al. |
| 7,064,128 B2 | 6/2006 | Snutch et al. |
| 7,115,279 B2 | 10/2006 | Curatolo et al. |
| 7,186,726 B2 | 3/2007 | Snutch et al. |
| 7,235,259 B2 | 6/2007 | Crew et al. |
| 7,666,865 B2 | 2/2010 | Snutch et al. |
| 7,887,840 B2 | 2/2011 | Curatolo et al. |
| 8,026,286 B2 | 9/2011 | Curatolo et al. |
| 8,048,452 B2 | 11/2011 | Curatolo et al. |
| 8,197,848 B2 | 6/2012 | Crew et al. |
| 8,202,912 B2 | 6/2012 | Curatolo et al. |
| 8,207,232 B2 | 6/2012 | Babcock et al. |
| 8,236,328 B2 | 8/2012 | Babcock et al. |
| 8,257,739 B2 | 9/2012 | Babcock et al. |
| 8,257,741 B2 | 9/2012 | Curatolo et al. |
| 8,263,128 B2 | 9/2012 | Curatolo et al. |
| 8,337,899 B2 | 12/2012 | Curatolo et al. |
| 8,343,550 B2 | 1/2013 | Beyerinck et al. |
| 8,409,560 B2 | 4/2013 | Padval et al. |
| 2001/0029258 A1 | 10/2001 | Snutch |
| 2003/0045530 A1 | 3/2003 | Snutch |
| 2003/0104063 A1 | 6/2003 | Babcock et al. |
| 2003/0199523 A1 | 10/2003 | Snutch |
| 2003/0219489 A1 | 11/2003 | Curatolo et al. |
| 2003/0228358 A1 | 12/2003 | Perlman et al. |
| 2004/0005359 A1 | 1/2004 | Cheng et al. |
| 2004/0034035 A1 | 2/2004 | Snutch et al. |
| 2004/0044004 A1 | 3/2004 | Snutch et al. |
| 2004/0147529 A1 | 7/2004 | Snutch et al. |
| 2004/0180323 A1 | 9/2004 | Belardetti et al. |
| 2004/0192703 A1 | 9/2004 | Snutch et al. |
| 2004/0194338 A1 | 10/2004 | Beyerinck et al. |
| 2004/0204404 A1 | 10/2004 | Zelle et al. |
| 2004/0209872 A1 | 10/2004 | Snutch et al. |
| 2004/0259866 A1 | 12/2004 | Snutch et al. |
| 2004/0266784 A1 | 12/2004 | Snutch et al. |
| 2005/0014748 A1 | 1/2005 | Pajouhesh et al. |
| 2005/0123602 A1 | 6/2005 | Michaelis |
| 2005/0227999 A1 | 10/2005 | Pajouhesh et al. |
| 2006/0084660 A1 | 4/2006 | Snutch et al. |
| 2006/0089385 A1 | 4/2006 | Cui et al. |
| 2007/0248668 A1 | 10/2007 | Michaelis et al. |
| 2008/0227823 A1 | 9/2008 | Pajouhesh et al. |
| 2008/0280900 A1 | 11/2008 | Pajouhesh et al. |
| 2008/0300262 A1* | 12/2008 | Snutch .................. 514/255.04 |
| 2009/0012010 A1 | 1/2009 | Galemmo, Jr. et al. |
| 2009/0221603 A1 | 9/2009 | Pajouhesh et al. |
| 2009/0270338 A1 | 10/2009 | Galemmo, Jr. et al. |
| 2009/0270394 A1 | 10/2009 | Galemmo, Jr. et al. |
| 2009/0270413 A1 | 10/2009 | Galemmo, Jr. et al. |
| 2009/0286806 A1 | 11/2009 | Pajouhesh et al. |
| 2009/0298834 A1 | 12/2009 | Pajouhesh et al. |
| 2009/0298883 A1 | 12/2009 | Pajouhesh et al. |
| 2009/0312346 A1 | 12/2009 | Snutch et al. |
| 2010/0003331 A1 | 1/2010 | Ahmed et al. |
| 2010/0029681 A1 | 2/2010 | Pajouhesh et al. |
| 2010/0105682 A1 | 4/2010 | Pajouhesh et al. |
| 2010/0168103 A1 | 7/2010 | Pajouhesh et al. |
| 2012/0252819 A1 | 10/2012 | Padval et al. |
| 2012/0259022 A1 | 10/2012 | Curatolo et al. |
| 2012/0277315 A1 | 11/2012 | Crew et al. |
| 2012/0292797 A1 | 11/2012 | Curatolo et al. |
| 2012/0295988 A1 | 11/2012 | Babcock et al. |
| 2012/0322805 A1 | 12/2012 | Babcock et al. |
| 2012/0328679 A1 | 12/2012 | Curatolo et al. |

OTHER PUBLICATIONS

International Search Report and Written Opinion of the International Searching Authority issued in International Application No. PCT/US12/28088, dated Jun. 25, 2012 (11 pages).

Woo et al., "Reduced food-effect and enhanced bioavailability of a self-microemulsifying formulation of itraconazole in healthy volunteers," *Eur. J. Pharm. Sci.* 33: 159-165 (2008).

U.S. Appl. No. 13/661,729, Padval et al.

U.S. Appl. No. 13/727,391, Beyerinck et al.

Ambike et al., "Stability Study of Amorphous Valdecoxib," International Journal of Pharmaceutics, 282: 151-162, 2004.

Calahan, Julie, Thesis: "Characterization of Amorphous Solid Dispersions of AMG 517 in HPMC-AS and Crystallization using Isothermal Microcalorimetry", 2011.

Hong, Liu, Thesis: "Solid Molecular Dispersions of Itraconazole for Enhanced Dissolution and Controlled Drug Delivery," Master of Science, Graduate Department of Pharmaceutical Sciences, University of Toronto, 2009.

Hugo et al., Selection of Excipient, Solvent, and Packaging to Optimize the Performance of Spray-dried Formulations; Case Example Fenofibrate, Drug Development and Industrial Pharmacy pp. 1-11, 2012.

Qian et al., "Drug-polymer Solubility and Miscibility: Stability Consideration and Practical Challenges in Amorphous Solid Dispersion Development," Wiley Journal of Pharmaceutical Sciences 99: 2941-2947, 2010.

Srinarong, Parinda, Thesis: "Improved Dissolution Behavior of Lipophilic Drugs by Solid Dispersions: A Matter of Composition," University of Groningen and the Faculty of Mathematics and Natural Sciences of the University of Groningen, 2011.

* cited by examiner

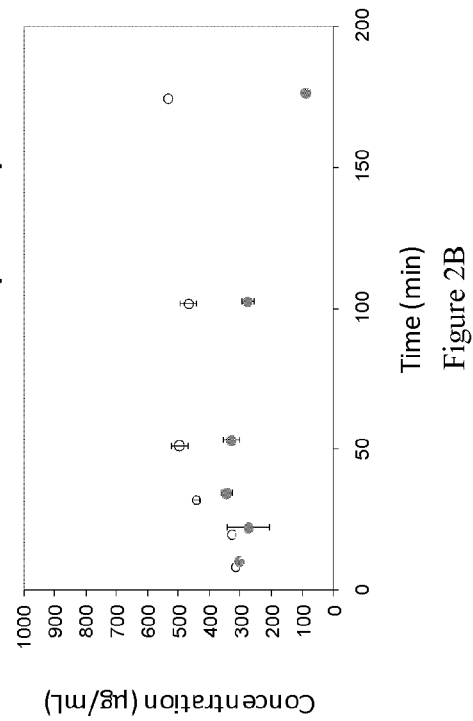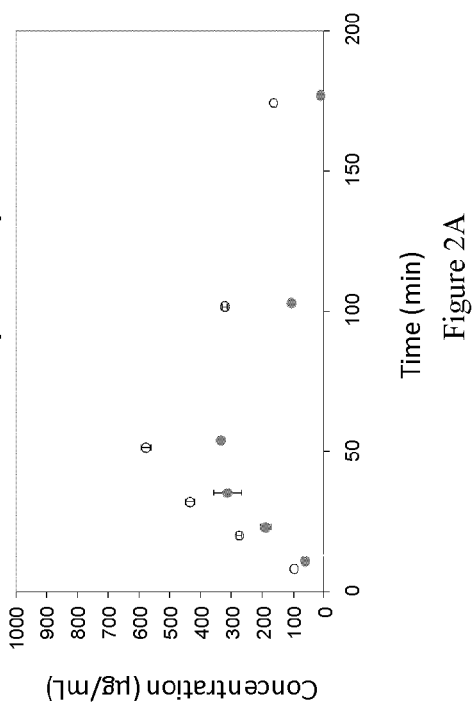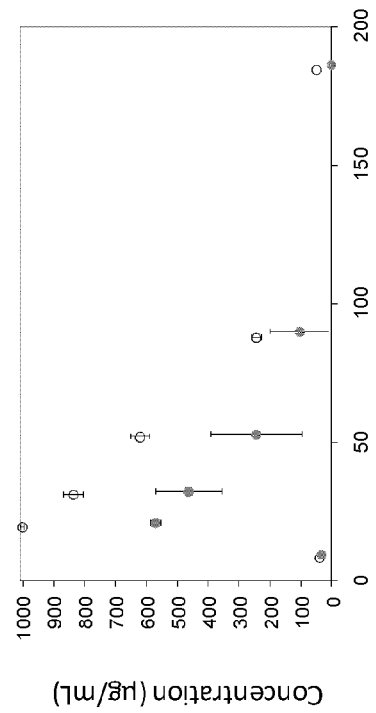
Figure 2A
Figure 2B
Figure 2C

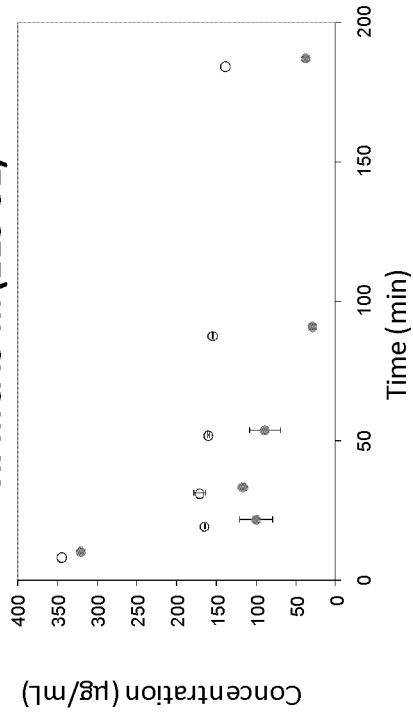
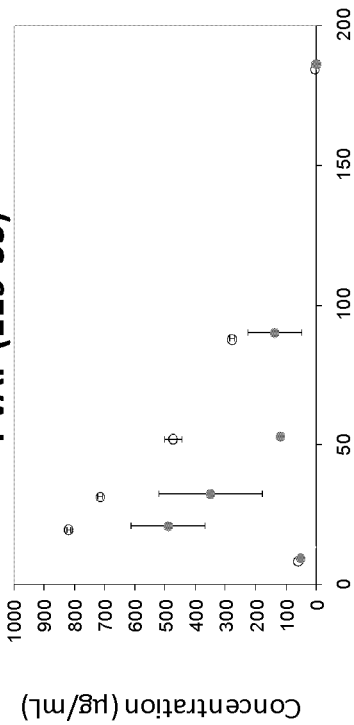
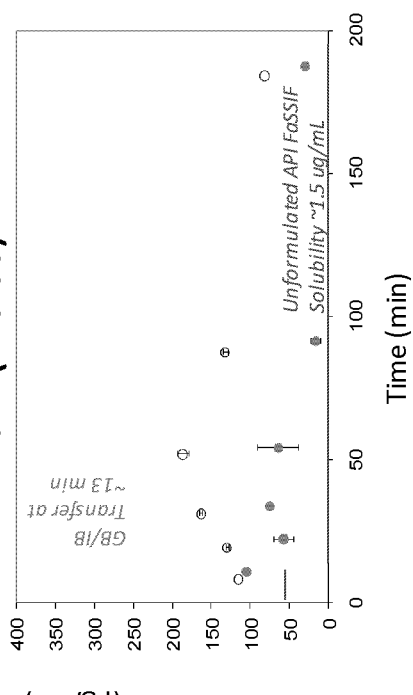
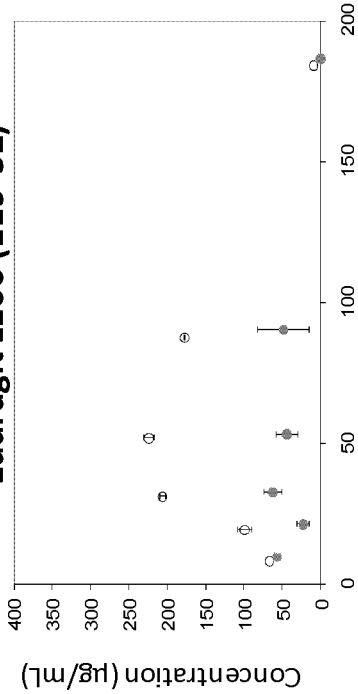

SOLID DISPERSION FORMULATIONS AND METHODS OF USE THEREOF

CROSS REFERENCE TO RELATED APPLICATIONS

This application claims benefit of U.S. Provisional Application No. 61/450,479, filed on Mar. 8, 2011, and U.S. Provisional Application No. 61/485,405, filed on May 12, 2011, each of which is hereby incorporated by reference in its entirety.

BACKGROUND OF THE INVENTION

The present invention relates to formulations and methods for increasing the bioavailability of 1-(4-benzhydrylpiperazin-1-yl)-3,3-diphenylpropan-1-one or a metabolite thereof, as well as salts thereof. In particular, the formulations and methods relate to the use of solid dispersions to improve mean bioavailability in fasted or fed subjects and/or to reduce food effect.

Ion channels mediate a variety of normal physiological functions and are also implicated in a number of human disorders. Examples of human disorders mediated by calcium channels include but are not limited to congenital migraine, cerebellar ataxia, angina, epilepsy, hypertension, ischemia, and some arrhythmias (see, e.g., Janis et al., *Ion Calcium Channels: Their Properties, Functions, Regulation and Clinical Relevance* (1991) CRC Press, London); and those mediated by sodium channels include but are not limited to epilepsy, cancer, pain, migraine, Parkinson's Disease, mood disorders, schizophrenia, psychosis, tinnitus, amyotrophic lateral sclerosis, glaucoma, ischaemia, spasticity disorders, obsessive compulsive disorder, restless leg syndrome, and Tourette syndrome. Modulators of ion channels, e.g., such as 1-(4-benzhydrylpiperazin-1-yl)-3,3-diphenylpropan-1-one, a metabolite thereof, or a salt thereof, are thus desired. In particular, formulations of such modulators having improved oral bioavailability and/or reduced patient-to-patient variability in pharmacokinetic behavior are needed.

SUMMARY OF THE INVENTION

The invention provides formulations and methods for administering 1-(4-benzhydrylpiperazin-1-yl)-3,3-diphenylpropan-1-one (compound 1), a metabolite thereof (e.g., 1-(3,3-diphenylpropanoyl)piperazine (compound 2)), or a salt thereof. Compound 1 is a potent N-type calcium channel antagonist having selectivity over other types of calcium channels (e.g., L-type or P/Q-type calcium channels). The invention also provides use of these formulations for acting at ion channels (e.g., calcium channels (e.g., N-type calcium channels) and/or sodium channels) and for treating various conditions associated with these channels, such as pain and epilepsy.

In a first aspect, the invention relates to a pharmaceutical composition in unit dosage form for oral administration, the composition including from about 20 mg to about 250 mg of substantially amorphous compound 1, compound 2, or a salt thereof, and a pharmaceutically acceptable excipient (e.g., any described herein, such as one or more pharmaceutically acceptable matrix polymers described herein), where, following administration of the pharmaceutical composition to subjects, the ratio of the mean bioavailability for fed subjects to the mean bioavailability for fasted subjects is from about 1.0 to about 2.0.

In a second aspect, the invention relates to a pharmaceutical composition in unit dosage form for oral administration, the composition including from about 20 mg to about 250 mg of substantially amorphous compound 1, compound 2, or a salt thereof, in a pharmaceutically acceptable matrix polymer.

In some embodiments of any of the aspects herein, the percentage loading of compound 1 or compound 2 is of from about 1% to about 30% (w/w) (e.g., from 1% to 5%, from 1% to 10%, from 1% to 15%, from 1% to 20%, from 1% to 25%, from 5% to 10%, from 5% to 15%, from 5% to 20%, from 5% to 25%, from 5% to 30%, from 10% to 15%, from 10% to 20%, from 10% to 25%, from 10% to 30%, from 15% to 20%, from 15% to 25%, from 15% to 30%, from 20% to 25%, from 20% to 30%, and from 25% to 30%).

In some embodiments, following administration of the pharmaceutical composition to subjects (e.g., fed subjects or fasted subjects), the mean bioavailability is greater than about 20% (e.g., greater than 25%, 30%, 35%, 40%, 45%, 50%, 55%, 60%, 65%, 70%, 75%, 80%, 85%, 90%, 95%, or even 99%) or between about 20% to about 90% (e.g., from 20% to 30%, from 20% to 40%, from 20% to 50%, from 20% to 60%, from 20% to 70%, from 20% to 80%, from 20% to 90%, from 30% to 40%, from 30% to 50%, from 30% to 60%, from 30% to 70%, from 30% to 80%, from 30% to 90%, from 40% to 50%, from 40% to 60%, from 40% to 70%, from 40% to 80%, from 40% to 90%, from 50% to 60%, from 50% to 70%, from 50% to 80%, from 50% to 90%, from 60% to 70%, from 60% to 80%, from 60% to 90%, from 70% to 80%, from 70% to 90%, and from 80% to 90%).

In some embodiments, the ratio of the mean bioavailability for fed subjects to the mean bioavailability for fasted subjects is from about 1.0 to about 2.0 (e.g., from 1.0 to 1.1, from 1.0 to 1.2, from 1.0 to 1.3, from 1.0 to 1.4, from 1.0 to 1.5, from 1.0 to 1.6, from 1.0 to 1.7, from 1.0 to 1.8, from 1.0 to 1.9, from 1.3 to 1.4, from 1.3 to 1.5, from 1.3 to 1.6, from 1.3 to 1.7, from 1.3 to 1.8, from 1.3 to 1.9, from 1.3 to 2.0, from 1.5 to 1.6, from 1.5 to 1.7, from 1.5 to 1.8, from 1.5 to 1.9, from 1.5 to 2.0, from 1.7 to 1.8, from 1.7 to 1.9, from 1.7 to 2.0, from 1.8 to 1.9, and from 1.8 to 2.0).

In some embodiments, administration of the pharmaceutical composition to fed and fasted subjects produces a coefficient of variation in $C_{max}$ and/or $AUC_\infty$ of less than about 60% (e.g., less than 55%, 50%, 45%, 40%, 35%, 30%, 25%, 20%, and 15%). In particular embodiments, the coefficient of variation in $C_{max}$ and/or $AUC_\infty$ is of from about 20% to about 60% (e.g., from 20% to 30%, from 20% to 35%, from 20% to 40%, from 20% to 45%, from 20% to 50%, from 20% to 55%, from 30% to 35%, from 30% to 40%, from 30% to 45%, from 30% to 50%, from 30% to 55%, from 30% to 60%, from 35% to 40%, from 35% to 45%, from 35% to 50%, from 35% to 55%, from 35% to 60%, from 40% to 45%, from 40% to 50%, from 40% to 55%, from 40% to 60%, from 45% to 50%, from 45% to 55%, from 45% to 60%, from 50% to 55%, from 50% to 60%, and from 55% to 60%).

In some embodiments, administration of the pharmaceutical composition to fasted or fed subjects produces a coefficient of variation in $C_{max}$ and/or $AUC_\infty$ of less than about 65% (e.g., less than 60%, 55%, 50%, 45%, 40%, 35%, 30%, 25%, 20%, and 15%). In some embodiments, administration of the pharmaceutical composition to fasted or fed subjects produces a coefficient of variation in $C_{max}$ and/or $AUC_\infty$ of from about 30% to about 65% (e.g., from 30% to 35%, from 30% to 40%, from 30% to 45%, from 30% to 50%, from 30% to 55%, from 30% to 60%, from 30% to 65%, from 35% to 40%, from 35% to 45%, from 35% to 50%, from 35% to 55%, from 35% to 60%, from 35% to 65%, from 40% to 45%, from 40% to 50%, from 40% to 55%, from 40% to 60%, from 45% to 50%, from 45% to 55%, from 45% to 60%, from 45% to 65%, from 50% to 55%, from 50% to 60%, from 50% to 65%, from 55% to 60%, from 55% to 65%, and from 60% to 65%).

In some embodiments, administration of the pharmaceutical composition to a fasted subject produces a $C_{max}$ that is greater than about 400 ng/mL (e.g., greater than about 450, 500, 550, 600, 650, 700, 750, or 800 ng/mL and/or up to about 900, 1,000, or 1,500 ng/mL, e.g., from 400 ng/mL to 1,500 ng/mL, from 400 ng/mL to 1,000 ng/mL, from 400 ng/mL to 800 ng/mL, from 400 ng/mL to 700 ng/mL, from 500 ng/mL to 1,500 ng/mL, from 500 ng/mL to 1,000 ng/mL, from 500 ng/mL to 800 ng/mL, and from 500 ng/mL to 700 ng/mL) and/or an $AUC_\infty$ that is greater than about 4,000 hr*ng/mL (e.g., greater than 4,500, 5,000, 5,500, 6,000, 6,500, 7,000, 7,500, or 8,000 hr*ng/mL and/or up to 8,000 hr*ng/mL, e.g., from 4,000 hr*ng/mL to 8,000 hr*ng/mL, from 4,500 hr*ng/mL to 8,000 hr*ng/mL, from 5,000 hr*ng/mL to 8,000 hr*ng/mL, from 4,000 hr*ng/mL to 7,000 hr*ng/mL, from 4,500 hr*ng/mL to 7,000 hr*ng/mL, and from 5,000 hr*ng/mL to 7,000 hr*ng/mL) for a 225 mg dose of compound 1 or compound 2.

In any of the above aspects, the pharmaceutical composition includes a solid dispersion of the compound 1, compound 2, or the salt thereof, and a pharmaceutically acceptable matrix polymer, where the weight ratio of the compound 1, compound 2, or the salt thereof, to the pharmaceutically acceptable matrix polymer is from about 1:6 to about 1:1.5 (e.g., from 1:6 to 1:2, from 1:6 to 1:2.5, from 1:6 to 1:3, from 1:6 to 1:3.5, from 1:6 to 1:4, from 1:6 to 1:4.5, from 1:6 to 1:5, from 1:5 to 1:2, from 1:5 to 1:2.5, from 1:5 to 1:3, from 1:5 to 1:3.5, from 1:5 to 1:4, from 1:5 to 1:4.5, from 1:5 to 1:1.5, from 1:4 to 1:1.5, from 1:4 to 1:2, from 1:4 to 1:2.5, from 1:4 to 1:3, from 1:4 to 1:3.5, from 1:3 to 1:1.5, from 1:3 to 1:2, from 1:3 to 1:2.5, and from 1:2 to 1:1.5).

In some embodiments, at least about 90% (e.g., at least 95%, 96%, 97%, 98%, 99%, 99.5%, or even 99.9%, such as from 90% to 99.9%, from 90% to 99.5%, from 90% to 99%, from 90% to 98%, from 90% to 97%, from 90% to 96%, from 90% to 95%, from 95% to 99.9%, from 95% to 99.5%, from 95% to 99%, from 95% to 98%, from 95% to 97%, and from 95% to 96%) of the compound 1, compound 2, or the salt thereof, is in amorphous form.

In some embodiments, the pharmaceutically acceptable matrix polymer includes a polymer selected from a cellulose derivative, a polyacrylate, a polyvinyl pyrrolidone, a polyvinyl acetate, or a copolymer of a polyvinyl pyrrolidone and a polyvinyl acetate.

In further embodiments, the cellulose derivative is a cellulose acetate having from about 10% to about 50% (e.g., from 10% to 15%, from 10% to 20%, from 10% to 25%, from 10% to 30%, from 10% to 35%, from 10% to 40%, from 10% to 45%, from 20% to 25%, from 20% to 30%, from 20% to 35%, from 20% to 40%, from 20% to 45%, from 20% to 50%, from 25% to 30%, from 25% to 35%, from 25% to 40%, from 25% to 45%, from 25% to 50%, from 30% to 35%, from 30% to 40%, from 30% to 45%, from 30% to 50%, from 35% to 40%, from 35% to 45%, from 35% to 50%, from 40% to 45%, and from 40% to 50%) acetyl. In further embodiments, the cellulose acetate is cellulose acetate phthalate (CAP) (e.g., having about 35% phthalyl/24% acetyl), methylcellulose acetate phthalate, hydroxypropylmethyl cellulose acetate, and hydroxypropylmethyl cellulose acetate succinate (HPMCAS) (e.g., having about 9% acetyl/11% succinoyl, 12% acetyl/6% succinoyl, and 8% acetyl/15% succinoyl).

In some embodiments, the mean particle size of the matrix polymer is about 1 mm or about 5 µm. In particular embodiments, the matrix polymer is HPMCAS having a mean particle size of about 1 mm (e.g., grade MG) or about 5 µm (e.g., grade MF).

In other embodiments, the cellulose derivative is selected from an alkyl cellulose (e.g., methyl cellulose and ethyl cellulose), a hydroxyalkyl cellulose (e.g., hydroxymethyl cellulose, hydroxyethyl cellulose, hydroxypropyl cellulose, such as those having 11% hydroxypropyl or 8% hydroxypropyl, and hydroxybutyl cellulose), a hydroxyalkylalkyl cellulose (e.g., hydroxyethylmethyl cellulose and hydroxypropylmethyl cellulose (HPMC) having 19-24% methoxyl/7-12% hydroxypropxyl, 28-30% methoxyl/7-12% hydroxypropxyl, 23% methoxyl/10% hydroxypropxyl, 23%-29% methoxyl/8%-9% hydroxypropxyl, 29% methoxyl/9% hydroxypropxyl, and 23% methoxyl/6% hydroxypropxyl), a hydroxyalkylalkyl cellulose ester (e.g., hydroxypropylmethyl cellulose phthalate (HPMCP)), a carboxyalkyl cellulose (e.g., carboxymethyl cellulose and alkali metal salts thereof, such as sodium salts), a carboxyalkylalkyl cellulose (e.g., carboxymethylethyl cellulose), and a carboxyalkyl cellulose ester (e.g., carboxymethyl cellulose butyrate, carboxymethyl cellulose propionate, carboxymethyl cellulose acetate butyrate, and carboxymethyl cellulose acetate propionate). In further embodiment, the cellulose derivative is further cross-linked or copolymerized (e.g., with any matrix polymer described herein).

In some embodiments, the matrix polymer is the polyacrylate selected from a polymethacrylate, a methacrylate copolymer (e.g., a methacrylic acid-methyl methacrylate copolymer having a 1:1 ratio of free carboxyl groups to ester groups and a 1:2 ratio of free carboxyl groups to ester groups, a dimethylaminoethyl methacrylate-butyl methacrylate-methyl methacrylate copolymer, and a diethylaminoethyl methacrylic acid-methyl methacrylate copolymer), and an ethacrylate copolymer (e.g., a methacrylic acid ethacrylate copolymer having a 50:50 ratio of methacrylic acid to ethacrylate).

In some embodiments, the matrix polymer is the polyvinyl acetate selected from a polyvinyl pyrrolidone (e.g., povidone) having a molecular weight more than about 2,000 (e.g., about 2,500, about 9,000, about 50,000, and about 1,250,000), a polyvinyl acetate ester (e.g., polyvinyl acetate phthalate (PVAP)), and a polyethylene glycol polyvinylacetate copolymer (e.g., polyethylene glycol-polyvinylcaprolactam-polyvinylacetate copolymer).

In other embodiments, the matrix polymer is the copolymer of a polyvinyl pyrrolidone and a polyvinyl acetate and the copolymer has from about 10:90 to about 70:30 ratio (e.g., 20:80, 30:70, 40:60, 50:50, and 60:40) of N-vinyl-2-pyrrolidone to vinyl acetate.

In some embodiments, the pharmaceutical composition further includes a plasticizer. Exemplary plasticizers include those selected from a polyalkylene oxide (e.g., polyethylene glycols, such as PEG 300, PEG 400, PEG 4000, and PEG 8000, and polypropylene glycols), a copolymer of ethylene oxide and propylene oxide (e.g., ethoxylated propoxylated block copolymers having the formula $H(OCH_2CH_2)_a(OCHCH_3CH_2)_b(OCH_2CH_2)_aOH$, where a is between 10 and 150 and b is between 10 and 100 (e.g., where a is about 12 and b is about 20, a is about 38 and b is about 29, a is about 80 and b is about 27, a is about 64 and b is about 37, a is about 141 and b is about 44, a is about 49 and b is about 57, and a is about 101 and b is about 56), and a polyethoxylated glyceryl ester (e.g., polyoxyl 35 castor oil and polyoxyl 40 castor oil having 40-45 moles of ethylene oxide).

In some embodiments, the composition further includes a surfactant. Exemplary surfactants include those selected from a polyethoxylated ester of one or more fatty acids, a polyethoxylated alkyl ether, a polyethoxylated glyceryl ester, a polyoxyethylene glyceryl ester of one or more fatty acids, a sorbitan ester, a polyethoxylated sorbitan ester, a polyethoxylated vitamin analog (e.g., a pegylated vitamin E compound, e.g., D-alpha-tocopheryl PEG 1000 succinate), and an ethoxylated propoxylated block copolymer.

In other embodiments, the solid dispersion is formed by spray drying a liquid mixture including compound 1, compound 2, or the salt thereof, and the pharmaceutically acceptable matrix polymer. In some embodiments, the matrix polymer is a cellulose derivative (e.g., any described herein).

In some embodiments, the solid dispersion is formed by hot melt extrusion of a mixture including compound 1, compound 2, or the salt thereof, and the pharmaceutically acceptable matrix polymer. In some embodiments, the matrix polymer is a cellulose derivative (e.g., hydroxypropylmethyl cellulose (HPMC), hydroxypropylmethyl cellulose phthalate (HPMCP), cellulose acetate phthalate (CAP), hydroxypropylmethyl cellulose acetate succinate (HPMCAS), or any described herein), a polyacrylate (e.g., a polymethacrylate, a methacrylate copolymer, or any described herein, e.g., a methacrylic acid-methyl methacrylate copolymer (e.g., Eudragit® L 100 or Eudragit® S 100, MW ~125,000 g/mol), a dimethylaminoethyl methacrylate-butyl methacrylate-methyl methacrylate copolymer (e.g., Eudragit® E PO, Eudragit® E 100, or Eudragit® E 12.5, respectively), a diethylaminoethyl methacrylic acid-methyl methacrylate copolymer (e.g., Eudragit® E), or an ethacrylate copolymer, such as a methacrylic acid ethacrylate copolymer (e.g., Kollicoat® MAE 100P or Eudragit®L 100-55), a polyvinyl pyrrolidone, a polyvinyl acetate, or a copolymer of a polyvinyl pyrrolidone and a polyvinyl acetate.

In a third aspect, the invention features a method for reducing the food effect exhibited by compound 1, compound 2, or a salt thereof, following administration to a subject, the method including administering a unit dosage form including any pharmaceutical composition described herein to the subject.

In a fourth aspect, the invention features a method to treat a disease or condition (e.g., pain, epilepsy, or any described herein), the method including administering to a subject (e.g., a fasted subject or a fed subject) in need of such treatment an effective amount of any pharmaceutical composition described herein.

In a fifth aspect, the invention features a method to treat a disease or condition (e.g., pain, epilepsy, or any described herein) modulated by ion channel activity, the method including administering to a subject (e.g., a fasted subject or a fed subject) in need of such treatment an effective amount of any pharmaceutical composition described herein.

In a sixth aspect, the invention features a method of inhibiting an ion channel, the method including contacting a cell (e.g., a cell from a fasted subject or a cell from a fed subject) with any pharmaceutical composition described herein (e.g., an effective amount of any pharmaceutical composition described herein).

In some embodiments of the above aspects, the ion channel is a calcium channel or a sodium channel. In some embodiments, the calcium channel is an N-type calcium channel (e.g., the $Ca_V2.2$ channel). In some embodiments, the sodium channel is a voltage-gated sodium channel (e.g., the $Na_V1.7$ channel or the $Na_V1.8$, channel).

In some embodiments, the condition is pain, epilepsy, Parkinson's disease, a mood disorder (e.g., a major depressive disorder (e.g., atypical depression, melancholic depression, psychotic major depression, catatonic depression, postpartum depression, seasonal affective disorder, dysthymia, and depressive disorder not otherwise specified (DD-NOS)), recurrent brief depression, minor depressive disorder, or a bipolar disorder), psychosis (e.g., schizophrenia), tinnitus, amyotrophic lateral sclerosis, glaucoma, ischaemia, a spasticity disorder, obsessive compulsive disorder, restless leg syndrome, or Tourette syndrome. In particular embodiments, the condition is pain or epilepsy.

In some embodiments, the pain is inflammatory pain (e.g., caused by rheumatoid arthritis, juvenile idiopathic arthritis, ankylosing spondylitis, psoriatic arthritis, inflammatory bowel disease, primary dysmenorrhea, or endometriosis) or neuropathic pain. In other embodiments, the pain is chronic pain. In further embodiments, the chronic pain is peripheral neuropathic pain (e.g., post-herpetic neuralgia, diabetic neuropathic pain, neuropathic cancer pain, HIV-associated neuropathy, erythromelalgia, failed back-surgery syndrome, trigeminal neuralgia, or phantom limb pain), central neuropathic pain (e.g., multiple sclerosis related pain, Parkinson disease related pain, post-stroke pain, post-traumatic spinal cord injury pain, lumbosacral radiculopathy, cervical radiculopathy, brachial radiculopathy, or pain in dementia), musculoskeletal pain (e.g., osteoarthritic pain or fibromyalgia syndrome), headache (e.g., migraine, cluster headache, tension headache syndrome, facial pain, or headache caused by other diseases), visceral pain (e.g., interstitial cystitis, irritable bowel syndrome, or chronic pelvic pain syndrome), or mixed pain (e.g., lower back pain, neck and shoulder pain, burning mouth syndrome, or complex regional pain syndrome). In still other embodiments, the pain is acute pain. In further embodiments, the acute pain is nociceptive pain or post-operative pain.

In a seventh aspect, the invention features a method of preparing any pharmaceutical composition described herein, the method including preparing a mixture (e.g., a liquid mixture) or a solution including compound 1, compound 2, or a salt thereof, and a pharmaceutically acceptable matrix polymer; and spray drying the mixture or the solution to form a solid dispersion (e.g., a spray dried dispersion).

In an eighth aspect, the invention features a method of preparing any pharmaceutical composition described herein, the method including preparing a mixture or a solution including compound 1, compound 2, or a salt thereof, and a pharmaceutically acceptable matrix polymer; heating (e.g., up to or above the transition glass temperature or melting temperature of the matrix polymer) the mixture to form a homogenous molten mass; extruding the molten mass; and cooling the molten mass to form a solid dispersion (e.g., a hot melt extrusion).

In some embodiments of the seventh and eighth aspects, the mixture or the solution further includes a solvent (e.g., one or more of dimethyl acetamide, dimethyl formamide, pyrrolidone, methylpyrrolidone, methanol, ethanol, and acetone).

In some embodiments, the mixture or the solution further includes a pharmaceutically acceptable excipient (e.g., butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol). Further exemplary excipients include an inert diluent or filler (e.g., sucrose, sorbitol, sugar, mannitol, microcrystalline cellulose, a starch including potato starch, kaolin, calcium carbonate, sodium chloride, lactose, such as lactose monohydrate, calcium phosphate, calcium sulfate, and sodium phosphate); a granulating agent or a disintegrating agent (disintegrant) (e.g., a cellulose derivative including microcrystalline cellulose, a starch including potato starch and sodium starch glycolate, croscarmellose sodium, alginate, and alginic acid); a binding agent (e.g., sucrose, glucose, sorbitol, acacia, alginic acid, sodium alginate, gelatin, starch, pregelatinized starch, microcrystalline cellulose, lactose, such as lactose monohydrate, magnesium aluminum silicate, carboxymethylcellulose sodium, methylcellulose, hydroxypropyl methylcellulose, ethylcellulose, polyvinylpyrrolidone, and polyethylene glycol); a lubricant (e.g., magnesium stearate, calcium stearate, zinc stearate, sodium stearyl fumurate, sodium lauryl sulfate, stearic acid, hydrogenated vegetable oil, mineral oil, PEG 4000-6000, sodium benzoate, glyceryl palmitostearate, glyceryl behenate, and talc); a wetting agent or a surfactant (e.g., sodium lauryl sulfate, polysorbate 80, and a pegylated vitamin E compound, as described herein); a glidant (e.g., magnesium stearate, calcium stearate, zinc stearate, colloidal silicon dioxide, magnesium carbonate, silica, such as fumed silica, and talc); an antiadhesive (e.g., magnesium stearate, calcium stearate, zinc stearate, fumed silica, and talc); a colorant; a flavoring agent; a plasticizer; a humectant; a buffering agent; an antioxidant; a coating or a film former; a compression aid; an emollient; an emulsifier; a fragrance; a preservative; a printing ink; a sorbent; a suspending or dispersing agent; a sweetener; and waters of hydration.

In some embodiments, the composition includes of from about 1% to about 30% (w/w) of compound 1, compound 2, or a salt thereof (e.g., at any useful weight percentage range, as described herein). In further embodiments, the composition further includes of from about 25% to about 85% (w/w) of one or more pharmaceutically acceptable matrix polymers (e.g., from 25% to 50%, from 25% to 60%, from 25% to 70%, from 25% to 80%, from 35% to 50%, from 35% to 60%, from 35% to 70%, from 35% to 80%, from 35% to 85%, from 50% to 60%, from 50% to 70%, from 50% to 80%, from 50% to 85%, from 60% to 70%, from 60% to 80%, from 60% to 85%, from 70% to 80%, and from 70% to 85%); from about 15% to about 40% (w/w) of one or more binding agents; from about 1% to about 5% (w/w) of one or more disintegrating agents; from about 0.1% to about 2% (w/w) of one or more wetting agents; from about 0.1% to about 1% (w/w) of a glidant; and from about 0.1% to about 1% (w/w) of a lubricant. In particular embodiments, the composition further included of from about 1% to about 5% (w/w) of one or more surfactants (e.g., vitamin E TPGS).

In further embodiments of the seventh and eighth aspects, the method further includes filling the unit dosage form with the solid dispersion.

In some embodiments, the matrix polymer is selected from the group consisting of a cellulose derivative (e.g., a cellulose acetate having from about 10% to about 50% acetyl, an alkyl cellulose, a hydroxyalkyl cellulose, a hydroxyalkylalkyl cellulose, a hydroxyalkylalkyl cellulose ester, a carboxyalkyl cellulose, a carboxyalkylalkyl cellulose, and a carboxyalkyl cellulose ester, or any described herein), a polyacrylate (e.g., a polymethacrylate, a methacrylate copolymer, and an ethacrylate copolymer, or any described herein), a polyvinyl pyrrolidone (e.g., povidone, copovidone, or any described herein), a polyvinyl acetate (e.g., polyvinyl acetate ester, such as polyvinylacetate phthalate (PVAP), and a polyethylene glycol-polyvinylcaprolactam-polyvinylacetate copolymer, or any described herein), or a copolymer of a polyvinyl pyrrolidone and a polyvinyl acetate (e.g., having from 10:90 to 70:30 ratio of N-vinyl-2-pyrrolidone to vinyl acetate). In some embodiments, the cellulose acetate is selected from cellulose acetate phthalate (CAP), methylcellulose acetate phthalate, hydroxypropylmethyl cellulose acetate, and hydroxypropylmethyl cellulose acetate succinate (HPMCAS).

In some embodiments, the mixture or the solution further includes a plasticizer selected from a polyalkylene oxide (e.g., polyethylene glycols, such as PEG 300, PEG 400, and PEG 8000, and polypropylene glycols), a copolymer of ethylene oxide and propylene oxide (e.g., ethoxylated propoxylated block copolymers having the formula $H(OCH_2CH_2)_a(OCHCH_3CH_2)_b(OCH_2CH_2)_aOH$, where a is about 38 and b is about 29 and where a is about 49 and b is about 57), and a polyethoxylated glyceryl ester (e.g., polyoxyl 35 castor oil and polyoxyl 40 castor oil having 40-45 moles of ethylene oxide).

In any of the aspects described herein, the composition includes compound 1 or a salt thereof.

In any of the aspects described herein, the composition includes compound 2 or a salt thereof.

In any of the aspects described herein, the composition includes HPMCAS.

In any of the above aspects, the unit dosage form includes from about 20 mg to about 100 mg (e.g., about 75 mg) of compound 1, compound 2, or a salt thereof.

In any of the above aspects, the compound 1, compound 2, or the salt thereof, is the hydrochloride salt of compound 1, the hydrochloride salt of compound 2, the free base form of compound 1, or the free base form of compound 2.

In any of the above aspects, the compound 1 is the free base form of compound 1.

In any of the above aspects, the unit dosage form is a tablet, hard gelatin capsule, a hard hydroxypropyl methylcellulose capsule, or a soft gelatin capsule.

In any of the above aspects, the unit dosage form includes from about 20 mg to about 250 mg of compound 1, compound 2, or a salt thereof, such as from 20 mg to 30 mg, from 20 mg to 40 mg, from 20 mg to 50 mg, from 20 mg to 75 mg, from 20 mg to 100 mg, from 20 mg to 125 mg, from 20 mg to 150 mg, from 20 mg to 175 mg, from 20 mg to 200 mg, from 20 mg to 225 mg, from 30 mg to 40 mg, from 30 mg to 50 mg, from 30 mg to 75 mg, from 30 mg to 100 mg, from 30 mg to 125 mg, from 30 mg to 150 mg, from 30 mg to 175 mg, from 30 mg to 200 mg, from 30 mg to 225 mg, from 30 mg to 250 mg, from 40 mg to 50 mg, from 40 mg to 75 mg, from 40 mg to 100 mg, from 40 mg to 125 mg, from 40 mg to 150 mg, from 40 mg to 175 mg, from 40 mg to 200 mg, from 40 mg to 225 mg, from 40 mg to 250 mg, from 50 mg to 75 mg, from 50 mg to 100 mg, from 50 mg to 125 mg, from 50 mg to 150 mg, from 50 mg to 175 mg, from 50 mg to 200 mg, from 50 mg to 225 mg, from 50 mg to 250 mg, from 60 mg to 75 mg, from 60 mg to 100 mg, from 60 mg to 125 mg, from 60 mg to 150 mg, from 60 mg to 175 mg, from 60 mg to 200 mg, from 60 mg to 225 mg, from 60 mg to 250 mg, from 70 mg to 75 mg, from 70 mg to 100 mg, from 70 mg to 125 mg, from 70 mg to 150 mg, from 70 mg to 175 mg, from 70 mg to 200 mg, from 70 mg to 225 mg, from 70 mg to 250 mg, from 80 mg to 100 mg, from 80 mg to 125 mg, from 80 mg to 150 mg, from 80 mg to 175 mg, from 80 mg to 200 mg, from 80 mg to 225 mg, from 80 mg to 250 mg, from 90 mg to 100 mg, from 90 mg to 125 mg, from 90 mg to 150 mg, from 90 mg to 175 mg, from 90 mg to 200 mg, from 90 mg to 225 mg, from 90 mg to 250 mg, from 100 mg to 125 mg, from 100 mg to 150 mg, from 100 mg to 175 mg, from 100 mg to 200 mg, from 100 mg to 225 mg, and from 100 mg to 250 mg.

In any of the above aspects, the unit dosage form is administered to achieve a daily amount of from about 25 mg to about 1,600 mg (e.g., from 40 mg to 1,600 mg, from 40 mg to 1,000 mg, from 40 mg to 800 mg, from 40 mg to 700 mg, from 40 mg to 600 mg, from 40 mg to 500 mg, from 40 mg to 400 mg, from 40 mg to 300 mg, from 40 mg to 200 mg, from 50 mg to 1,600 mg, from 50 mg to 1,000 mg, from 50 mg to 800 mg, from 50 mg to 700 mg, from 50 mg to 600 mg, from 50 mg to 500 mg, from 50 mg to 400 mg, from 50 mg to 300 mg, from 50 mg to 200 mg, from 60 mg to 1,600 mg, from 60 mg to 1,000 mg, from 60 mg to 800 mg, from 60 mg to 700 mg, from 60 mg to 600 mg, from 60 mg to 500 mg, from 60 mg to 400 mg, from 60 mg to 300 mg, from 60 mg to 200 mg, from 80 mg to 1,600 mg, from 80 mg to 1,000 mg, from 80 mg to 800 mg, from 80 mg to 700 mg, from 80 mg to 600 mg, from 80 mg to 500 mg, from 80 mg to 400 mg, from 80 mg to 300 mg, from 80 mg to 200 mg, from 100 mg to 1,600 mg, from 100 mg to 1,000 mg, from 100 mg to 800 mg, from 100 mg to 700 mg, from 100 mg to 600 mg, from 100 mg to 500 mg, from 100 mg to 400 mg, from 100 mg to 300 mg, from 100 mg to 200 mg, from 150 mg to 1,600 mg, from 150 mg to 1,000 mg, from 150 mg to 800 mg, from 150 mg to 700 mg, from 150 mg to 600 mg, from 150 mg to 500 mg, from 150 mg to 400 mg, from 150 mg to 300 mg, and from 150 mg to 200 mg, such as from 40 mg to 800 mg and from 80 mg to 320 mg) of compound 1, compound 2, or a salt thereof. In additional aspects, the unit dosage form is administered to achieve a daily amount of up to 1,600 mg (e.g., up to 1,500 mg, up to 1,250 mg, up to 1,000 mg, up to 750 mg, up to 500 mg, up to 450 mg, up to 400 mg, up to 350 mg, up to 300 mg, up to 250 mg, up to 200 mg, up to 150 mg, up to 100 mg, and up to 50 mg, preferably up to 400 mg) or a daily amount of from about 50 mg to about 1,600 mg (e.g., from 150 mg to 200 mg, from 150 mg to 225 mg, from 150 mg to 500 mg, from 150 mg to 750 mg, from 150 mg to 900 mg, from 150 mg to 1,000 mg, from 150 mg to 1,250 mg, from 150 mg to 1,500 mg, from 150 mg to 1,600 mg, from 200 mg to 225 mg, from 200 mg to 500 mg, from 200 mg to 750 mg, from 200 mg to 900 mg, from 200 mg to 1,000 mg, from 200 mg to 1,250 mg, from 200 mg to 1,500 mg, from 200 mg to 1,600 mg, from 225 mg to 500 mg, from 225 mg to 750 mg, from 225 mg to 900 mg, from 225 mg to 1,000 mg, from 225 mg to 1,250 mg, from 225 mg to 1,500 mg, from 225 mg to 1,600 mg, from 500 mg to 750 mg, from 500 mg to 900 mg, from 500 mg to 1,000 mg, from 500 mg to 1,250 mg, from 500 mg to 1,500 mg, from 500 mg to 1,600 mg, from 750 mg to 900 mg, from 750 mg to 1,000 mg, from 750 mg to 1,250 mg, from 750 mg to 1,500 mg, from 750 mg to 1,600 mg, from 900 mg to 1,000 mg, from 900 mg to 1,250 mg, from 900 mg to 1,500 mg, from 900 mg to 1,600 mg, from 1,000 mg to 1,250 mg, from 1,000 mg to 1,500 mg, from 1,000 mg to 1,600 mg, from 1,250 mg to 1,500 mg, from 1,250 mg to 1,600 mg, and from 1,500 mg to 1,600 mg, e.g., about 225 mg) of compound 1, compound 2, or a salt thereof. In further aspects, the unit dosage form is administered one to five times daily (e.g., one, two, three, four, or five times daily).

Definitions

By "pharmaceutically acceptable excipient" is meant any ingredient other than the active ingredient and capable of maintaining the active ingredient in a substantially amorphous form.

By "pharmaceutically acceptable matrix polymer" is meant a polymer suitable for pharmaceutical formulation and capable of forming a solid dispersion.

As used herein, the term "substantially amorphous" refers to a solid dosage form containing compound 1, compound 2, or a salt thereof, in which less than 20% (w/w) of the compound 1, compound 2, or a salt thereof, is present in a crystalline form (e.g., less than 15%, 12%, 10%, 8%, 5%, 3%, or 1% (w/w) is present in a crystalline form, such as between 0.01% and 20%, 0.01% and 15%, 0.01% and 12%, 0.01% and 10%, 0.01% and 8%, 0.01% and 5%, 0.01% and 3%, and 0.01% and 1% (w/w) in crystalline form). The crystalline content of a solid dosage form can be assessed using x-ray diffraction techniques.

As used herein, the term "solid dispersion" encompasses systems having substantially amorphous active ingredient dispersed in a matrix polymer. In certain dosage forms of the invention, the solid dispersion is a form having homogenously dispersed active ingredient throughout the matrix polymer in a manner that results in a single glass transition temperature $T_g$.

As used herein, "about" means +/−10% of the recited value.

As used herein, "bioavailability" refers to the fraction of drug absorbed following administration to a subject or patient under a fasted state. Under fasted states, the bioavailability of compound 1, compound 2, or a salt thereof, formulated as described herein is at least about 15%, but may be greater than 20%, 25%, 30%, 35%, 40%, 45%, or 50% of the dose administered.

By "coefficient of variation" is meant the arithmetic standard deviation divided by the arithmetic mean for a particular pharmacokinetic parameter, where the data is obtained from a pharmacokinetic study involving 10, 12, or more subjects or patients.

By "mean" is meant the arithmetic mean for a particular pharmacokinetic parameter, where the data is obtained from a pharmacokinetic study involving 10, 12, or more subjects or patients.

By "$C_{max}$" is meant the mean peak concentration of a drug achieved in plasma after dosing.

By "$T_{max}$" is meant the mean time after oral administration of a drug when the maximum plasma concentration of the drug or $C_{max}$ is reached.

By "$AUC_\infty$," "$AUC_{0-\infty}$," or "Area Under the Curve$_\infty$" is meant the mean integrated area under the curve for the plasma concentration of a drug, versus time from t=0 to ∞ following dosing.

By "food effect" is meant is meant a difference between any one or more of $C_{max}$, $T_{max}$, $AUC_\infty$, and bioavailability for a drug administered under fasted states in comparison to the drug administered under fed states.

As used herein, "reducing the food effect" refers to narrowing the difference between any one of $C_{max}$, $T_{max}$, $AUC_\infty$, and bioavailability for a drug administered under fasted states in comparison to the drug administered under fed states.

By "fasted" or "fasted states" is meant a subject has not eaten for at least about four hours prior and about four hours subsequent to drug administration.

By "fed" or "fed states" is meant a subject has eaten within about 30 minutes prior to drug administration. The meal can be a fatty meal, and the resulting mean pharmacokinetic parameters can be characteristic of consuming a fatty meal. For example, the "fed state" can be a human who has eaten a United States Food and Drug Administration (FDA) standard high fat breakfast (or another meal containing a comparable quantity of fat and calories) within 30 minutes prior to drug administration. A typical FDA standard breakfast consists of 2 eggs fried in butter, 2 strips of bacon, 2 slices of toast with butter, 4 ounces of hash brown potatoes, and 8 ounces of whole milk. The meal is high in both fat (approximately 50% of total calorie content of the meal) and calories (approximately 800-1,000 calories).

By "pegylated vitamin E compound" is meant a compound or mixture of compounds containing one or more vitamin E moieties (e.g., a tocopherol, tocomonoenol, tocodienol, or tocotrienol) bonded to (e.g., by an ester, amide, or thioester bond) to one or more polyethylene glycol (PEG) moieties via a linker (e.g., a dicarboxylic or tricarboxylic acid). The vitamin E moiety can be any naturally occurring or synthetic form of vitamin E, including α-, β-, γ-, and δ-isoforms, and all stereoisomers of tocopherol, tocomonoenol, tocodienol, and tocotrienol. Linkers include, for example, dicarboxylic acids (e.g., succinic acid, sebacic acid, dodecanedioic acid, suberic acid, or azelaic acid, citraconic acid, methylcitraconic acid, itaconic acid, maleic acid, glutaric acid, glutaconic acid, fumaric acids, and phthalic acids). Exemplary tocopherol polyethylene glycol diesters are D-alpha-tocopheryl PEG succinate, tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol. Each of the PEG moieties of the pegylated vitamin E compound can be any polyethylene glycol or any PEG derivative, and can have a molecular weight of 200-6,000 kDa (e.g., 400-4,000 kDa, 500-2,000 kDa, 750-1,500 kDa, 800-1,200 kDa, 900-1,100 kDa, or about 1,000 kDa). The PEG moieties can be polydisperse; that is, they can have a variety of molecular weights. PEG derivatives include, for example, methylated PEG, propylene glycol, PEG-NHS, PEG-aldehyde, PEG-SH, PEG-NH$_2$, PEG-CO$_2$H, PEG-OMe and other ethers, branched PEGs, and PEG copolymers (e.g., PEG-b-PPG-b-PEG-1100, PEG-PPG-PEG-1900, PPG-PEG-MBE-1700, and PPG-PEG-PPG-2000). Any known source of pegylated vitamin E compound can be used in the present invention. An exemplary pegylated vitamin E compound is tocopheryl PEG-1000 succinate (TPGS-1000), which has a PEG moiety having a molecular weight of 1,000 kDa. A food grade TPGS-1000 is available, for example, under the trade name Eastman Vitamin E TPGS® (Eastman Chemical Company, Kingsport, Tenn.). This TPGS is water-soluble form of natural-source vitamin E, which is prepared by esterification of crystalline D-α-tocopheryl acid succinate with polyethylene glycol 1000 (PEG 1000), and contains between 260 and 300 mg/g total tocopherol. Another exemplary pegylated vitamin E compound is Water Soluble Natural Vitamin E (ZMC-USA, The Woodlands, Tex.). Methods of preparing pegylated vitamin E are described in U.S. Pat. Nos. 2,680,749 and 3,102,078 and in U.S. Publication Nos. 2007/0184117 and 2007/0141203, which are herein incorporated by reference. Pegylated vitamin E compounds also include analogs that differ in chemical composition from tocopheryl PEG succinate (e.g., TPGS-1000) by the substitution, addition, or removal of one or more atoms, methylene $(CH_2)_n$ units, or functional groups. Pegylated vitamin E compounds also include chromanol derivatives (e.g., 6-chromanol PEG-1000 succinate and 6-chromanol PEG-400 succinate), steroid derivatives (e.g., cholesteryl PEG-1000 succinate, cholic acid PEG-1000, dihydro cholic acid PEG-1000, litho-cholic acid PEG-1000, ursodeoxycholic acid PEG-1000, chenodeoxycholic acid PEG-1000), and others (e.g., indomethacin PEG-1000, chromone-2-carboxylic acid PEG-1000, chromone-2-carboxylic acid PEG-1100-OMe, chromone-2-carboxylic acid PEG-1500, chromone-2-carboxylic acid PEG-2000, naproxen PEG-1000, probenecid PEG-1000, 7-carboxymethoxy-4-methyl-coumarin PEG-1000, 5-(4-chlorophenyl)-2-furoic acid PEG-1000, probenecid tocopheryl PEG-1000 succinate, lithocholic acid PEG-1000, and chromone-3-carboxylic acid PEG-1000, 7-hydroxy-coumarinyl-4-acetic acid PEG-1000).

The term "unit dosage form" refers to a physically discrete unit suitable as a unitary dosage, such as a tablet, caplet, hard capsule, or soft capsule, each unit containing a predetermined quantity of a drug.

As used herein, the term "administration" or "administering" refers to peroral (e.g., oral) administration of a drug to a subject or patient.

By "effective" amount is meant the amount of a drug sufficient to treat, prevent, or ameliorate a condition in a subject or patient. The effective amount of compound 1, compound 2, or salt thereof, used to practice the present invention for therapeutic management of a condition varies depending upon one or more of the manner of administration, the age, body weight, sex, and/or general health or malady of the patient. The prescribers will primarily decide the appropriate amount and dosage regimen. Such amount is referred to as an "effective" amount.

As used herein, and as well understood in the art, "to treat" a condition or "treatment" of the condition (e.g., the conditions described herein such as pain (e.g., chronic or acute pain), epilepsy, Alzheimer's disease, Parkinson's disease, cardiovascular disease, diabetes, cancer, sleep disorders, obesity, mood disorders, psychosis such as schizophrenia, tinnitus, amyotrophic lateral sclerosis, glaucoma, ischaemia, spasticity disorders, obsessive compulsive disorder, restless leg syndrome, Tourette syndrome, overactive bladder, renal disease, neuroprotection, addiction, or male birth control) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Other features and advantages of the invention will be apparent from the following detailed description, the drawings, and the claims.

BRIEF DESCRIPTION OF THE DRAWINGS

FIGS. 2A-2C are graphs showing the dissolution rate in gastric media for solid dispersion formulations having 35% (w/w) loading of compound 1 and a gastric-to-FaSSIF (pH 1.0-to-6.5) media transition at 13 minutes. The following solid dispersion formulations were tested: cellulose acetate phthalate (CAP, FIG. 2A), hydroxypropylmethyl cellulose acetate succinate M grade (HPMCAS-M, FIG. 2B), and polyvinyl acetate phthalate (PVAP, FIG. 2C). The total drug species are represented by open circles with error bars, and the free drug species are represented by closed circles with error bars.

FIGS. 3A-3D are graphs showing the dissolution rate in gastric media for solid dispersion formulations having 50% (w/w) loading of compound 1 and a gastric-to-FaSSIF (pH 1.0-to-6.5) media transition at 13 minutes. The following solid dispersion formulations were tested: cellulose acetate phthalate (CAP, FIG. 3A), hydroxypropylmethyl cellulose acetate succinate M grade (HPMCAS-M, FIG. 3B), methacrylic acid-methyl methacrylate copolymer (Eudragit® L 100, FIG. 3C), and polyvinyl acetate phthalate (PVAP, FIG. 3D). The total drug species are represented by open circles with error bars, and the free drug species are represented by closed circles with error bars. The solubility of unformulated compound 1 in the gastric and FaSSIF media is shown in FIG. 3A.

FIG. 11A shows the ratio of $AUC_{0-24}$ for fasted to fed conditions (i.e., $[AUC_{0-24}$ fasted$]/[AUC_{0-24}$ fed$]$) for SDD or Micronized. FIG. 11B shows the ratio of $AUC_{0-24}$ for SDD to Micronized (i.e., $[AUC_{0-24}$ SDD$]/[AUC_{0-24}$ Micronized$]$) for fasted or fed conditions.

DETAILED DESCRIPTION

Figure 1A:
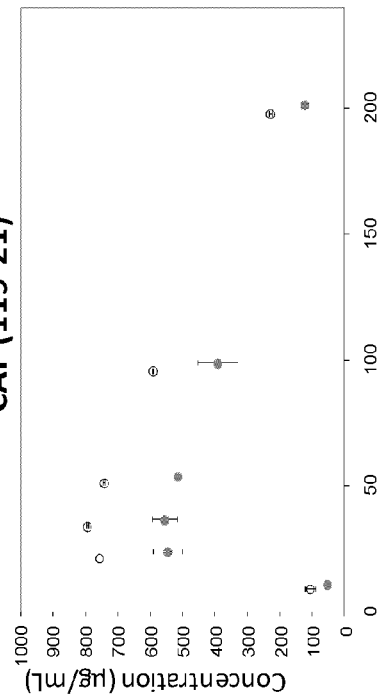
FIGS. 1A-1H are graphs showing the dissolution rate in gastric media for solid dispersion formulations having 20% (w/w) loading of compound 1 and a gastric-to-FaSSIF (pH 1.0-to-6.5) media transition at 13 minutes. The following solid dispersion formulations were tested: carboxymethylethyl cellulose (CMEC, FIG. 1A), cellulose acetate phthalate (CAP, FIG. 1B), hydroxypropylmethyl cellulose acetate succinate M grade (HPMCAS-M, FIG. 1C), polyvinyl acetate phthalate (PVAP, FIG. 1D), methacrylic acid-methyl methacrylate copolymer (Eudragit® L 100, FIG. 1E), polyethylene glycol-polyvinylcaprolactam-polyvinylacetate copolymer (Soluplus®, FIG. 1F), hydroxypropylmethyl cellulose phthalate (HPMCP-H55, FIG. 1G), and polyvinylpyrrolidone vinylacetate copolymer (PVP-VA, FIG. 1H). The total drug species are represented by open circles with error bars, and the free drug species are represented by closed circles with error bars. The solubility of unformulated compound 1 in the gastric and FaSSIF media is shown in FIG. 1A.
Figure 1B:
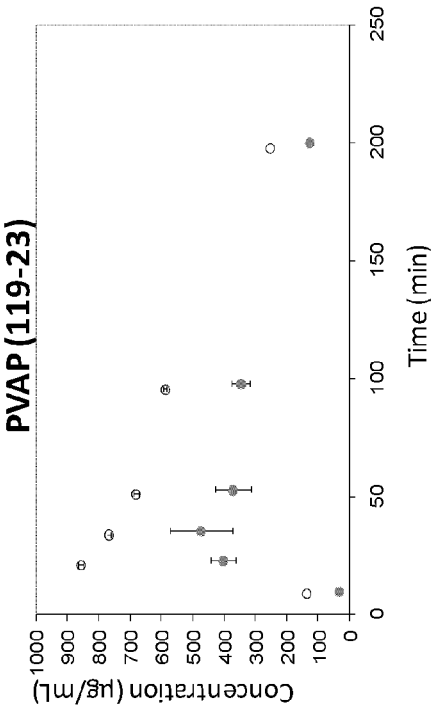
Figure 1C:
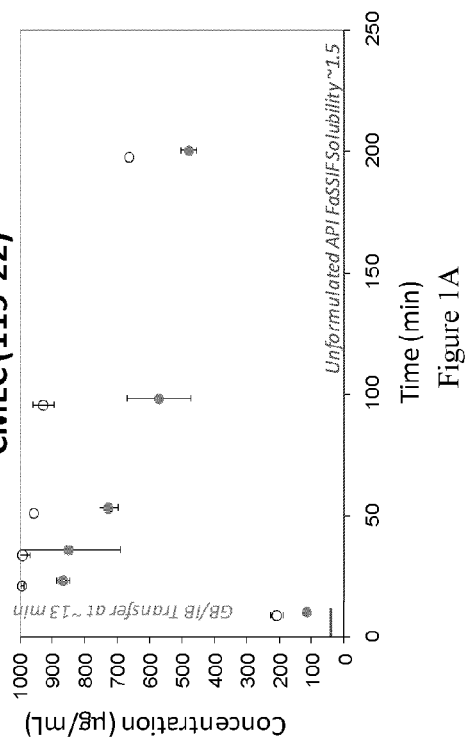
Figure 1D:
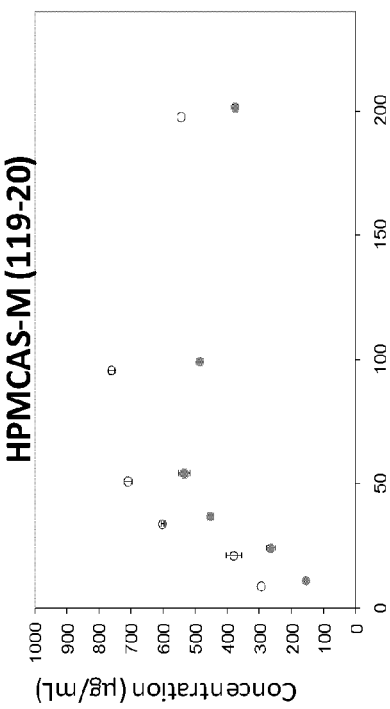
Figure 1F:
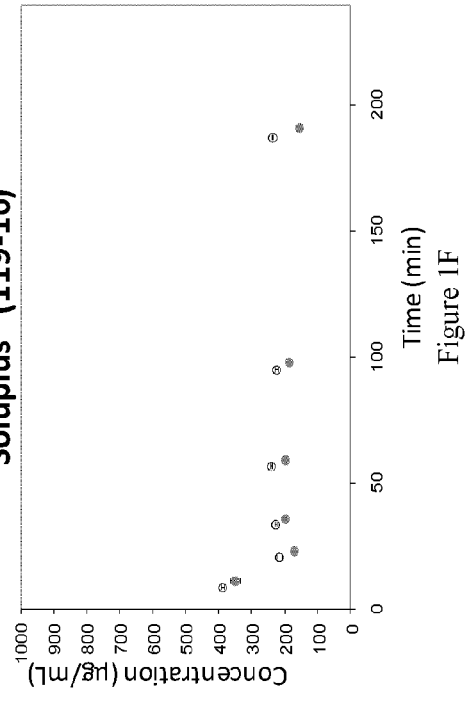
Figure 1H:
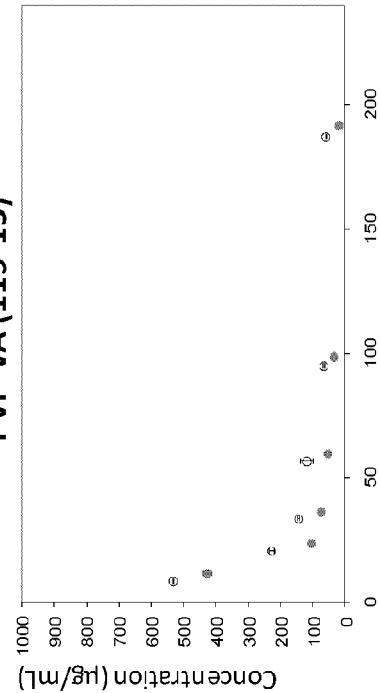
Figure 1E:
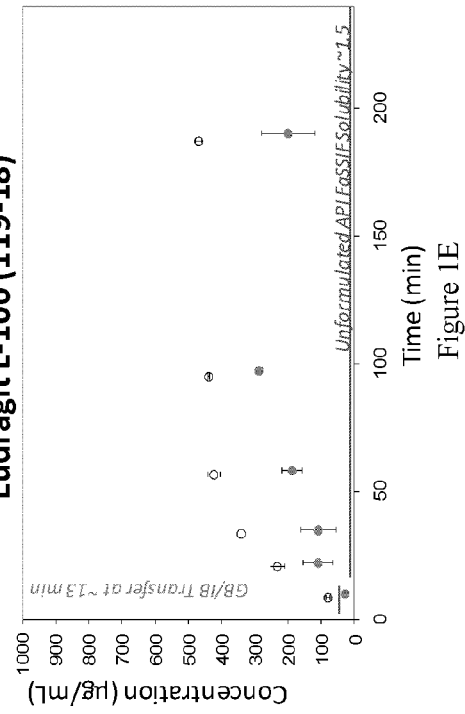
Figure 1G:
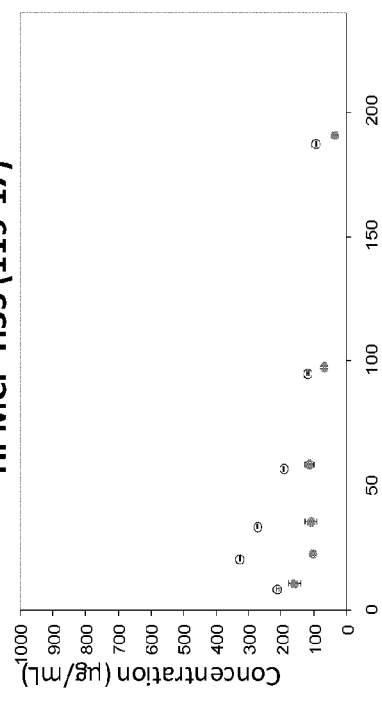

The invention provides methods for treating conditions related to N-type calcium channels, involving administration of 1-(4-benzhydrylpiperazin-1-yl)-3,3-diphenylpropan-1-one (compound 1), a metabolite thereof (e.g., 1-(3,3-diphenylpropanoyl)piperazine (compound 2), or a salt thereof. Non-limiting examples of conditions treatable by this administration are pain and epilepsy.

Compound 1 is a potent and selective N-type calcium channel antagonist, and doses of up to 1,600 mg provided no adverse effects. Yet, compound 1 is also known to have decreased oral bioavailability in the fasted state, as compared to the fed state. Accordingly, the invention provides formulations to increase the oral bioavailability or to reduce patient-to-patient variability in pharmacokinetic behavior of compound 1, compound 2, or a salt thereof. Generally, amorphous forms of a drug are more readily absorbed within the gastric and intestinal system and, thus, have increased bioavailability, as compared to crystalline forms of the drug. These formulations include use of a solid dispersion system to provide a matrix polymer capable of maintaining therapeutically effective amounts of compound 1, compound 2, or a salt thereof, in an amorphous form.

Previously Determined Characteristics of Compound 1

Compound 1 has the following previously determined characteristics:

(i) physical appearance: white to off-white powder;

(ii) solubility: slightly soluble in water (0.2 µg/ml to 2.0 µg/ml at pH of 6.8, 0.03 µg/ml at pH of 6.5, 1.5 µg/ml at pH of 6.5 in FaSSIF, and 55 µg/ml at pH of 1.0) and soluble in acetone (up to 50 mg/ml), propylene glycol, ethanol, and tetrahydrofuran;

(iii) pKa: 5.4;

(iv) log P: 2.6;

(v) M.P.: 123° C. (for free base) and 126° C. (for HCl salt);

(vi) $T_g$: 41.6° C.;

(vii) hygroscopicity (for free base): 0.09% at 70% relative humidity (RH);

(viii) potential isomerism: none;

(ix) $T_{max}$ (for HCl salt): <2 hours (fasted state), 2-5 hours (fed state with normal fat meal), and 4-5 hours (fed state with high fat meal); and (x) $t_{1/2}$ for absorption (for HCl salt): 0.05-0.17 hours (fasted state), 0.5-1.6 hours (fed state with normal fat meal), and 0.8-2.8 hours (fed state with high fat meal). The fed-fasted pharmacokinetic data were collected using a "normal fat" meal consisting of toast with 1 pat of butter, a banana, 2% milk, apple juice, and Honey Nut Cheerios®, where the meal has about 501 calories with 99 calories from fat, 346 calories from carbohydrates, and 56 calories from protein; and using a "high fat" meal consisting of 2 eggs fried in butter, 2 strips of bacon, 2 slices of toast with butter, 4 ounces of hash brown potatoes and 8 ounces of whole milk, where the meal has about 1,000 calories with 500-600 calories from fat, 250 calories from carbohydrates, and 150 calories from protein.

The relative oral bioavailability of compound 1 (HCl salt) has been previously determined in various fed and fasted states in a micronized formulation. This micronized formulation included the following for a 100 mg dose in a #1 HPMC (white opaque) capsule: compound 1 HCl micronized (100.00 mg), Lactose Fast Flo® Fast Flo® composed of a spray-dried mixture of crystalline and amorphous lactose monohydrate (184.80 mg); sodium starch glycolate (19.20 mg); polysorbate 80 (14.40 mg); purified water (used as the granulating fluid and was removed during processing) (QS); and magnesium stearate (1.60 mg), where the resultant fill weight was 320.00 mg. For a 25 mg dose in a #1 gelatin (white opaque) capsule, the formulation included the following: compound 1 HCl micronized (25.00 mg), Lactose Fast Flo® Fast Flo® composed of a spray-dried mixture of crystalline and amorphous lactose monohydrate (264.60 mg); sodium starch glycolate (19.20 mg); polysorbate 80 (9.60 mg); purified water (used as the granulating fluid and was removed during processing) (QS); and magnesium stearate (1.60 mg), where the resultant fill weight was 320.00 mg.

For the micronized formulation, typical values for relative bioavailability included 0.682 for a fasted state relative to a fed state with a normal fat meal; 1.48 for a 25 mg capsule relative to a 100 mg capsule; 5.60 for a fed state with a high fat meal relative to a fed state with a normal fat meal; and $$1 - 0.363 \times \log_{10}\left(\frac{\text{dose}}{100}\right)$$

as a function of dose (mg) relative to a 100 mg dose. Typical values were computed as $100\% \times \sqrt{\omega^2}$, where $\omega^2$=variance (eta), and 68% of the study population were within the range of these typical values. Relative bioavailability values derived from the provided typical values are provided in Table 1.

TABLE 1

| Dosage form | Dose (mg) | Meal* Fasted | Normal fat | High fat |
|---|---|---|---|---|
| 100 mg capsule | 100 | 0.682 | 1.000 | 5.600 |
|  | 200 | 0.607 | 0.891 | 4.988 |
|  | 400 | 0.533 | 0.781 | 4.376 |
|  | 800 | 0.458 | 0.672 | 3.764 |
|  | 1,600 | 0.384 | 0.563 | 3.152 |

TABLE 1-continued

| Dosage form | Dose (mg) | Meal* Fasted | Normal fat | High fat |
|---|---|---|---|---|
| 25 mg capsule | 25 | 1.230 | NA | 10.10 |
|  | 50 | 1.120 | NA | 9.19 |
|  | 100 | 1.009 | NA | 8.29 |
|  | 200 | 0.899 | NA | 7.38 |
|  | 400 | 0.789 | NA | 6.48 |
|  | 800 | 0.678 | NA | 5.57 |
|  | 1,600 | 0.568 | NA | 4.67 |

*Values are expressed relative to the 100 mg dose administered with a normal fat meal.

Synthesis of Compound 1

Compound 1, or a salt thereof, can be synthesized by any useful method, including those described in U.S. Pat. Nos. 6,294,533; 6,387,897; 6,492,375; 6,617,322; 6,949,554; 6,951,862; and 7,064,128; and U.S. Patent Publication Nos. 2006/0084660 and 2004/0259866, incorporated herein by reference in their entirety.

Scheme 1 provides an exemplary schematic for the synthesis of compound 1 (free base). Briefly, the first and second steps provide purified 3,3-diphenylpropionic acid, and these steps can optionally include a recrystallization step in ethyl acetate/heptanes (70/30). Then, the third step provides compound 1, and this step can optionally include use of a toluene azeotrope to remove residual solvents, such as ethanol, tetrahydrofuran (THF), ethyl acetate, commercial grade heptanes, toluene, or isopropanol.

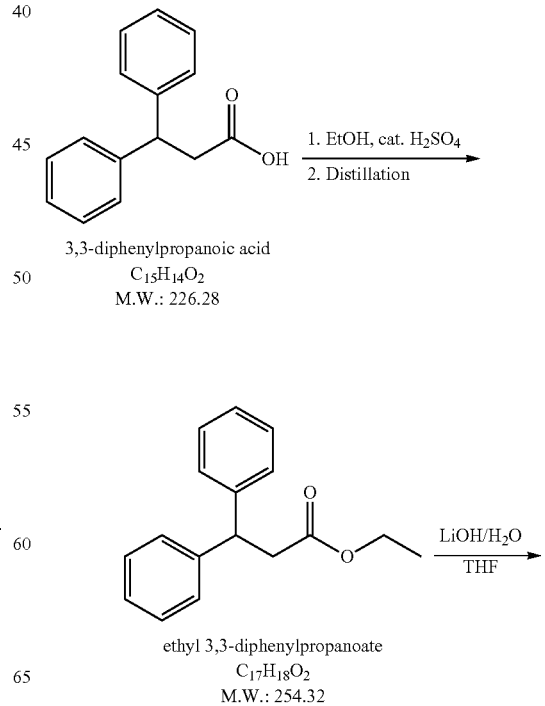

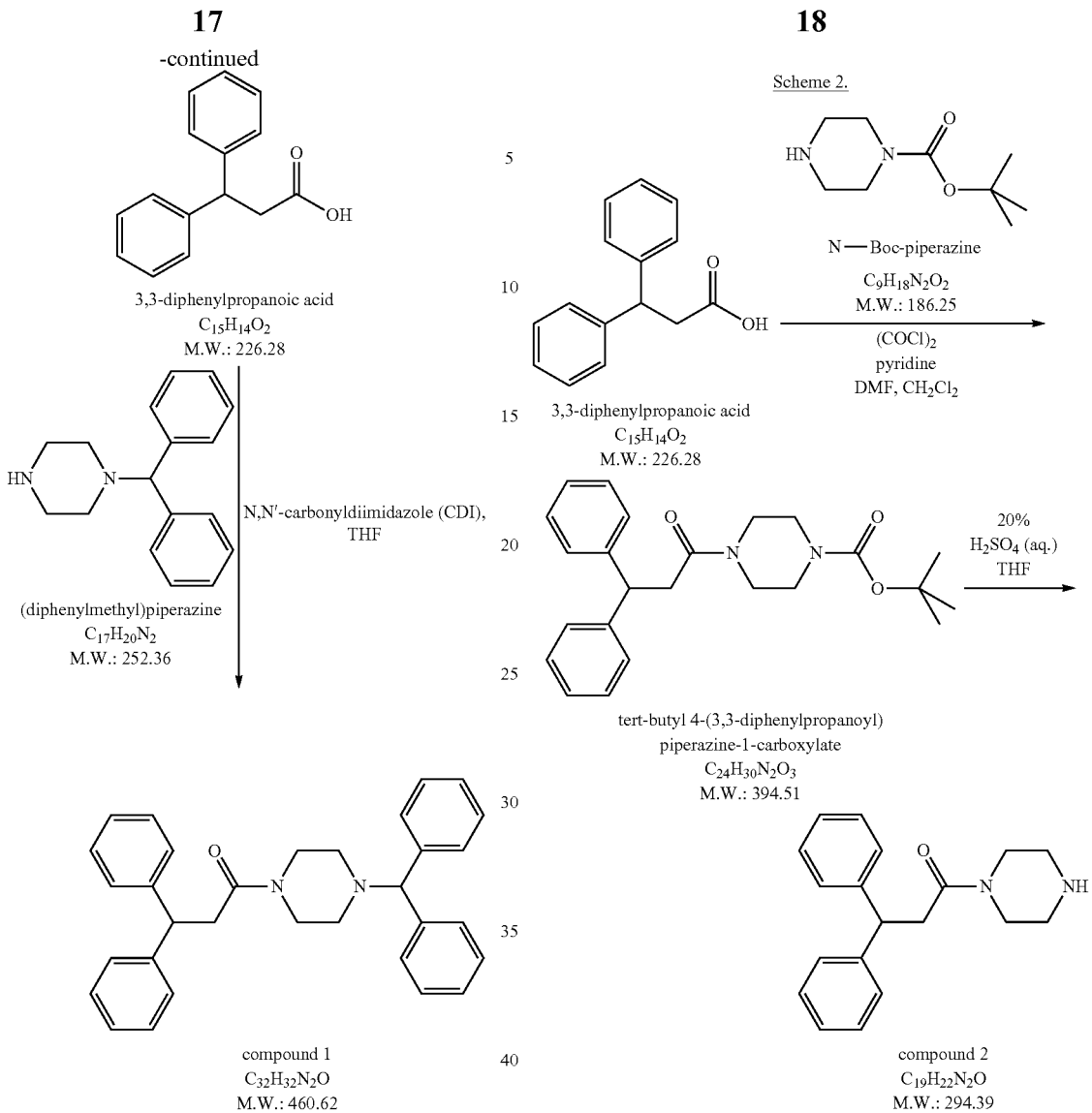

Synthesis of Compound 2

Compound 2, or a salt thereof, can be synthesized by any useful method, including those described in U.S. Pat. Nos. 6,011,035; 6,951,862; and 7,186,726; U.S. Patent Application Publication Nos. 2006/0084660 and 2004/0259866; International Publications Nos. WO 2008/066803, WO 2011/006073, and WO 2007/118323; *J. Am. Chem. Soc.* 77:3142, 1955; and *J. Am. Pharm. Assoc.* 46:279, 1957; incorporated herein by reference in their entirety.

Scheme 2 provides an exemplary schematic for the synthesis of compound 2 (free base). Briefly, the first step provides a protected carbamate compound. The second step provides compound 2. These steps can optionally include a purification step (e.g., where the starting material, 3,3-diphenylpropanoic acid, can be optionally purified, as shown in Scheme 1), a recrystallization step in ethyl acetate/heptanes (e.g., in a ratio of 70/30), or use of a toluene azeotrope to remove residual solvents, such as ethanol, tetrahydrofuran (THF), ethyl acetate, commercial grade heptanes, toluene, or isopropanol.

Pharmaceutically Acceptable Matrix Polymer

Pharmaceutically acceptable matrix polymers include one or more polymers capable of forming a solid dispersion with compound 1, compound 2, or a salt thereof. Two or more matrix polymers can be used to together and can optionally include one or more surfactants and/or plasticizers. Generally, optimal $T_g$ values include from 50° C. to 180° C., which is higher than the melting temperature of compound 1 or compound 2 but lower than the temperature at which compound 1 or compound 2 decomposes. Exemplary $T_g$ values for matrix polymers are from 50° C. to 180° C. (e.g., from 50° C. to 170° C., from 50° C. to 160° C., from 50° C. to 150° C., from 50° C. to 145° C., from 50° C. to 140° C., from 50° C. to 135° C., from 50° C. to 130° C., from 50° C. to 125° C., from 50° C. to 120° C., from 50° C. to 115° C., from 50° C. to 110° C., from 50° C. to 105° C., from 50° C. to 100° C., from 50° C. to 95° C., from 50° C. to 90° C., from 50° C. to 85° C., from 50° C. to 80° C., from 50° C. to 75° C., from 50° C. to 70° C., from 50° C. to 65° C., from 50° C. to 60° C., from 75° C. to 180° C., from 75° C. to 170° C., from 75° C. to 160° C., from 75° C. to 150° C., from 75° C. to 145° C., from 75° C. to 140° C., from 75° C. to 135° C., from 75° C. to 130° C., from 75° C. to 125° C., from 75° C. to 120° C., from 75° C. to 115° C., from 75° C. to 110° C., from 75° C. to 105° C., from 75° C. to 100° C., from 75° C. to 95° C., from 75° C. to 90° C., from 75° C. to 85° C., from 75° C. to 80° C., from 80° C. to 180° C., from 80° C. to 170° C., from 80° C. to 160° C., from 80° C. to 150° C., from 80° C. to 145° C., from 80° C. to 140° C., from 80° C. to 135° C., from 80° C. to 130° C., from 80° C. to 125° C., from 80° C. to 120° C., from 80° C. to 115° C., from 80° C. to 110° C., from 80° C. to 105° C., from 80° C. to 100° C., from 80° C. to 95° C., from 80° C. to 90° C., from 80° C. to 85° C., from 85° C. to 180° C., from 85° C. to 170° C., from 85° C. to 160° C., from 85° C. to 150° C., from 85° C. to 145° C., from 85° C. to 140° C., from 85° C. to 135° C., from 85° C. to 130° C., from 85° C. to 125° C., from 85° C. to 120° C., from 85° C. to 115° C., from 85° C. to 110° C., from 85° C. to 105° C., from 85° C. to 100° C., from 85° C. to 95° C., from 85° C. to 90° C., from 90° C. to 180° C., from 90° C. to 170° C., from 90° C. to 160° C., from 90° C. to 150° C., from 90° C. to 145° C., from 90° C. to 140° C., from 90° C. to 135° C., from 90° C. to 130° C., from 90° C. to 125° C., from 90° C. to 120° C., from 90° C. to 115° C., from 90° C. to 110° C., from 90° C. to 105° C., from 90° C. to 100° C., from 90° C. to 95° C., from 95° C. to 180° C., from 95° C. to 170° C., from 95° C. to 160° C., from 95° C. to 150° C., from 95° C. to 145° C., from 95° C. to 140° C., from 95° C. to 135° C., from 95° C. to 130° C., from 95° C. to 125° C., from 95° C. to 120° C., from 95° C. to 115° C., from 95° C. to 110° C., from 95° C. to 105° C., from 95° C. to 100° C., from 100° C. to 180° C., from 100° C. to 170° C., from 100° C. to 160° C., from 100° C. to 150° C., from 100° C. to 145° C., from 100° C. to 140° C., from 100° C. to 135° C., from 100° C. to 130° C., from 100° C. to 125° C., from 100° C. to 120° C., from 100° C. to 115° C., from 100° C. to 110° C., from 100° C. to 105° C., from 110° C. to 180° C., from 110° C. to 170° C., from 110° C. to 160° C., from 110° C. to 150° C., from 110° C. to 145° C., from 110° C. to 140° C., from 110° C. to 135° C., from 110° C. to 130° C., from 110° C. to 125° C., from 110° C. to 120° C., from 110° C. to 115° C., from 120° C. to 180° C., from 120° C. to 170° C., from 120° C. to 160° C., from 120° C. to 150° C., from 120° C. to 145° C., from 120° C. to 140° C., from 120° C. to 135° C., from 120° C. to 130° C., from 120° C. to 125° C., from 125° C. to 180° C., from 125° C. to 170° C., from 125° C. to 160° C., from 125° C. to 150° C., from 125° C. to 145° C., from 125° C. to 140° C., from 125° C. to 135° C., from 125° C. to 130° C., from 130° C. to 180° C., from 130° C. to 170° C., from 130° C. to 160° C., from 130° C. to 150° C., from 130° C. to 145° C., from 130° C. to 140° C., from 130° C. to 135° C., from 135° C. to 150° C., from 135° C. to 145° C., from 135° C. to 140° C., from 150° C. to 180° C., from 150° C. to 170° C., from 150° C. to 160° C., and from 175° C. to 180° C.).

Exemplary $T_g$ values for a solid dispersion including compound 1 or compound 2 and one or more matrix polymers are from 80° C. to 150° C. (e.g., from 80° C. to 145° C., from 80° C. to 140° C., from 80° C. to 135° C., from 80° C. to 130° C., from 80° C. to 125° C., from 80° C. to 120° C., from 80° C. to 115° C., from 80° C. to 110° C., from 80° C. to 105° C., from 80° C. to 100° C., from 80° C. to 95° C., from 80° C. to 90° C., from 80° C. to 85° C., from 85° C. to 150° C., from 85° C. to 145° C., from 85° C. to 140° C., from 85° C. to 135° C., from 85° C. to 130° C., from 85° C. to 125° C., from 85° C. to 120° C., from 85° C. to 115° C., from 85° C. to 110° C., from 85° C. to 105° C., from 85° C. to 100° C., from 85° C. to 95° C., from 85° C. to 90° C., from 90° C. to 150° C., from 90° C. to 145° C., from 90° C. to 140° C., from 90° C. to 135° C., from 90° C. to 130° C., from 90° C. to 125° C., from 90° C. to 120° C., from 90° C. to 115° C., from 90° C. to 110° C., from 90° C. to 105° C., from 90° C. to 100° C., from 90° C. to 95° C., from 95° C. to 150° C., from 95° C. to 145° C., from 95° C. to 140° C., from 95° C. to 135° C., from 95° C. to 130° C., from 95° C. to 125° C., from 95° C. to 120° C., from 95° C. to 115° C., from 95° C. to 110° C., from 95° C. to 105° C., from 95° C. to 100° C., from 120° C. to 150° C., from 120° C. to 145° C., from 120° C. to 140° C., from 120° C. to 135° C., from 120° C. to 130° C., from 120° C. to 125° C., from 125° C. to 150° C., from 125° C. to 145° C., from 125° C. to 140° C., from 125° C. to 135° C., from 125° C. to 130° C., from 130° C. to 150° C., from 130° C. to 145° C., from 130° C. to 140° C., from 130° C. to 135° C., from 135° C. to 150° C., from 135° C. to 145° C., and from 135° C. to 140° C.).

Exemplary matrix polymers are one or more of ethyl cellulose ($T_g$=133° C.), cellulose acetate phthalate (CAP, $T_g$=171° C.), hydroxypropylmethyl cellulose acetate ($T_g$=177° C.), hydroxypropylmethyl cellulose acetate succinate (HPMCAS, $T_g$=115° C.), hydroxypropylmethyl cellulose phthalate (HPMCP, $T_g$=133° C.), polyvinylpyrrolidone ($T_g$=174° C.), crospovidone ($T_g$=190° C. to 195° C.), polyvinyl alcohol ($T_g$=75° C.), and polyvinyl acetate phthalate ($T_g$=55° C.). Exemplary solid dispersions are those having 20% (w/w) of compound 1 and CMEC ($T_g$=89.4° C.), HPMCAS-M ($T_g$=91.3° C.), CAP ($T_g$=129.9° C.), or PVAP ($T_g$=116.1° C.).

Examples of matrix polymers which can be used in the formulations of the invention are, without limitation, cellulose derivatives, polyacrylates, polyvinyl pyrrolidones, polyvinyl acetates, and copolymers thereof.

Cellulose Derivatives

The formulations of the invention can include one or more cellulose derivatives. Cellulose derivatives generally include those having any number of modifications to the free hydroxyl groups in cellulose.

In some examples, the cellulose derivative is a cellulose acetate having from 10% to 50% acetyl. Referring to cellulose derivatives, % refers to the proportion of the free hydroxyl groups esterified with a functional group. For example, "10% acetyl" refers to a derivative having 10% of the free hydroxyl groups in cellulose esterified with an acetyl group.

Particular examples of cellulose acetates are cellulose acetate phthalates (CAP), such as those having 35% phthalyl, 24% acetyl (available as Cellacefate from Eastman Chemical Company, Kingsport, Tenn.); methylcellulose acetate phthalates; hydroxypropylmethyl cellulose acetates; and hydroxypropylmethyl cellulose acetate succinates (HPMCAS), such as M grade having 9% acetyl/11% succinoyl (e.g., HPMCAS having a mean particle size of 5 μm (i.e., HPMCAS-MF, fine powder grade) or having a mean particle size of 1 mm (i.e., HPMCAS-MG, granular grade)), H grade having 12% acetyl/6% succinoyl (e.g., HPMCAS having a mean particle size of 5 μm (i.e., HPMCAS-HF, fine powder grade) or having a mean particle size of 1 mm (i.e., HPMCAS-HG, granular grade)), and L grade having 8% acetyl/15% succinoyl (e.g., HPMCAS having a mean particle size of 5 μm (i.e., HPMCAS-LF, fine powder grade) or having a mean particle size of 1 mm (i.e., HPMCAS-LG, granular grade)).

Additional exemplary cellulose derivatives are alkyl celluloses, such as methyl cellulose (Methocel™ A) or ethylcellulose (Ethocel®); hydroxyalkyl celluloses, such as hydroxymethyl cellulose, hydroxyethyl cellulose, hydroxypropyl cellulose (HPC, e.g., low-substituted HPC having 11% hydroxypropyl or 8% hydroxypropyl), and hydroxybutyl cellulose; hydroxyalkylalkyl celluloses, such as hydroxyethylmethyl cellulose and hydroxypropylmethyl cellulose (hypromellose, HPMC, e.g., those having about 19-24% methoxyl/7-12% hydroxypropxyl (Methocel™ K, including those having apparent viscosity (2% in water at 20° C.) of 80-120 cP (Methocel™ K100), 3,000-5,600 cP (Methocel™ K4M), 11,250-21,000 cP (Methocel™ K15M), 80,000-120,000 cP (Methocel™ K100M), available from Dow Chemical Co.), 28-30% methoxyl/7-12% hydroxypropyl (Methocel™ E, including those having apparent viscosity (2% in water at 20° C.) of 3,000-5,600 cP (Methocel™ E4M) and 7,500-14,000 cP (Methocel™ E10M), also available from Dow Chemical Co.), 23% methoxyl/10% hydroxypropyl (Metolose® SR, available from Shin-Etsu Chemical Co., Ltd., Tokyo, Japan), 23%-29% methoxyl/8%-9% hydroxypropxyl (Metolose®, also available from Shin-Etsu Chemical Co., Ltd.), 29% methoxyl/9% hydroxypropyl (Hypromellose USP, substitution 2910), and 23% methoxyl/6% hydroxypropyl (Hypromellose USP, substitution 2208)); hydroxyalkylalkyl cellulose esters, such as hydroxypropylmethyl cellulose phthalate (HPMCP) (e.g., HP 55 grade having 31% nominal phthalyl content and HP-55S or HP-50 grades having 24% nominal phthalyl content); carboxyalkyl celluloses, such as carboxymethyl cellulose and alkali metal salts thereof, such as sodium salts; carboxyalkylalkyl celluloses, such as carboxymethylethyl cellulose; and carboxyalkyl cellulose esters, such as carboxymethyl cellulose butyrate, carboxymethyl cellulose propionate, carboxymethyl cellulose acetate butyrate, and carboxymethyl cellulose acetate propionate.

Any of the cellulose derivatives herein can be further cross-linked or copolymerized (e.g., with any matrix polymer described herein).

Polyacrylates

The formulations of the invention can include one or more polyacrylates or copolymers thereof.

Exemplary polyacrylates are polymethacrylates; methacrylate copolymers, such as methacrylic acid-methyl methacrylate copolymers having a 1:1 ratio of free carboxyl groups to ester groups (e.g., Eudragit® L 100, MW~125,000 g/mol) and a 1:2 ratio of free carboxyl groups to ester groups (Eudragit® S 100, MW~125,000 g/mol), dimethylaminoethyl methacrylate-butyl methacrylate-methyl methacrylate copolymers (e.g., having a ratio of 2:1:1 of dimethylaminoethyl methacrylate-butyl methacrylate-methyl methacrylate and in powder, granule, or solution forms, i.e., Eudragit® E PO, Eudragit® E 100, or Eudragit® E 12.5, respectively), and diethylaminoethyl methacrylic acid-methyl methacrylate copolymers (e.g., Eudragit® E); and ethacrylate copolymers, such as methacrylic acid ethacrylate copolymers having a 50:50 ratio of methacrylic acid to ethacrylate (e.g., Kollicoat® MAE 100P or Eudragit®L 100-55, MW~320,000 g/mol)

Polyvinyl Pyrrolidones and Polyvinyl Acetates

The formulations of the invention can include one or more polyvinyl pyrrolidones, polyvinyl acetates, or copolymers thereof.

Exemplary polyvinyl pyrrolidones and polyvinyl acetates are polyvinyl pyrrolidones (e.g., povidone, PVP, or soluble povidone) having molecular weights of about 2,500 (Kollidon@12 PF, weight-average molecular weight between 2,000 to 3,000), about 9,000 (Kollidon®17 PF, weight-average molecular weight between 7,000 to 11,000), about 25,000 (Kollidon®25, weight-average molecular weight between 28,000 to 34,000), about 50,000 (Kollidon®30, weight-average molecular weight between 44,000 to 54,000), and about 1,250,000 (Kollidon®90 or Kollidon®90F, weight-average molecular weight between 1,000,000 to 1,500,000); polyvinyl acetate esters, such as polyvinyl acetate phthalate (PVAP); polyethylene glycol-polyvinyl acetate copolymers, such as polyethylene glycol-polyvinylcaprolactam-polyvinylacetate copolymer (Soluplus®); and polyvinylpyrrolidone-polyvinyl acetate copolymers (PVP-VA), such as those having a 60:40 ratio of N-vinyl-2-pyrrolidone to vinyl acetate (copovidone, also available as Kollidon® VA 64) and a 20:80 ratio of N-vinyl-2-pyrrolidone to vinyl acetate (Kollidon® SR).

Hydrophobic-Lipophilic Balance

The matrix polymers, plasticizers, and surfactants used in the formulations of the invention can be characterized by the hydrophobic-lipophilic balance ("HLB"). HLB generally provides the degree of hydrophobicity or lipophilicity for a given molecule. HLB can be determined by any useful method, including the formula HLB=20×Mh/M, where Mh is the molecular mass of the hydrophilic region of the molecule and M is the molecule mass of the molecule, and the formula $HLB=7+\Sigma_i N_i^h - \Sigma_j N_j^l$, where i is the number of groups, $N_i^h$ is a value for each $i^{th}$ hydrophilic group, and $N_i^l$ is the value for each $i^{th}$ lipophilic group. Values of $N^h$ and $N^l$ depend on the type of hydrophilic and lipophilic group, respectively. Exemplary values for $N^h$ include 38.7 for —$SO_4Na$, 21.1 for —$CO_2K$, 19.1 for —$CO_2Na$, 9.4 for tertiary amine N, 6.8 for ester (sorbitan ring), 2.4 for ester (free), 2.1 for —$CO_2H$, 1.9 for —OH (free), 1.3 for —O—, 0.5 for —OH (sorbitan ring), and 0.33 for —($CH_2CH_2O$)—; and for $N^l$ include −1.66 for benzyl, −0.475 for —CH—, —$CH_2$—, —$CH_3$, and =CH—, and −0.13 for —($CH_2CH_2CH_2O$)—.

Plasticizers

The formulations of the invention optionally include one or more plasticizers. Generally, plasticizers can be used to reduce the glass transition temperature $T_g$ or to decrease viscosity of the mixture of compound 1, compound 2, or a salt thereof, with the matrix polymer. Exemplary plasticizers are polyalkylene oxides, such as polyethylene glycols (e.g., PEG 300, PEG 400, PEG 4000, or PEG 8000) and polypropylene glycols; copolymers of ethylene oxide and propylene oxide, such as ethoxylated propoxylated block copolymers having the formula $H(OCH_2CH_2)_a(OCHCH_3CH_2)_b(OCH_2CH_2)_aOH$, where a is about 12 and b is about 20 (Poloxamer® 124), where a is about 38 and b is about 29, where a is about 80 and b is about 27 (Poloxamer® 188), where a is about 64 and b is about 37 (Poloxamer® 237), where a is about 141 and b is about 44 (Poloxamer® 338), where a is about 49 and b is about 57, and where a is about 101 and b is about 56 (Poloxamer® 407); and polyethoxylated glyceryl esters, such as polyoxyl 35 castor oil (Cremophor® EL, HLB=12 to 14) and polyoxyl 40 castor oil having 40-45 moles of ethylene oxide (Cremophor® RH-40, HLB=14 to 16).

Surfactants

Exemplary surfactants are liquid and solid polyethoxylated esters of fatty acids, such as polyoxyl 40 stearate (Myrj® 52, hydrophobic-lipophilic balance ("HLB")=17), PEG 400 monostearate, also known as polyoxyl 8 stearate (Myrj® 45, HLB=11), and PEG 660 hydroxystearate, also known as PEG 15 hydroxystearate (Solutol® HS 15, HLB=14 to 16); polyethoxylated alkyl ethers, such as polyoxyl 10 oleyl ether (Brij® 97, HLB=12.4) and PEG 25 cetostearyl ether (Cremophor® A 25, HLB=15 to 17); polyethoxylated sorbitan esters, such as polysorbate 20 (Tween® 20, HLB=15) and polysorbate 80 (Tween® 80, HLB=11.5); polyethoxylated glyceryl esters having high HLB values (e.g., from 10 to 20), such as polyoxyl 35 castor oil (Cremophor® EL, HLB=12 to 14) and polyoxyl 40 castor oil having 40-45 moles of ethylene oxide (Cremophor® RH-40, HLB=14 to 16); polyethoxylated glyceryl esters of fatty acids having high HLB values (e.g., from 10 to 20), such as a mixture of PEG 6 caprylic/capric glyceryl esters having <2% $C_6$/50%-80% $C_8$/20%-50% $C_{10}$/<3% $C_{12}$/<1% $C_{14}$ (Softigen® 767, HLB=19), a mixture of PEG 8 caprylic/capric glyceryl esters having 50%-80% $C_8$/20%-50% $C_{10}$/<3% $C_{12}$/<1% $C_{18}$ (Labrasol®, HLB=14), a mixture of PEG 32 lauryl glyceryl esters having 40%-50% $C_{12}$/14%-24% $C_{14}$/4%-10% $C_8$/3-9% $C_{10}$/4%-14% $C_{16}$/5%-15% $C_{18}$ (Gelucire® 44/14, HLB=14), and a mixture of PEG 32 stearyl glyceryl esters having 40%-50% $C_{16}$/48%-58% $C_{18}$ (Gelucire® 50/13, HLB=13); polyethoxylated vitamin analogs, such as D-alpha-tocopheryl PEG 1000 succinate (HLB=13); and ethoxylated propoxylated block copolymers having formula $H(OCH_2CH_2)_a(OCHCH_3CH_2)_b(OCH_2CH_2)_aOH$, where a is about 12 and b is about 20 (Poloxamer® 124), where a is about 38 and b is about 29, where a is about 80 and b is about 27 (Poloxamer® 188), where a is about 64 and b is about 37 (Poloxamer® 237), where a is about 141 and b is about 44 (Poloxamer® 338), where a is about 49 and b is about 57, and where a is about 101 and b is about 56 (Poloxamer® 407).

Tocopheryl polyethylene glycol succinate (tocopheryl PEG-1000 succinate) and related pegylated vitamin E compounds can be used in the pharmaceutical composition of the invention. Tocopheryl PEG-1000 succinate has the following structure:

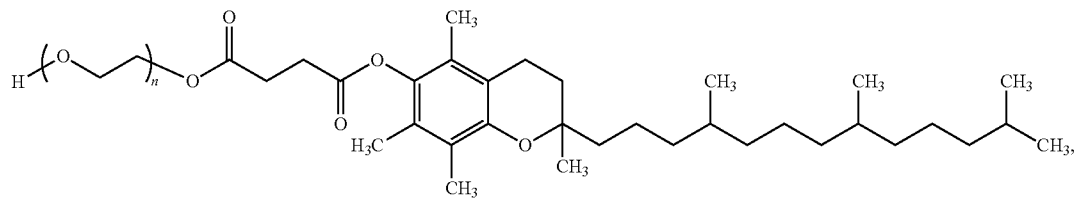

where n is an integer (e.g., the molecular weight is about 1513 for tocopheryl PEG-1000 succinate).

Related pegylated vitamin E compounds include additives formed using different diacid linkers, different length polyethylene glycol tails, and different isoforms (e.g. α-, β-, γ-, or δ-) of tocopherol, tocomonoenol, tocodienol, and tocotrienol. These include α-tocopherol, α-tocomonoenol, α-tocodienol, α-tocotrienol, β-tocopherol, β-tocomonoenol, β-tocodienol, β-tocotrienol, γ-tocopherol, γ-tocomonoenol, γ-tocodienol, γ-tocotrienol, δ-tocopherol, δ-tocomonoenol, δ-tocodienol, δ-tocotrienol, and any stereoisomer thereof. Suitable vitamin E compounds of the present invention also include desmethyl-tocopherol, desmethyl-tocomonoenol, desmethyl-tocodienol, desmethyl-tocotrienol, and any stereoisomer thereof. Furthermore, when a compound disclosed herein contains one or more chiral atoms where stereochemistry is unspecified, it will be understood that each stereoisomer of the compound is individually disclosed as if the structure of each stereoisomer were explicitly drawn. In certain embodiments of the invention, the vitamin E compound may be a naturally-occurring D-stereoisomer of vitamin E.

The vitamin E moieties of the present invention may be naturally occurring or synthetic. Certain embodiments of the invention include a naturally occurring vitamin E compound such as an extract from a food source. For example, α-tocopherol, α-tocotrienol, β-tocopherol, β-tocotrienol, γ-tocopherol, γ-tocotrienol, δ-tocopherol, and δ-tocotrienol are available naturally from fortified cereals, green vegetables, nuts, seeds, and vegetable oils. Methods of extracting vitamin E from natural sources have been described, for example, in U.S. Pat. Nos. 6,743,450; 6,838,104; 7,161,055; and 7,544,822, which are hereby incorporated by reference.

The pegylated vitamin E compound can include synthetic vitamin E moieties. An exemplary method for making α-tocopherol is the reaction of trimethylhydroquinone (TMHQ) with iso-phytol (3,7,11,15-tetramethylhexadec-1-en-3-ol) in a condensation reaction with a catalyst. It will be apparent to one skilled in the art that other tocopherol, tocomonoenol, tocodienol, and tocotrienol isoforms and their derivatives can also be prepared using a similar strategy starting from appropriate precursors. For example, the starting compounds may be TMHQ and 3,7,11,15-tetramethylhexadec-2-en-1-ol. An additional method of making vitamin E with isophytol under relatively mild conditions has been described by Wehrli et al., *J. Org. Chem.* 36:2910 (1971). Methods for synthesizing unsaturated side chains of vitamin E are described in U.S. Pat. No. 4,168,271, which is hereby incorporated by reference. Additional methods of synthesizing vitamin E side chains have been reviewed by Stalla-Bourdillon, *Ind. Chim. Belg.* 35, 13 (1970). Additional methods of synthesizing tocopherols are described in U.S. Pat. Nos. 5,523,420 and 6,005,122, each of which is incorporated herein by reference. Additional methods of synthesizing tocotrienols are described in U.S. Pat. No. 7,038,067, which is hereby incorporated by reference.

Pegylated vitamin E compounds can include different linkers, for example, dicarboxylic acids (e.g., succinic acid, sebacic acid, dodecanedioic acid, suberic acid, or azelaic acid, citraconic acid, methylcitraconic acid, itaconic acid, maleic acid, glutaric acid, glutaconic acid, fumaric acids, and phthalic acids). Exemplary tocopherol polyethylene glycol diesters are TPGS-1000, tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol.

The PEG moiety of the pegylated vitamin E compound can be any polyethylene glycol or derivative thereof, and can have a molecular weight of 200-6,000 kDa (e.g., 400-4,000 kDa, 500-2,000 kDa, 750-1,500 kDa, 800-1,200 kDa, 900-1,100 kDa, or about 1,000 kDa). PEG derivatives include, for example, methylated PEG, polypropylene glycol (PPG), PEG-NHS, PEG-aldehyde, PEG-SH, PEG-NH$_2$, PEG-CO$_2$H, PEG-OMe, as well as other ethers, branched PEGs, and PEG copolymers (e.g., PEG-b-PPG-b-PEG-1100, PEG-PPG-PEG-1900, PPG-PEG-MBE-1700, and PPG-PEG-PPG-2000).

Any known source of pegylated vitamin E compound can be used in the present invention. Pegylated vitamin E compounds typically have an HLB value of between about 16 and about 18 (e.g., between 18 and 18). An exemplary pegylated vitamin E compound is tocopheryl PEG-1000 succinate (also referred to herein as "TPGS 1000"), which has a PEG moiety having a molecular weight of 1,000 kDa. A food grade TPGS 1000 is available, for example, under the trade name Eastman Vitamin E TPGS® (Eastman Chemical Company, Kingsport, Tenn.). This TPGS is water-soluble form of natural-source vitamin E, which is prepared by esterification of crystalline D-α-tocopheryl acid succinate with polyethylene glycol 1000 (PEG 1000), and contains between 260 and 300 mg/g total tocopherol. Another exemplary pegylated vitamin E compound is Water Soluble Natural Vitamin E (ZMC-USA, The Woodlands, Tex.). Methods of preparing pegylated vitamin E compounds are described in U.S. Pat. Nos. 2,680,749 and 3,102,078 and in U.S. Publication Nos. 2007/0184117 and 2007/0141203, which are herein incorporated by reference.

Pegylated vitamin E compounds also include chromanol derivatives (e.g., 6-chromanol PEG-1000 succinate and 6-chromanol PEG-400 succinate), steroid derivatives (e.g., cholesteryl PEG-1000 succinate, cholic acid PEG-1000, dihydrocholic acid PEG-1000, litho-cholic acid PEG-1000, ursodeoxycholic acid PEG-1000, chenodeoxycholic acid PEG-1000), and others (e.g., indomethacin PEG-1000, chromone-2-carboxylic acid PEG-1000, chromone-2-carboxylic acid PEG-1100-OMe, chromone-2-carboxylic acid PEG-1500, chromone-2-carboxylic acid PEG-2000, naproxen PEG-1000, probenecid PEG-1000, 7-carboxymethoxy-4-methyl-coumarin PEG-1000, 5-(4-chlorophenyl)-2-furoic acid PEG-1000, probenecid tocopheryl PEG-1000 succinate, lithocholic acid PEG-1000, and chromone-3-carboxylic acid PEG-1000, 7-hydroxy-coumarinyl-4-acetic acid PEG-1000).

Pharmaceutically Acceptable Excipients

Pharmaceutically acceptable excipients include one or more other ingredient capable of maintaining compound 1, compound 2, or a salt thereof, in a substantially amorphous form. In particular embodiments, the excipient is a pharmaceutically acceptable matrix polymer, as described herein.

Exemplary excipients are antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Additional non-limiting exemplary excipients are: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

These excipients may be, for example, inert diluents or fillers (e.g., sucrose, sorbitol, sugar, mannitol, microcrystalline cellulose, starches including potato starch, kaolin, calcium carbonate, sodium chloride, lactose, calcium phosphate, calcium sulfate, and sodium phosphate); granulating and disintegrating agents (e.g., cellulose derivatives including microcrystalline cellulose, starches including potato starch, croscarmellose sodium, alginates, and alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, and polyethylene glycol); and lubricants, glidants, and antiadhesives (e.g., magnesium stearate, calcium stearate, zinc stearate, sodium stearyl fumarate, sodium lauryl sulfate, stearic acid, silicas, hydrogenated vegetable oils, and talc). Other pharmaceutically acceptable excipients can be colorants, flavoring agents, plasticizers, humectants, buffering agents, and the like.

Methods of Making Solid Dispersion Systems

The pharmaceutical composition including the solid dispersion (e.g., a spray dried dispersion (SDD) or a hot melt extrusion (HME)) can be made using any useful method. Generally, one or more matrix polymers and compound 1, compound 2, or a salt thereof, are combined either with or without a solvent (e.g., one or more of dimethyl acetamide, dimethyl formamide, pyrrolidone, methylpyrrolidone, methanol, ethanol, and acetone) to form a mixture (e.g., a liquid mixture) or a solution. Optionally, the matrix polymer and compound 1 or compound 2, either with or without additional excipients, can be heated near or past the glass transition temperature $T_g$ or melting temperature $T_m$ to form a liquid mixture. Then, the resultant solution can be spray dried to form a solid dispersion. Alternatively, the method includes a hot-melt extrusion process, where the mixture is heated to form a homogenous molten mass, extruded, and cooled to form a solid dispersion. The extrudates can optionally be pelletized or milled to form a solid dispersion amenable for further processing in a suitable unit dosage form.

Finally, the solid dispersion is used for filling any one of the unit dosage forms described herein (e.g., a capsule) or for tabletting. The solid dispersion can optionally be further processed before filling or tabletting. Exemplary further processing includes spheronizing, pelletizing, milling, injection molding, sieving, and/or calendaring the solid dispersion.

Spray Dried Processes

The compositions of the invention can be prepared by any useful process, such as spray drying to form a spray dried dispersion (SDD). In one example, one or more matrix polymers and compound 1 or compound 2 are combined with one or more solvents (e.g., acetone) to form a solution having about 4% (w/w) to about 15% (w/w) of total solids. Percentage (w/w) total solids is determined by dividing the total mass of the compound and one or more matrix polymers by the total mass of the compound, one or more matrix polymers, and one or more solvents. The solution can then be spray dried to form a SDD, which can optionally be further drying steps. In particular embodiments, the SDD includes about 20% (w/w) of compound 1 or compound 2 with the one or more matrix polymers (i.e., the weight ratio of compound 1 or compound 2 to the matrix polymer is about 1:4).

For example, to produce a 20% (w/w) compound 1 in a SDD, a solution was prepared having about 2% (w/w) compound 1 and about 8% (w/w) of a pharmaceutically acceptable matrix polymer or a combination of a pharmaceutically acceptable matrix polymer in acetone. The solution was then spray dried at the appropriate temperature (e.g., between about 95° C. and 110° C. for HPMCAS at the appropriate solution flow rate).

Exemplary matrix polymers for SDD include a cellulose derivative, such as HPMCAS, e.g., type MG or MF, or CAP; and a polyvinyl acetate, such as PVAP.

The resultant SDD can be blended with one or more excipients, as described herein, and then granulated and/or compacted to produce a final blend for encapsulating or tabletting. In particular embodiments, the one or more excipients include a binding agent, a filler, a disintegrating agent, a wetting agent, a glidant, and a lubricant.

Hot Melt Extrusion Processes

In some embodiments, the compositions of the invention are prepared by hot melt extrusion (HME). In one example, one or more matrix polymers and compound 1 or compound 2 are combined to form a mixture, where this mixture can optionally include a surfactant. The mixture can then be fed into a pre-heated extruder (e.g., an extruder having temperature zones between about 75° C. to about 145° C.) to produce an initial extrudate. The extrudate is then pelletized and milled (e.g., to a size less than about 500 µm) to produce a fine milled extrudate.

For example, to produce a 20% (w/w) compound 1 extrudate, a pre-blend was prepared having 20% (w/w) compound 1 and 80% (w/w) of a pharmaceutically acceptable matrix polymer or a combination of a pharmaceutically acceptable matrix polymer with a surfactant (e.g., any pharmaceutically acceptable matrix polymer and/or surfactant described herein, e.g., a combination of 75% (w/w) HPMCAS-MF with 5% (w/w) vitamin E TPGS). Any component of the pre-blend can be pre-milled or pre-sieved. For example, the pharmaceutically acceptable matrix polymer and/or surfactant can be milled through a bar rotor and rasping screen to reduce particle size (e.g., reduce down to ≤600 microns); and/or compound 1 can be pre-sieved. Then, the pre-blend was processed using a co-rotating twin screw extruder, and the resultant extrudate was processed further by milling (pelletizing) to reduce its particle size (e.g., ≤500 microns). The milled/pelletized extrudate was sieved and blended with various pharmaceutically acceptable excipients (e.g., any described herein), where the resultant blend was then co-milled. The co-milled blend can be further processed by adding a lubricant (e.g., magnesium stearate), and the resultant, processed blend can be used to fill a unit dosage form (e.g., a capsule).

Matrix polymers for hot melt extrusion include a cellulose derivative, such as HPMCAS, e.g., type MG or MF; a polyvinyl pyrrolidone (PVP), such as povidone having a molecular weight of about 50,000 (Kollidon®30, weight-average molecular weight between 44,000 to 54,000); a polyvinyl acetate; or a copolymer of a polyvinyl pyrrolidone and a polyvinyl acetate (PVP-VA), such as those having a 60:40 ratio of N-vinyl-2-pyrrolidone to vinyl acetate (copovidone, also available as Kollidon® VA 64) and a 20:80 ratio of N-vinyl-2-pyrrolidone to vinyl acetate (Kollidon® SR).

In particular embodiments, any surfactant or wetting agent described herein can be included in the mixture to enhance dissolution and/or enhance stability. An exemplary surfactant includes a pegylated vitamin E compound, such as any described herein (e.g., D-alpha-tocopheryl PEG 1000 succinate), in a useful amount (e.g., from about 3% to about 10% (w/w), e.g., about 5% (w/w)).

The resultant extrudate can be blended with one or more excipients, as described herein, and then milled, blended, granulated and/or compacted to produce a final blend for encapsulating or tabletting. In particular embodiments, the one or more excipients include a binding agent, a filler, a surfactant (e.g., a pegylated vitamin E compound), a disintegrating agent, a wetting agent, a glidant, and a lubricant.

Dosage and Administration

For administration to animal or human subjects, the dosage of compound 1, compound 2, or a salt thereof, is typically 0.1 to 15 mg/kg, more preferably 3 to 5 mg/kg. However, dosage levels can be highly dependent on the nature of the condition, drug efficacy, the condition of the patient, the judgment of the practitioner, and the frequency and mode of administration.

Compound 1, compound 2, or a salt thereof, is preferably provided in a therapeutically effective amount, which may be, for example, a daily amount of from 25 mg to 1,600 mg, more preferably 40 mg to 800 mg, and even more preferably 80 mg to 320 mg. In one embodiment, a pharmaceutical composition comprising a compound 1, compound 2, or a salt thereof, comprises a capsule, for example in unit dosage form having from 20 mg to 250 mg of compound 1, compound 2, or a salt thereof, (e.g., from 20 mg to 250 mg, such as from 20 mg to 30 mg, from 20 mg to 40 mg, from 20 mg to 50 mg, from 20 mg to 75 mg, from 20 mg to 100 mg, from 20 mg to 125 mg, from 20 mg to 150 mg, from 20 mg to 175 mg, from 20 mg to 200 mg, from 20 mg to 225 mg, from 30 mg to 40 mg, from 30 mg to 50 mg, from 30 mg to 75 mg, from 30 mg to 100 mg, from 30 mg to 125 mg, from 30 mg to 150 mg, from 30 mg to 175 mg, from 30 mg to 200 mg, from 30 mg to 225 mg, from 30 mg to 250 mg, from 40 mg to 50 mg, from 40 mg to 75 mg, from 40 mg to 100 mg, from 40 mg to 125 mg, from 40 mg to 150 mg, from 40 mg to 175 mg, from 40 mg to 200 mg, from 40 mg to 225 mg, from 40 mg to 250 mg, from 50 mg to 75 mg, from 50 mg to 100 mg, from 50 mg to 125 mg, from 50 mg to 150 mg, from 50 mg to 175 mg, from 50 mg to 200 mg, from 50 mg to 225 mg, from 50 mg to 250 mg, from 60 mg to 75 mg, from 60 mg to 100 mg, from 60 mg to 125 mg, from 60 mg to 150 mg, from 60 mg to 175 mg, from 60 mg to 200 mg, from 60 mg to 225 mg, from 60 mg to 250 mg, from 70 mg to 75 mg, from 70 mg to 100 mg, from 70 mg to 125 mg, from 70 mg to 150 mg, from 70 mg to 175 mg, from 70 mg to 200 mg, from 70 mg to 225 mg, from 70 mg to 250 mg, from 80 mg to 100 mg, from 80 mg to 125 mg, from 80 mg to 150 mg, from 80 mg to 175 mg, from 80 mg to 200 mg, from 80 mg to 225 mg, from 80 mg to 250 mg, from 90 mg to 100 mg, from 90 mg to 125 mg, from 90 mg to 150 mg, from 90 mg to 175 mg, from 90 mg to 200 mg, from 90 mg to 225 mg, from 90 mg to 250 mg, from 100 mg to 125 mg, from 100 mg to 150 mg, from 100 mg to 175 mg, from 100 mg to 200 mg, from 100 mg to 225 mg, and from 100 mg to 250 mg). These unit dosage forms can be administered to achieve any daily amount described herein, such as by administering one to five times daily (e.g., one, two, three, four, or five times daily).

Unit Dosage Forms

For use as treatment of human and animal subjects, compound 1, compound 2, or a salt thereof, can be formulated as pharmaceutical or veterinary compositions. Depending on the subject to be treated, the mode of administration, and the type of treatment desired (e.g., prevention, prophylaxis, or therapy) the compounds are formulated in ways consonant with these parameters. A summary of such techniques is found in Remington: *The Science and Practice of Pharmacy*, 21st Edition, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

Compound 1, compound 2, or a salt thereof, may be present in amounts totaling 1-95% by weight of the total weight of the composition. The composition including compound 1, compound 2, or a salt thereof, and a pharmaceutically acceptable matrix polymer may be provided in a dosage form that is suitable for oral administration. Alternatively, the unit dosage form of the invention includes substantially amorphous compound 1, compound 2, or a salt thereof, and a pharmaceutically acceptable excipient (e.g., fillers, diluents, lubricants, and/or glidants). Thus, the pharmaceutical composition may be in the form of, e.g., hard capsules (e.g., hard gelatin capsules or hard hydroxypropyl methylcellulose capsules), soft gelatin capsules, tablets, caplets, enteric coated tablets, chewable tablets, enteric coated hard gelatin capsules, enteric coated soft gelatin capsules, minicapsules, lozenges, films, strips, gelcaps, dragees, suspensions, syrups, or sprinkles.

The compositions may be formulated according to conventional pharmaceutical practice.

In particular embodiments, compound 1, compound 2, or a salt thereof, and a matrix polymer are included in a capsule or compressed into a tablet. Compound 1, compound 2, or a salt thereof, in combination with a matrix polymer can be in any form, such as a semi-solid suspension, a solid suspension, a homogenous melt, solid particles, or semi-solid particles. The form of the compound 1, compound 2, or a salt thereof, can be determined based on dose. For example, a capsule filled with a solid dispersion can be used for approximately 10-50% drug loading.

Exemplary unit dosage forms are hard capsules (e.g., hard gelatin capsules or hard hydroxypropyl methylcellulose capsules) and soft gelatin capsules. When soft gelatin capsules are used, it is preferred that when a composition contains a polyethylene glycol, the composition of the soft gelatin capsule shell contains a humectant, for example, sorbitol, to prevent brittleness of the soft gelatin capsule.

Utility and Treatment of Conditions

Conditions that can be treated using the compositions or formulations described herein include pain (e.g., chronic or acute pain), epilepsy, Alzheimer's disease, Parkinson's disease, diabetes, cancer, sleep disorders, obesity, mood disorders, psychosis such as schizophrenia, tinnitus, amyotrophic lateral sclerosis, glaucoma, ischaemia, spasticity disorders, obsessive compulsive disorder, restless leg syndrome, Tourette syndrome, overactive bladder, renal disease, neuroprotection, and addiction. For example, the condition can be pain (e.g., neuropathic pain or post-surgery pain), epilepsy, migraine, Parkinson's disease, depression, schizophrenia, psychosis, or tinnitus.

Epilepsy as used herein includes but is not limited to partial seizures such as temporal lobe epilepsy, absence seizures, generalized seizures, and tonic/clonic seizures.

Cancer as used herein includes but is not limited to breast carcinoma, neuroblastoma, retinoblastoma, glioma, prostate carcinoma, esophageal carcinoma, fibrosarcoma, colorectal carcinoma, pheochromocytoma, adenocarcinoma, insulinoma, lung carcinoma, melanoma, and ovarian cancer.

Acute pain as used herein includes but is not limited to nociceptive pain and post-operative pain. Chronic pain includes, but is not limited to, neuropathic pain, peripheral neuropathic pain such as post-herpetic neuralgia, diabetic neuropathic pain, neuropathic cancer pain, HIV-associated neuropathy, erythromelalgia, failed back-surgery syndrome, trigeminal neuralgia, and phantom limb pain; central neuropathic pain such as multiple sclerosis related pain, Parkinson disease related pain, post-stroke pain, post-traumatic spinal cord injury pain, lumbosacral radiculopathy, cervical radiculopathy, brachial radiculopathy, and pain in dementia; musculoskeletal pain such as osteoarthritic pain and fibromyalgia syndrome; inflammatory pain such as rheumatoid arthritis, juvenile idiopathic arthritis, ankylosing spondylitis, psoriatic arthritis, inflammatory bowel disease, primary dysmenorrhea, and endometriosis; headache such as migraine, cluster headache, tension headache syndrome, facial pain, and headache caused by other diseases; visceral pain such as interstitial cystitis, irritable bowel syndrome, and chronic pelvic pain syndrome; and mixed pain such as lower back pain, neck and shoulder pain, burning mouth syndrome, and complex regional pain syndrome.

In treating osteoarthritic pain, joint mobility can also improve as the underlying chronic pain is reduced. Thus, use of compositions and formulations of the present invention to treat osteoarthritic pain includes use of such compositions or formulations to improve joint mobility in patients suffering from osteoarthritis or other condition presenting with decreased joint mobility.

The compositions and formulations described herein can be tested for efficacy in any standard animal model of pain. Various models test the sensitivity of normal animals to intense or noxious stimuli (physiological or nociceptive pain). These tests include responses to thermal, mechanical, or chemical stimuli. Thermal stimuli usually involve the application of hot stimuli (typically varying between 42-55° C.) including, for example: radiant heat to the tail (the tail flick test), radiant heat to the plantar surface of the hindpaw (the Hargreaves test), the hotplate test, and immersion of the hindpaw or tail into hot water. Immersion in cold water, acetone evaporation, or cold plate tests may also be used to test cold pain responsiveness. Tests involving mechanical stimuli typically measure the threshold for eliciting a withdrawal reflex of the hindpaw to graded strength monofilament von Frey hairs or to a sustained pressure stimulus to a paw (e.g., the Ugo Basile analgesiometer). The duration of a response to a standard pinprick may also be measured. When using a chemical stimulus, the response to the application or injection of a chemical irritant (e.g., capsaicin, mustard oil, bradykinin, ATP, formalin, or acetic acid) to the skin, muscle joints, or internal organs (e.g., bladder or peritoneum) is measured.

In addition, various tests assess pain sensitization by measuring changes in the excitability of the peripheral or central components of the pain neural pathway. In this regard, peripheral sensitization (i.e., changes in the threshold and responsiveness of high threshold nociceptors) can be induced by repeated heat stimuli as well as the application or injection of sensitizing chemicals (e.g., prostaglandins, bradykinin, histamine, serotonin, capsaicin, or mustard oil). Central sensitization (i.e., changes in the excitability of neurons in the central nervous system induced by activity in peripheral pain fibers) can be induced by noxious stimuli (e.g., heat), chemical stimuli (e.g., injection or application of chemical irritants), or electrical activation of sensory fibers.

Various pain tests developed to measure the effect of peripheral inflammation on pain sensitivity can also be used to study the efficacy of the compositions (Stein et al., *Pharmacol. Biochem. Behav.* 31: 445-451, 1988; Woolf et al., *Neurosci.* 62:327-331, 1994). Additionally, various tests assess peripheral neuropathic pain using lesions of the peripheral nervous system. One such example is the "axotomy pain model" (Watson, *J. Physiol.* 231:41, 1973). Other similar tests include the SNL test which involves the ligation of a spinal segmental nerve (Kim and Chung, *Pain* 50: 355, 1992), the Seltzer model involving partial nerve injury (Seltzer, *Pain* 43: 205-18, 1990), the spared nerve injury (SNI) model (Decosterd and Woolf, *Pain* 87:149, 2000), chronic constriction injury (CCI) model (Bennett, *Muscle Nerve* 16:1040, 1993), tests involving toxic neuropathies such as diabetes (streptozocin model), pyridoxine neuropathy, taxol, vincristine, and other antineoplastic agent-induced neuropathies, tests involving ischemia to a nerve, peripheral neuritis models (e.g., CFA applied peri-neurally), models of postherpetic neuralgia using HSV infection, and compression models.

In all of the above tests, outcome measures may be assessed, for example, according to behavior, electrophysiology, neurochemistry, or imaging techniques to detect changes in neural activity.

EXAMPLES

Example 1

In Vitro Absorption of Compound 1

Absorption of particular drugs may be limited by biological factors, such as reduced cellular permeability in the intestine. Many cellular mechanisms can influence permeability, such as reduced passive paracellular and transcellular transport or increased active export by the efflux transporter protein P-glycoprotein. Thus, the use of self-emulsifying carriers may not be beneficial for drugs having limited cellular permeability, where methods to increase the solubilization of a drug may not increase its permeability in the gastrointestinal tract. Experiments were conducted to assess the apparent intestinal permeability of compound 1 using a Caco-2 cell model. Overall, the data herein suggest that compound 1 is not limited by permeability in the intestine, and formulations that promote delivery of compound 1 to the gastrointestinal tract may reduce food effects or increase bioavailability.

Briefly, Caco-2 cells were used as an in vitro model for predicting absorption through the intestinal epithelium. Confluent monolayers of Caco-2 cells were grown on collagen-coated, microporous, polycarbonate membranes (12-well Costar Transwell® plates) that are placed between two chambers. The apical side of the monolayer was exposed to the buffer solution in a first chamber, but the basolateral side of the monolayer adhered to microporous membranes fluidically connected to a second chamber. The dosing solution was added to the first chamber for measurements in the apical-to-basolateral direction (A-to-B) and to the second chamber for measurements in the basolateral-to-apical direction (B-to-A). Accordingly, for A-to-B measurements, the first chamber was the receiver chamber and the second chamber was the donor chamber; for B-to-A measurements, the first chamber was the donor chamber and the second chamber was the receiver chamber. The permeability assay buffer was Hanks Balanced Salt Solution containing 10 mM HEPES and 15 mM glucose at a pH of 7.4. The buffer in the receiver chamber also contained 1% bovine serum albumin. The dosing solution concentration was 1 µM of compound 1 in the assay buffer. All donor chambers were first pre-incubated for five minutes with dosing solution to attempt to saturate any non-specific binding sites on the device with test compound. After five minutes, the solution was removed and replaced with fresh dosing solution, and time was recorded as 0. Cell monolayers were dosed on the apical side/first chamber (for A-to-B measurements) or basolateral side/second chamber (for B-to-A measurements) and incubated at 37° C. with 5% $CO_2$ in a humidified incubator. At 30 and 60 minutes, aliquots were taken from the receiver chambers and replaced with fresh assay buffer. Samples were taken from the donor chamber at 0 and 60 minutes. Each experiment was performed in triplicate.

The apparent permeability ($P_{app}$), percent recovery, and efflux ratio were calculated as follows:

$$P_{apps}[\text{cm s}^{-1}] = \frac{dC_r}{dt} \times \frac{V_r}{A \times C_0},$$

$$\text{Percent recovery } [\%] = 100 \times \frac{(V_r \times C_{r,final}) + (V_d \times C_{d,final})}{V_d \times C_N}, \text{ and}$$

$$\text{Efflux ratio} = \frac{P_{app}(B\text{-to-}A)}{P_{app}(A\text{-to-}B)},$$

where $$\frac{dC_r}{dt} [\mu M \, s^{-1}]$$

is the slope of the cumulative concentration in the receiver chamber as a function of time; $V_r$ [cm$^3$] is the volume of the receiver chamber; $V_d$ [cm$^3$] is the volume of the donor chamber; A [cm$^2$] is the area of the cell monolayer, which is estimated to be about 1.13 cm$^2$ for the 12-well Costar Transwell® plates; $C_0$ [µM] is the measured concentration in the donor chamber at t=0 hours; $C_N$ [µM] is the nominal concentration of the dosing solution; $C_{r,final}$ [µM] is the cumulative concentration in the receiver chamber at the end of the incubation period; and $C_{d,final}$ [µM] is the cumulative concentration in the donor chamber at the end of the incubation period.

Table 2 shows the apparent permeability for the apical-to-basolateral direction (A-to-B), the basolateral-to-apical direction (B-to-A), and cell-free condition. Compound 1 was classified as having a high permeability coefficient, due to an apparent permeability value $P_{app}$(A-to-B) more than 1.0× 10$^{-6}$ cm/s. Efflux of compound 1 was not considered significant, due to an efflux ratio of less than 3. Thus, absorption of compound 1 in humans is not expected to be permeability limited.

TABLE 2

| Direction | Initial Donor Conc. (µM) | Percent Recovery (%) | $P_{app}$ (10$^{-6}$ cm/s) | | | | Efflux Ratio ($P_{app}$ (B-to-A)/ $P_{app}$ (A-to-B)) |
| | | | R1 | R2 | R3 | Avg. | |
| --- | --- | --- | --- | --- | --- | --- | --- |
| A-to-B | 0.69 | 28 | 4.37 | 4.31 | 6.78 | 5.15 | 0.8 |
| B-to-A | 0.59 | 37 | 5.04 | 3.48 | 4.45 | 4.32 | |
| Cell-free | 0.68 | 54 | 1.71 | 2.21 | 1.69 | 1.87 | |

Example 2

Solubility of Solid Dispersion Formulations in Gastric and Intestinal Media Eight solid dispersion formulations were tested at 20% (w/w) loading of compound 1. As shown in FIG. 1A, unformulated compound 1 rapidly precipitated from the FaSSIF media following exposure to gastric media.

Various formulations were tested to reduce precipitation. As shown in FIGS. 1A-1H, solubility was measured for the following formulations: carboxymethylethyl cellulose (CMEC, FIG. 1A), cellulose acetate phthalate (CAP, FIG. 1B), hydroxypropylmethyl cellulose acetate succinate M grade (HPMCAS-M, FIG. 1C), polyvinyl acetate phthalate (PVAP, FIG. 1D), methacrylic acid-methyl methacrylate copolymer (Eudragit® L 100, FIG. 1E), polyethylene glycol-polyvinylcaprolactam-polyvinylacetate copolymer (Soluplus®, FIG. 1F), hydroxypropylmethyl cellulose phthalate (HPMCP-H55, FIG. 1G), and polyvinylpyrrolidone vinylacetate copolymer (PVP-VA, FIG. 1H). At approximately 13 minutes, the media was transferred from gastric media (pH of 1.0) to Fasted State Simulated Intestinal Fluid media (FaSSIF media, pH of 6.5).

In all instances, the solid dispersion formulations provided improvements in solubility of compound 1. Dispersions having the highest $C_{max}$ included CMEC, CAP, HPMCAS-M, PVAP, and Eudragit® L 100 (FIGS. 1A-1E). Among these, PVAP had the fastest precipitation rate, and HPMCAS-M and Eudragit® L 100 had the slowest dissolution rates.

Further tests were conducted with different % loading of compound 1. Dissolution rates were measured for formulations have 35% (w/w) loading (FIGS. 2A-2C) and 50% (w/w) loading (FIGS. 3A-3D). CAP, HPMCAS-M, Eudragit® L 100, and PVAP were further analyzed for these tests. Generally, increased % loading exhibited lower free drug concentrations in the media (shown as open circles). Without wishing to be limited by theory, as % loading increases, the amount of matrix polymer needed to inhibit precipitation of compound 1 also increases. Overall, dissolution rates for 35% and 50% loading were comparable to those for 20% loading of the same polymers, and PVAP provided the highest $C_{max}$ and the most rapid precipitation.

Figure 4A:
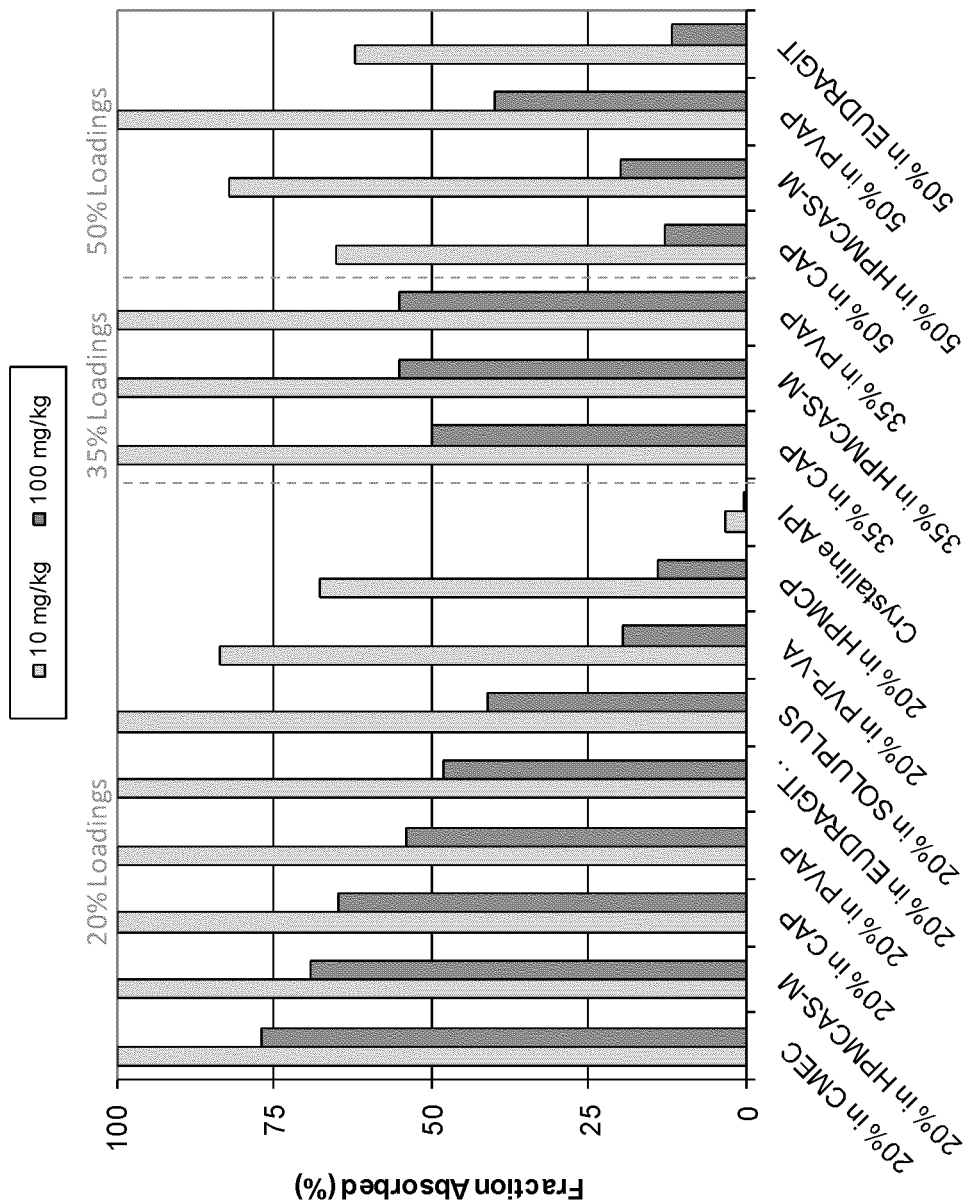
FIGS. 4A-4B are graphs showing results from computer modeling of fraction absorbed (FIG. 4A) and fed-fasted ratio (FIG. 4B) for 20%, 35%, and 50% (w/w) loading of compound 1. Data are shown for solid dispersion formulations of carboxymethylethyl cellulose (CMEC), hydroxypropylmethyl cellulose acetate succinate M grade (HPMCAS-M), cellulose acetate phthalate (CAP), polyvinyl acetate phthalate (PVAP), methacrylic acid-methyl methacrylate copolymer (Eudragit® L 100), polyethylene glycol-polyvinylcaprolactam-polyvinylacetate copolymer (Soluplus®), polyvinylpyrrolidone vinylacetate copolymer (PVP-VA), and hydroxypropylmethyl cellulose phthalate (HPMCP-H44), and for crystalline compound 1 (API).
Figure 4B:
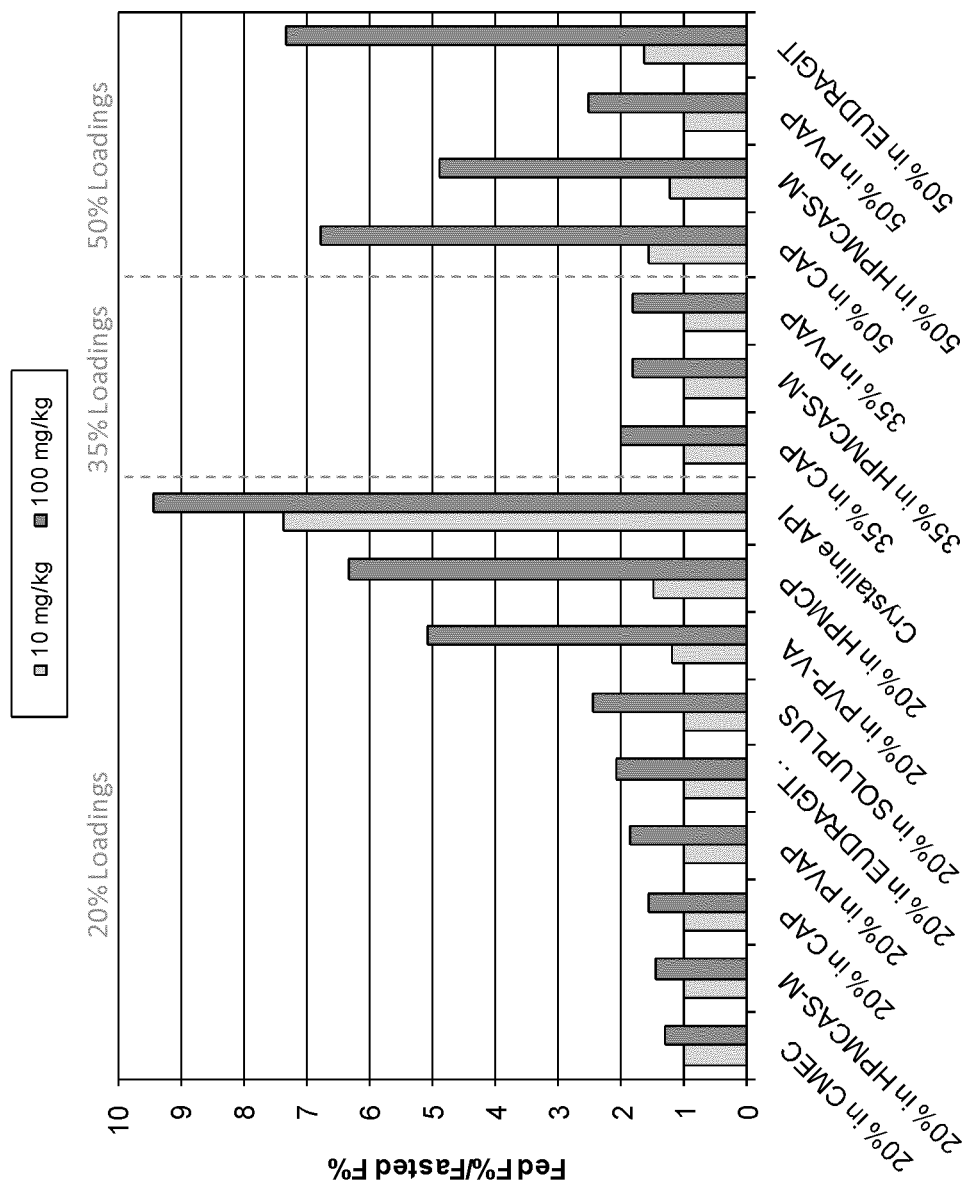

Physiological-based pharmacokinetic (PBPK) modeling (GastroPlus® v.6.1) was conducted to predict the in vivo fraction absorbed and the fed-fasted ratio at 10 mg/kg and 100 mg/kg doses. These predictive estimates are provided for fraction absorbed (FIG. 4A) and fed-fasted ratio (FIG. 4B) for 20%, 35%, and 50% (w/w) loading of compound 1. These data suggest enhanced absorption and reduced fed-fasted ratio for a range of formulations at 20% and 35% loading of compound 1.

Example 3

Solubility of Formulations 1 and 2

Figure 5A:
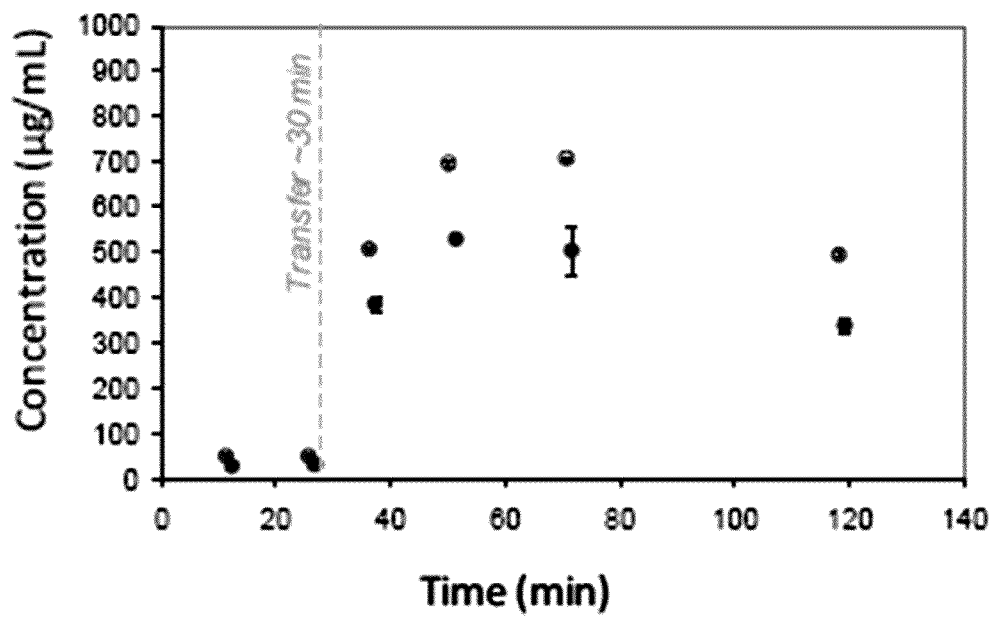
FIGS. 5A-5B are graphs showing the dissolution rate in gastric media for solid dispersion formulations having 20% (w/w) loading of compound 1 and a gastric-to-FaSSIF (pH 1.0-to-6.5) media transition at 30 minutes. The following solid dispersion formulations were tested: cellulose acetate phthalate (CAP, FIG. 5A) and hydroxypropylmethyl cellulose acetate succinate M grade (HPMCAS-M, FIG. 5B). The total drug species are represented by open circles with error bars, and the free drug species are represented by closed circles with error bars.
Figure 5B:
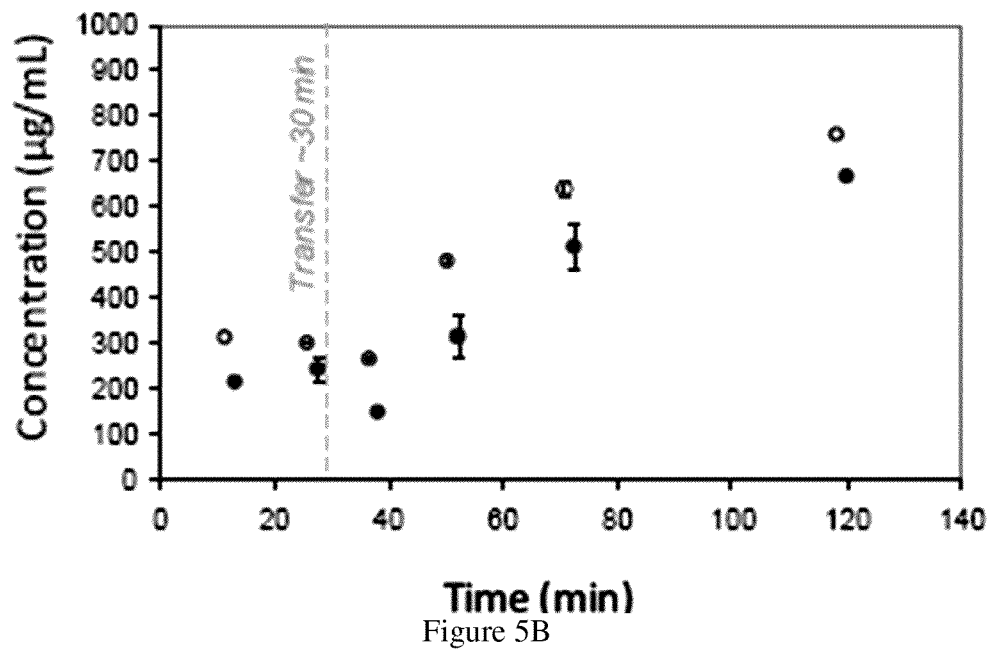

Based on the dissolution data provided herein, formulations for 20% (w/w) loading of formula 1 in CAP (formulation 1) and HPMCAS-M (formulation 2) were further tested with media transition times longer than 13 minutes to better represent human physiological gastric emptying times. At approximately 30 minutes, the media was transferred from gastric media (pH of 1.0) to Fasted State Simulated Intestinal Fluid media (FaSSIF media, pH of 6.5). FIGS. 5A-5B show that formulations 1 and 2 performed similarly to experiments performed at shorter times.

Example 4

Physical Characterization of Formulations

Figure 6:
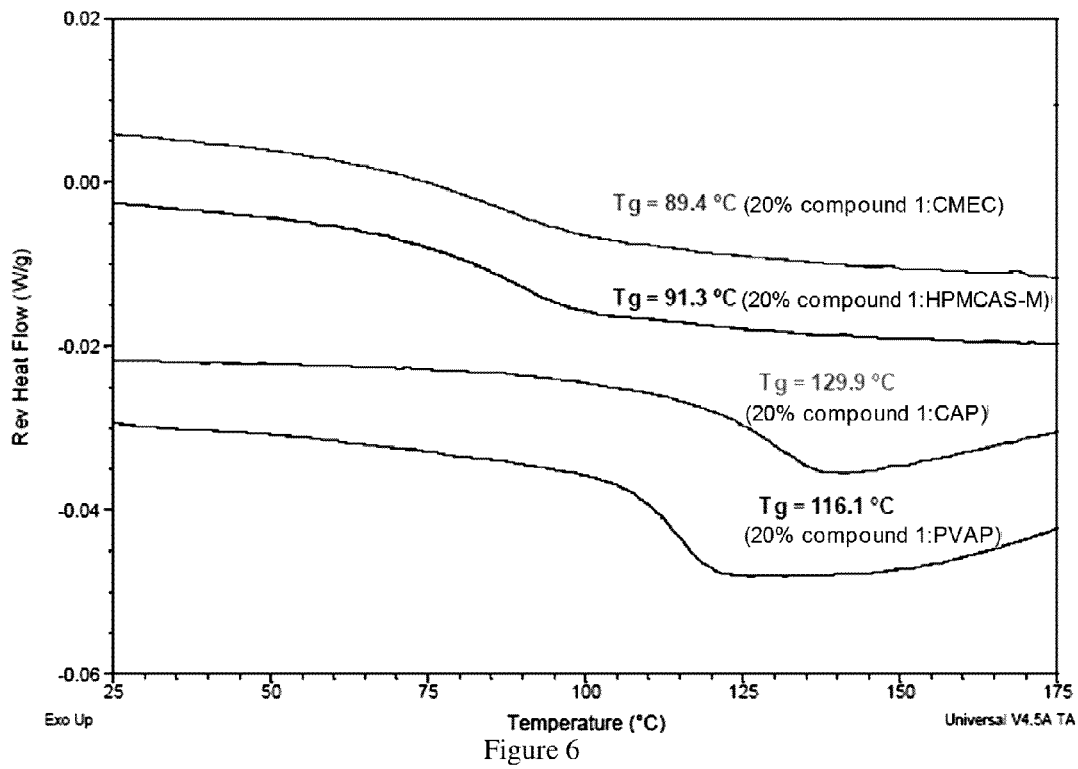
FIG. 6 is a graph showing modulated differential scanning calorimetry measurements at ambient relative humidity for solid dispersion formulations having 20% (w/w) loading of compound 1. Glass transition temperature $T_g$ is shown for formulations of carboxymethylethyl cellulose (CMEC), hydroxypropylmethyl cellulose acetate succinate M grade (HPMCAS-M), cellulose acetate phthalate (CAP), and polyvinyl acetate phthalate (PVAP).

Various solid dispersion formulations were tested using modulated differential scanning calorimetry (MDSC). MDSC measurements provide glass transition temperature $T_g$ values, which can be used to understand the molecular mobility of a drug within the dispersion. FIG. 6 shows the MDSC traces and $T_g$ values for CMEC, HPMCAS-M, CAP, and PVAP formulations having 20% (w/w) loading of compound 1. Data for Eudragit® L 100 are not shown, but $T_g$ is likely greater than 150° C. due to polymer degradation above this temperature. All recorded $T_g$ values were at least twice as high as compound 1 alone ($T_g$=41.6° C.). Lower $T_g$ values could indicate potential stability issues over long periods of time or at an increased temperature or pressure. Table 3 provides $T_g$ values for CAP (formulation 1), HPMCAS-M (formulation 2), and PVAP.

TABLE 3

| Formulation | Percentage (w/w) of compound 1 with polymer | $T_g$ (° C.) at ambient relative humidity | $T_g$ (° C.) at 75% relative humidity |
| --- | --- | --- | --- |
| CAP (formulation 1) | 20 | 130-132 | 83 |
| | 35 | 116 | N.D. |
| | 50 | N.D. | N.D. |
| HPMCAS-M (formulation 2) | 20 | 88-91 | 54 |
| | 35 | 63 | N.D. |
| | 50 | 55 | N.D. |
| PVAP | 20 | 116 | N.D. |
| | 35 | 106 | N.D. |
| | 50 | 90 | N.D. |

N.D.: not determined

Figure 7:
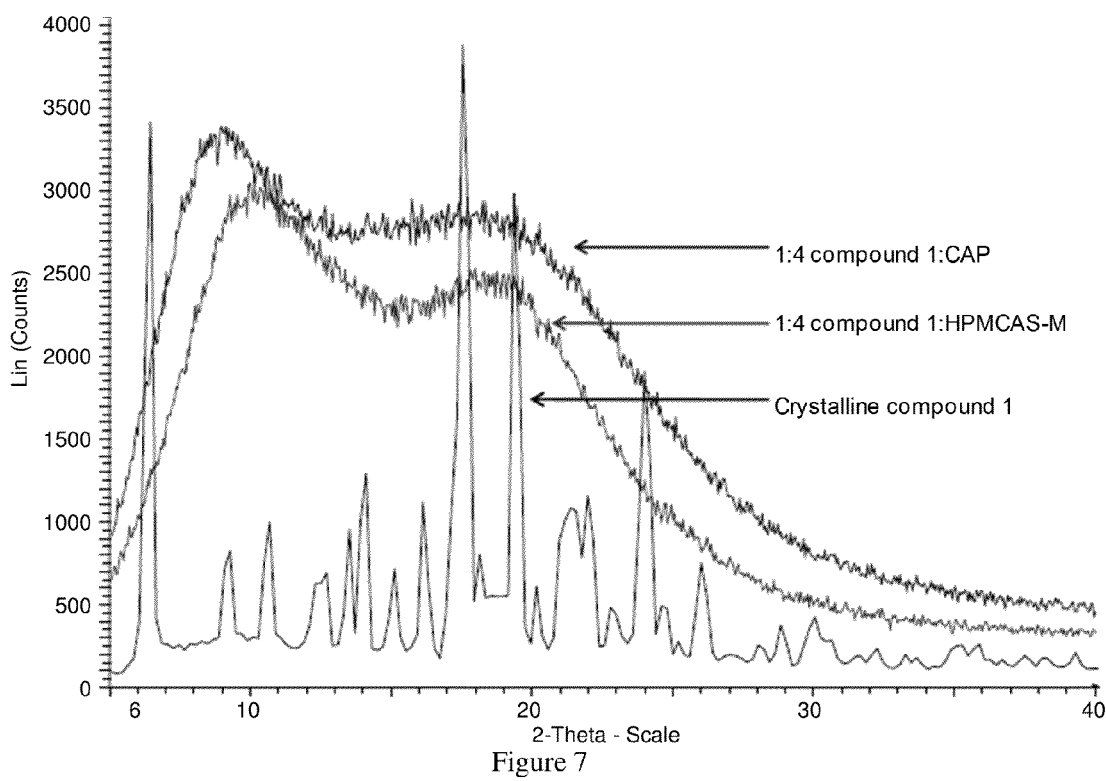
FIG. 7 is a graph showing powder x-ray diffraction measurements for crystalline compound 1 and solid dispersion formulations having 20% (w/w) loading of compound 1 with hydroxypropylmethyl cellulose acetate succinate M grade (HPMCAS-M) or cellulose acetate phthalate (CAP).

Formulations having CAP and HPMCAS-M were further analyzed using powder X-ray diffraction (PXRD). As shown in FIG. 7, no evidence of crystalline compound 1 was detected in either formulation 1 or 2.

Example 5

In Vivo Study in Rats

The pharmacokinetics of formulations having 20% (w/w) of compound 1 in matrix polymer were studied in rats. Table 4 provides a summary of the results for this in vivo study. Formulation 1 is 20% (w/w) of compound 1 in CAP. Formulation 2 is 20% (w/w) compound 1 in HPMCAS-M. Control indicates compound 1 in 0.5% Tween® 80 in 0.5% carboxy methylcellulose (CMC). Doses included 10 to 100 mg of compound 1 to kg of the subject (mg/kg).

TABLE 4

| Dose | Formulation | $C_{max}$ (ng/mL, mean) | $T_{max}$ (hr, mean) | $t_{1/2}$ (hr, mean) | $AUC_\infty$ (h*mg/mL, mean) | $AUC_{0\text{-}last}$ (h*mg/mL, mean) |
| --- | --- | --- | --- | --- | --- | --- |
| 10 mg/kg dose | Control | 89 | 3.33 | 1.54 | 503 | 466 |
| | 1 (CAP) | 82.0 | 6.67 | 1.99 | 540 | 385 |
| | 2 (HPMCAS-M) | 157 | 4.67 | 2.15 | 914 | 732 |
| 30 mg/kg dose | Control | 152 | 3.33 | 4.07 | 1262 | 831 |
| | 1 (CAP) | 392 | 3.33 | 2.07 | 2215 | 1925 |
| | 2 (HPMCAS-M) | 417 | 3.00 | 4.18 | 3970 | 2449 |
| 100 mg/kg dose | Control | 450 | 5.33 | 3.22 | 3461 | 2155 |
| | 1 (CAP) | 591 | 2.67 | 4.06 | 5179 | 3807 |
| | 2 (HPMCAS-M) | 714 | 3.00 | 2.64 | 4628 | 3667 |

Figure 8A:
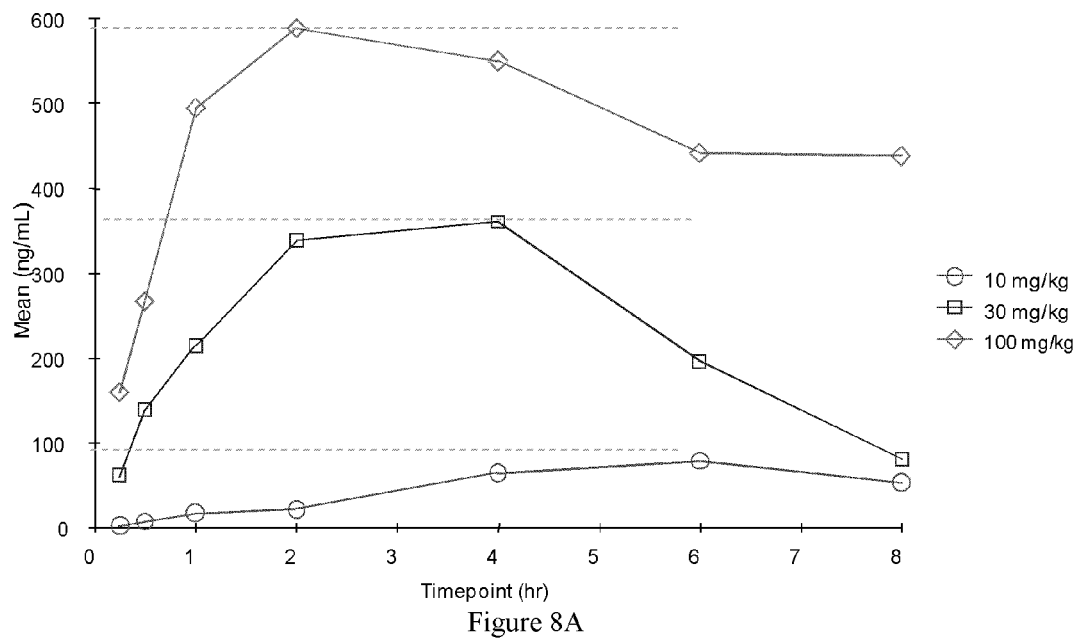
FIGS. 8A-8C are graphs showing mean concentration of compound 1 in plasma for various formulations in an in vivo studies in rats. Data are shown for formulation 1 having cellulose acetate phthalate (CAP) (FIG. 8A), formulation 2 having hydroxypropylmethyl cellulose acetate succinate M grade (HPMCAS-M) (FIG. 8B), and control (FIG. 8C) with doses of 10 mg/kg, 30 mg/kg, and 100 mg/kg.
Figure 8B:
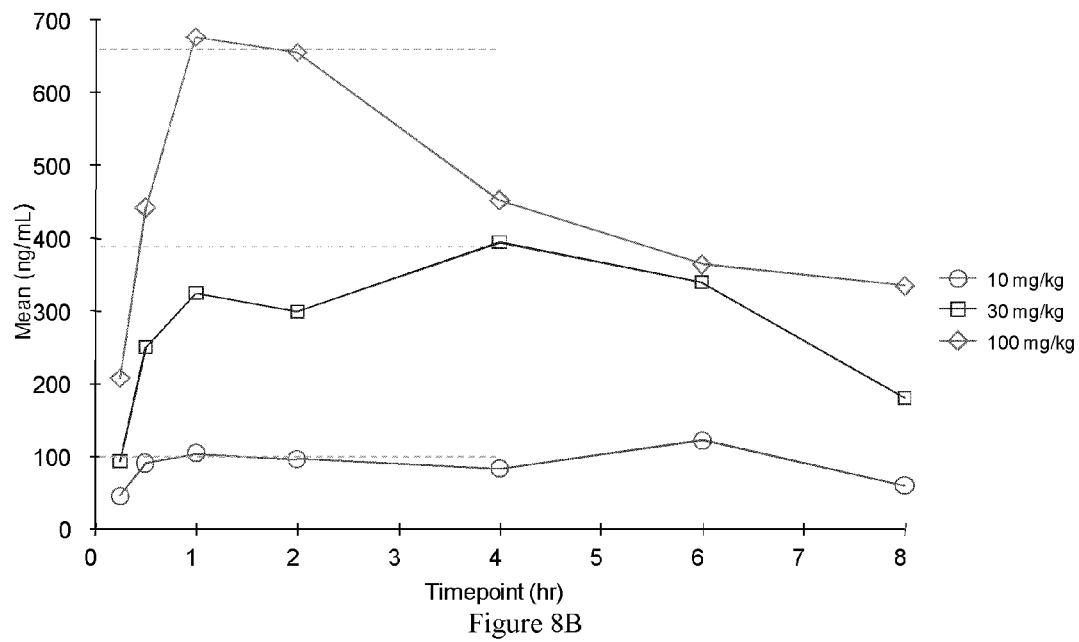
Figure 8C:
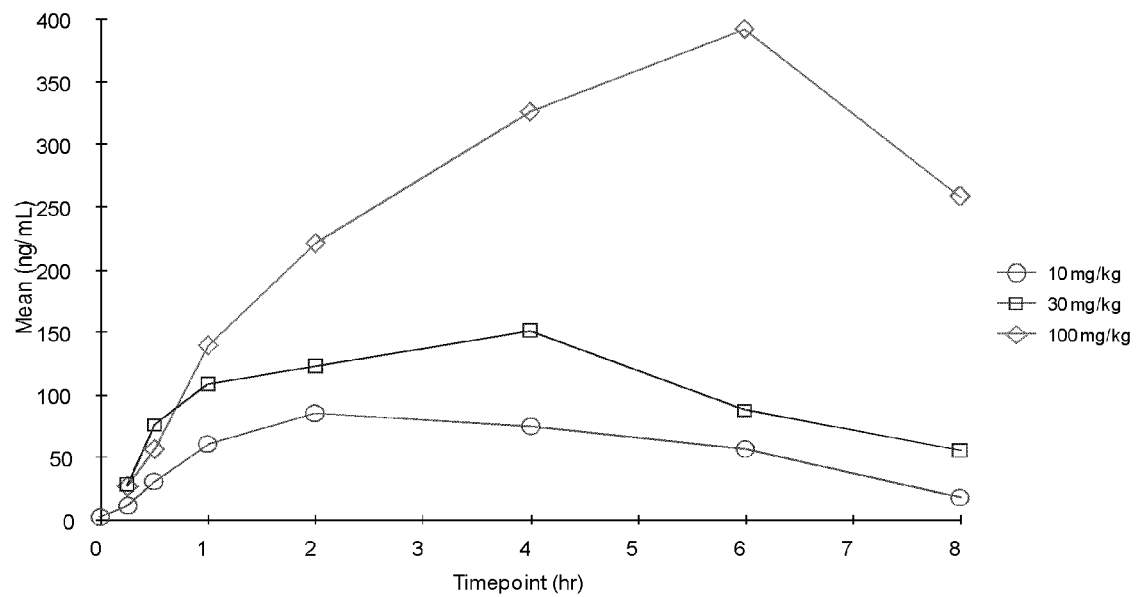
Figure 9A:
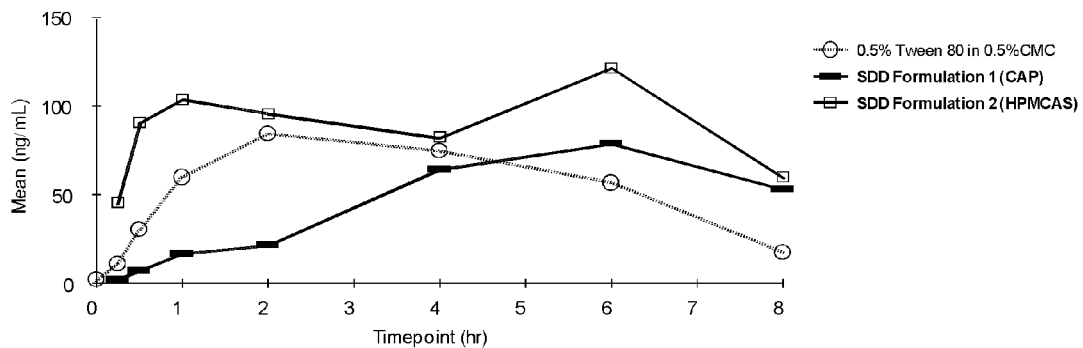
FIGS. 9A-9C are graphs showing mean concentration of compound 1 in plasma for various doses in an in vivo study in rats. Data are shown for formulations 1, 2, and control with doses of 10 mg/kg (FIG. 9A), 30 mg/kg (FIG. 9B), and 100 mg/kg (FIG. 9C).
Figure 9B:
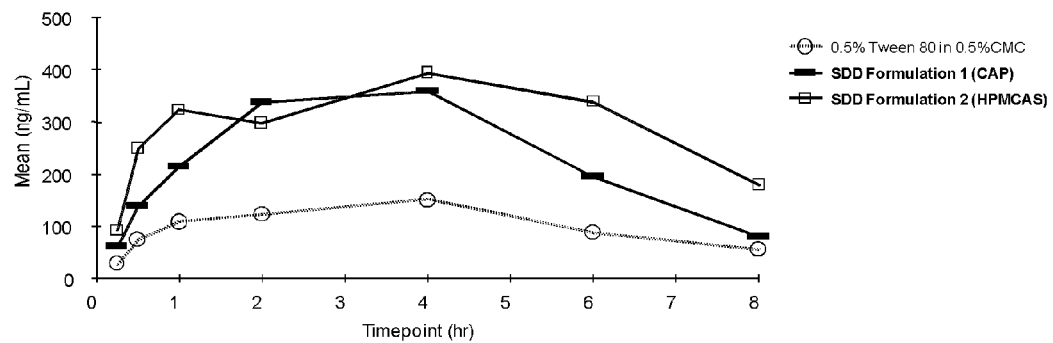
Figure 9C:
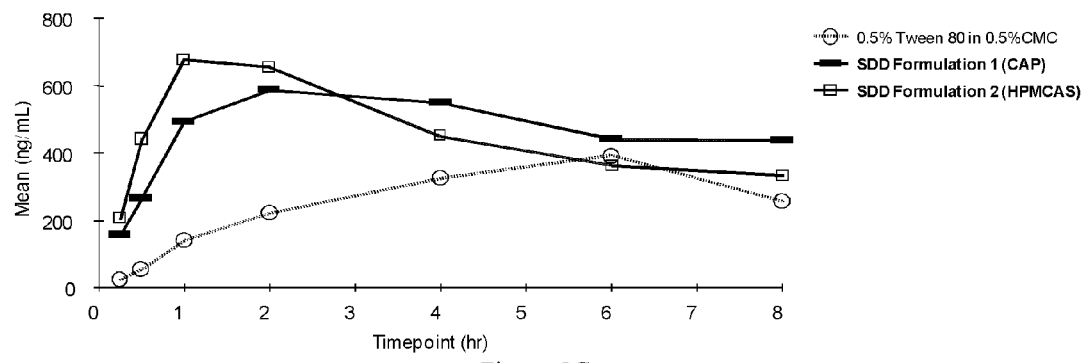

Data for each animal are provided for formulation 1 (Table 5 and FIG. 8A), formulation 2 (Table 6 and FIG. 8B), and control (Table 7 and FIG. 8C) for three doses. FIGS. 9A-9C provides data for these formulations for each dose. Overall, both formulations 1 and 2 showed enhanced oral bioavailability of compound 1, compared to control.

TABLE 5

| Dose of Formulation 1 (CAP) (20% (w/w)) | Animal | $C_{max}$ (ng/mL) | $T_{max}$ (hr) | $t_{1/2}$ (hr) | $AUC_\infty$ (h*ng/mL) | $AUC_{0-last}$ (h*ng/mL) |
|---|---|---|---|---|---|---|
| 10 mg/kg | 10 | 70.8 | 8.00 | NC | NC | 336 |
| | 11 | 72.1 | 6.00 | 1.75 | 451 | 369 |
| | 12 | 103 | 6.00 | 2.23 | 629 | 451 |
| | Mean | 82.0 | 6.67 | 1.99 | 540 | 385 |
| | SD | 18.2 | 1.15 | 0.341 | 126 | 59.5 |
| | SEM | 10.5 | 0.667 | 0.241 | 89.1 | 34.4 |
| 30 mg/kg | 13 | 361 | 2.00 | 1.74 | 1912 | 1778 |
| | 14 | 492 | 4.00 | 1.18 | 2191 | 2111 |
| | 15 | 324 | 4.00 | 3.28 | 2542 | 1885 |
| | Mean | 392 | 3.33 | 2.07 | 2215 | 1925 |
| | SD | 88.3 | 1.15 | 1.08 | 316 | 170 |
| | SEM | 51.0 | 0.667 | 0.626 | 182 | 97.9 |
| 100 mg/kg | 16 | 661 | 2.00 | 4.06 | 5179 | 3633 |
| | 17 | 540 | 4.00 | NC | NC | 3709 |
| | 18 | 572 | 2.00 | NC | NC | 4080 |
| | Mean | 591 | 2.67 | 4.06 | 5179 | 3807 |
| | SD | 62.7 | 1.15 | n/a | n/a | 239 |
| | SEM | 36.2 | 0.667 | n/a | n/a | 138 |

TABLE 6

| Dose of Formulation 2 (HPMCAS-M) (20% (w/w)) | Animal | $C_{max}$ (ng/mL) | $T_{max}$ (hr) | $t_{1/2}$ (hr) | $AUC_\infty$ (h*ng/mL) | $AUC_{0-last}$ (h*ng/mL) |
|---|---|---|---|---|---|---|
| 10 mg/kg | 19 | 119 | 6.00 | 2.09 | 690 | 505 |
| | 20 | 174 | 2.00 | 2.25 | 845 | 762 |
| | 21 | 178 | 6.00 | 2.10 | 1206 | 928 |
| | Mean | 157 | 4.67 | 2.15 | 914 | 732 |
| | SD | 33.0 | 2.31 | 0.0868 | 265 | 213 |
| | SEM | 19.0 | 1.33 | 0.0501 | 153 | 123 |
| 30 mg/kg | 22 | 342 | 1.00 | 2.10 | 2068 | 1845 |
| | 23 | 468 | 4.00 | 8.15 | 6620 | 2706 |
| | 24 | 440 | 4.00 | 2.27 | 3222 | 2795 |
| | Mean | 417 | 3.00 | 4.18 | 3970 | 2449 |
| | SD | 66.2 | 1.73 | 3.44 | 2366 | 525 |
| | SEM | 38.2 | 1.00 | 1.99 | 1366 | 303 |
| 100 mg/kg | 25 | 574 | 6.00 | 2.74 | 5112 | 3745 |
| | 26 | 893 | 2.00 | 2.55 | 4143 | 3479 |
| | 27 | 674 | 1.00 | NC | NC | 3778 |
| | Mean | 714 | 3.00 | 2.64 | 4628 | 3667 |
| | SD | 163 | 2.65 | 0.136 | 685 | 164 |
| | SEM | 94.2 | 1.53 | 0.0963 | 484 | 94.8 |

TABLE 7

| Dose of Control | Animal | $C_{max}$ (ng/mL) | $T_{max}$ (hr) | $t_{1/2}$ (hr) | $AUC_\infty$ (h*ng/mL) | $AUC_{0-last}$ (h*ng/mL) |
|---|---|---|---|---|---|---|
| 10 mg/kg | 1 | 96.7 | 6.00 | 0.858 | 558 | 534 |
| | 2 | 110 | 2.00 | 1.65 | 559 | 517 |
| | 3 | 60.6 | 2.00 | 2.13 | 391 | 346 |
| | Mean | 89 | 3.33 | 1.54 | 503 | 466 |
| | SD | 26 | 2.3 | 0.64 | 97.0 | 104 |
| | SEM | 15 | 1.3 | 0.37 | 56.0 | 60.0 |
| 30 mg/kg | 4 | 125 | 2.00 | 8.28 | 1888 | 845 |
| | 5 | 169 | 4.00 | 1.34 | 898 | 857 |
| | 6 | 162 | 4.00 | 2.59 | 998 | 790 |
| | Mean | 152 | 3.33 | 4.07 | 1262 | 831 |
| | SD | 23.6 | 1.15 | 3.70 | 545 | 35.3 |
| | SEM | 13.7 | 0.667 | 2.14 | 315 | 20.4 |
| 100 mg/kg | 1 | 434 | 4.00 | 2.88 | 2812 | 2121 |
| | 8 | 361 | 6.00 | 2.49 | 2637 | 1893 |
| | 9 | 554 | 6.00 | 4.29 | 4934 | 2453 |
| | Mean | 450 | 5.33 | 3.22 | 3461 | 2155 |
| | SD | 97.4 | 1.15 | 0.945 | 1279 | 282 |
| | SEM | 56.3 | 0.667 | 0.545 | 738 | 163 |

Example 6

In Vivo Study in Dogs

Figure 10:
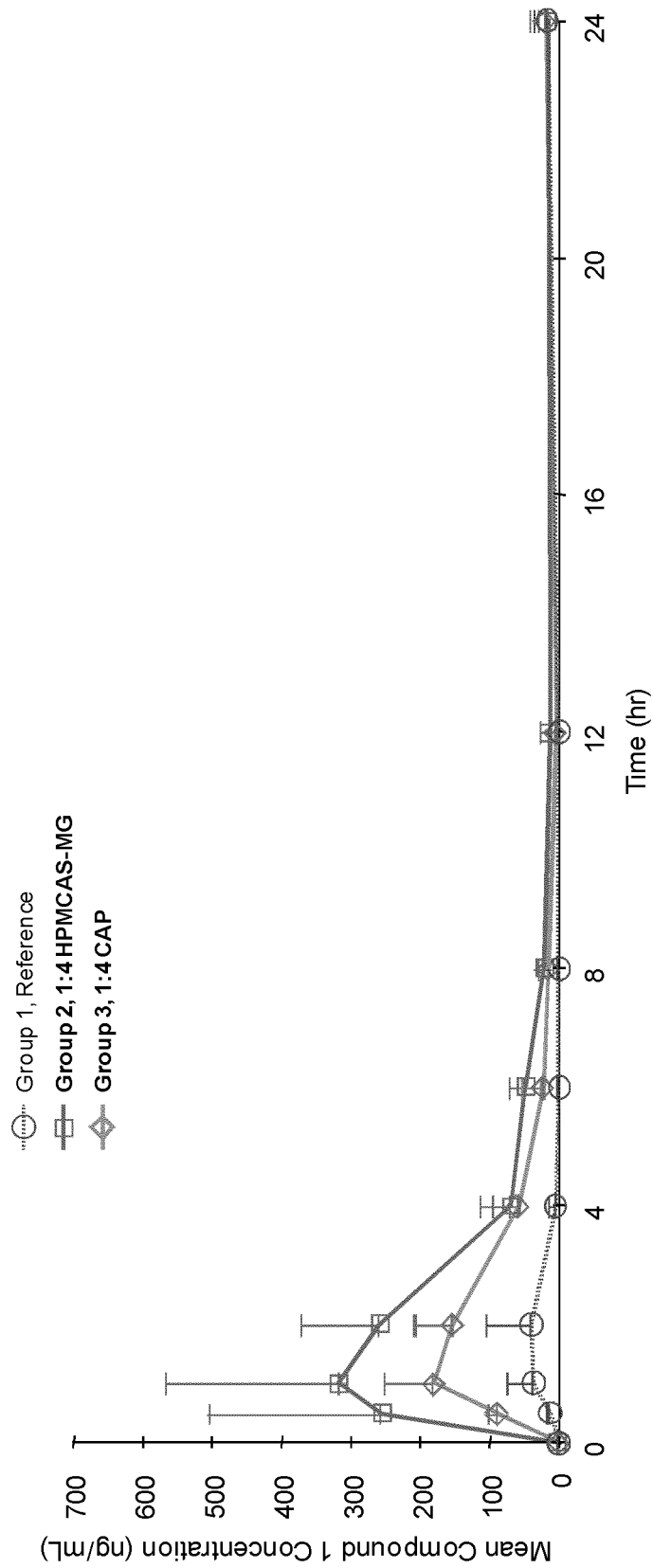
FIG. 10 is a graph showing mean concentration of compound 1 in plasma for various formulations in an in vivo study in dogs with a 10 mg/kg dose. Data are shown for 20% (w/w) compound 1 with hydroxypropylmethyl cellulose acetate succinate M grade (HPMCAS-MG, Group 2) or cellulose acetate phthalate (CAP, Group 3) and control (Group 1).

The pharmacokinetics of formulations 1 and 2 were studied in dogs using a dosage of 10 mg/kg (mg of compound 1/kg of subject). Table 8 provides a summary of the results for this in vivo study. Control indicates compound 1 HCl in 0.5% Tween 80 in 0.5% CMC. FIG. 10 shows enhanced oral bioavailability for formulations 1 and 2.

TABLE 8

| | Animal | Rsq | $T_{max}$ (hr) | $t_{1/2}$ (hr) | $C_{max}$ (ng/mL) | $AUC_{0-last}$ (hr*ng/mL) | $AUC_{0-24}$ (hr*ng/mL) | $AUC_\infty$ (hr*ng/mL) |
|---|---|---|---|---|---|---|---|---|
| Group 1 (control) | 1311019 | NC | 1 | NC | 14.4 | 7.82 | 15.0 | NC |
| | 1311108 | 0.03 | 2 | NR | 111 | 470 | 470 | NR |
| | 1457366 | NC | 1 | NC | 17.3 | 131 | 131 | NC |
| | Mean | 0.03 | 1.3 | NC | 47.6 | 203 | 205 | NC |
| | SD | NA | 0.6 | NA | 55 | 239 | 236 | NA |
| Group 2 (formulation 2 (HPMCAS-M)) | 1376382 | 0.99 | 1 | 8.9 | 603 | 1740 | 1740 | 1820 |
| | 1401603 | 0.25 | 1 | NR | 160 | 800 | 800 | NR |
| | 1408951 | 0.96 | 2 | 12.8 | 300 | 1230 | 1230 | 1480 |
| | Mean | 0.73 | 1.3 | 10.9 | 354 | 1260 | 1260 | 1650 |
| | SD | 0.41 | 0.6 | NA | 226 | 472 | 472 | NA |

TABLE 8-continued

| | Animal | Rsq | $T_{max}$ (hr) | $t_{1/2}$ (hr) | $C_{max}$ (ng/mL) | $AUC_{0\text{-}last}$ (hr*ng/mL) | $AUC_{0\text{-}24}$ (hr*ng/mL) | $AUC_{\infty}$ (hr*ng/mL) |
|---|---|---|---|---|---|---|---|---|
| Group 3 | 1296265 | 0.88 | 1 | 1.5 | 169 | 384 | 399 | 400 |
| (formulation 1 | 1502906 | 0.14 | 2 | NR | 135 | 600 | 600 | NR |
| (CAP)) | 5955823 | 0.43 | 1 | NR | 254 | 1330 | 1330 | NR |
| | Mean | 0.48 | 1.3 | 1.5 | 186 | 773 | 777 | 400 |
| | SD | 0.37 | 0.6 | NA | 61.3 | 498 | 492 | NA |

NC = Not calculated by WinNonlin due to insufficient data points for elimination phase.
NR = Not reported, due to poor goodness-of-fit ($R^2 < 0.8$) for elimination phase.

In Table 8 above, the $AUC_{0\text{-}24}$ was about six times greater for Group 2 (HPMCAS) and more than three times greater for Group 3 (CAP), as compared to Group 1 (control).

Example 7

Phase 1 (Part 1) Study in Healthy Human Subjects

The pharmacokinetics of a spray dried dispersion (SDD) formulation having HPMCAS were studied in healthy, human subjects using an oral dosage of 225 mg of compound 1 (three 75-mg capsules).

Compound 1 (free base) was supplied in #00 white opaque hard gelatin shell capsules. Each capsule contained 75 mg of compound 1 (free base) in hypromellose acetate succinate (HPMCAS-MG) as a spray dried dispersion, which was dry blended with lactose, microcrystalline cellulose, sodium lauryl sulphate, colloidal silicon dioxide, croscarmellose sodium, and magnesium stearate. The spray dried dispersion was prepared by using a solution of compound 1 with hypromellose acetate succinate, grade MG (HPMCAS-MG), with acetone as the spray drying solvent. The quantitative composition of these SDD capsules is shown in Table 9.

TABLE 9

| Component | Function | Standard | Quantity per Capsule (mg) |
|---|---|---|---|
| compound 1 (free base) | API | C of A | 75.00 |
| Hypromellose acetate succinate Type MG | Polymer component of the solid dispersion | Ph. Eur., NF, JP | 300.00 |
| Lactose monohydrate | Binder-Filler | Ph. Eur., NF, JP | 38.24 |
| Microcrystalline cellulose | Binder-Filler | Ph. Eur., NF, JP | 78.24 |
| Croscarmellose sodium | Disintegrant | Ph. Eur., NF, JP | 17.00 |
| Sodium lauryl sulphate | Wetting agent | Ph. Eur., NF, JP | 4.24 |
| Colloidal silicon dioxide | Flow aid/Glidant | NF | 2.14 |
| Magnesium stearate | Lubricant | Ph. Eur., NF, JP | 2.14 |
| Capsule Shell, hard gelatin white opaque size 00 | Dosage form | | na |
| | | Total Fill Weight: | 517.0 |

Abbreviations:
API = Active Pharmaceutical Ingredient;
C of A—Certificate of Analysis;
Ph. Eur. = European Pharmacopoeia;
NF = National Formulary;
JP = Japanese Pharmacopeia This single-center, open-label, crossover design study was conducted to determine the relative bioavailability, safety, and tolerability of the oral, SDD formulation under fasted and fed conditions in healthy subjects. The study comprised of an up to 21-day screening period, two 4-day inpatient clinic stays, and 35-days outpatient follow-up period. Sixteen subjects were randomized to the fed state or fasted state.

On Day 1 in Period 1, subjects received capsules either in the fasted state (defined as no food consumption for 10 hours and no water for 2 hours prior to oral dosing) or the fed state (defined as consumption of a high-fat meal 30 minutes prior to oral dosing and must completely consume the meal before taking the capsules). Subjects were administered 225 mg of compound 1 in capsules. Immediately prior to dosing, vital signs were measured, a 12-lead ECG was obtained, and a pharmacokinetics (PK) blood sample was obtained. Subjects were then administered 225 mg of compound 1. Blood samples for PK determinations were obtained at 0.5, 1, 1.25, 1.5, 1.75, 2, 2.5, 3, 4, 5, 6, 8, 10, 12, and 16 hours post-oral dose; vital signs and 12-lead ECGs were obtained at 3, 4, and 5 hours post-dose; and any concomitant medications and adverse events (AE) were recorded.

During Days 1-4 (inpatient period) and Days 5-6 (outpatient period) in Period 1, blood samples for PK determinations, vital signs, and 12-lead ECGs were obtained at various time points; and adverse events (AE) were recorded. In particular, blood samples for PK determinations were obtained at 24 and 36 hours post-dose on Period 1/Day 2, at 48 and 60 hours post-dose on Period 1/Day 3, and at 72 hours post-dose on Period 1/Day 4. After completion of all of the Period 1/Day 4 assessments, the subjects were discharged from the clinical testing facility. Subjects reported back to the clinical testing facility on the mornings of Period 1/Days 5 and 6 for collection of PK blood samples at 96 hours (Period 1/Day 5) and 120 hours (Period 1/Day 6) post-dose.

After a one week washout period, subjects who received capsules in the fed state in Period 1 then received capsules in the fasted state in Period 2 (defined as no food consumption for 10 hours and no water for 2 hours preceding oral dosing); and subjects who received capsules in the fasted state in Period 1 received capsules in the fed state in Period 2.

A PK blood sample was taken at 168 hours after the first oral dose of study drug in Period 1; this sample, which was drawn immediately before the subject takes the 225-mg oral dose on the morning of Period 2/Day 1, was used as the pre-dose sample for Period 2. After collection of the pre-dose PK blood sample, subjects took a single oral dose of 225 mg of compound 1 (free base). Blood samples for PK determinations were obtained at 0.5, 1, 1.25, 1.5, 1.75, 2, 2.5, 3, 4, 5, 6, 8, 10, 12, and 16 hours post-oral dose; vital signs and 12-lead ECGs were obtained at 3, 4, and 5 hours post-oral dose; and any concomitant medications and AEs were recorded.

During Days 1-4 (inpatient period) in Period 2, blood samples for PK determinations, vital signs, and 12-lead ECGs were obtained at various time points; and adverse events (AE) were recorded. In particular, blood samples for PK determinations were obtained at 24 and 36 hours post-oral dose on Period 2/Day 2, at 48 and 60 hours post-dose on Period 2/Day 3, and at 72 hours post-oral dose on Period 2/Day 4. After completion of all of the Period 2/Day 4 assessments, the subjects were discharged from the clinical testing facility. Subjects returned to the clinical testing facility in the fasted state for an end of study (EOS) visit on Period 2/Day 36 or at the time of premature termination from the study. A fasting blood sample for PK determinations (840 hours post-oral dosing) and fasting blood and urine samples for safety laboratory determinations were obtained, vital signs were measured, and a physical examination was performed. A pregnancy test (β-hCG) was performed for female subjects.

For the data in Table 10, PK blood samples were collected to 168 hours for Period 1 and to 840 hours for Period 2. Table 10 shows the effect of Period 1 versus Period 2 on the estimation of terminal half-life.

TABLE 10

| | Half-Life (hr) | | |
|---|---|---|---|
| Subject | Period 1 | Period 2 | Ratio |
| 3001 | 130 | 316 | 41% |
| 3002 | 99 | 306 | 32% |
| 3003 | 199 | 296 | 67% |
| 3004 | 126 | 178 | 71% |
| 3005 | 72 | 388 | 19% |
| 3006 | 129 | 493 | 26% |
| 3007 | 265 | 220 | 121% |
| 3008 | 115 | 357 | 32% |
| 3009 | 100 | 309 | 33% |
| 3010 | 98 | 186 | 53% |
| 3011 | 111 | 282 | 39% |
| 3012 | 122 | 402 | 30% |
| 3013 | 79 | 231 | 34% |
| 3014 | 86 | 207 | 41% |
| 3015 | 97 | 377 | 26% |
| 3016 | 116 | 370 | 31% |
| Mean | 122 | 307 | 40% |
| CV % | 40% | 29% | 138% |

For the data in Table 11, corrected $AUC_{0-\infty}$, $C_{max}$, and $T_{max}$ values are provided for all samples in Period 1 and in Period 2. Table 11 shows the effect of food on the time to reach maximum concentration ($T_{max}$), as well as $AUC_{0-\infty}$ and $C_{max}$ values that have been corrected for carry-over effect and the truncated observation period of Period 2. Carry-over effects were observed in Period 2, likely due to incomplete washout.

TABLE 11*

| | $AUC_{0-\infty}$ (hr*ng/mL) | | | $C_{max}$ (ng/mL) | | | $T_{max}$ (hr) | | |
|---|---|---|---|---|---|---|---|---|---|
| Subject | Fasted | Fed | Fasted Fed | Fasted | Fed | Fasted Fed | Fasted | Fed | Fed – Fasted |
| 3001 | 5019 | 5298 | 95% | 528 | 608 | 87% | 1.3 | 5.0 | 3.7 |
| 3002 | 5544 | 10031 | 55% | 916 | 649 | 141% | 2.5 | 5.0 | 2.5 |
| 3003 | 7399 | 11462 | 65% | 431 | 519 | 83% | 10.0 | 6.0 | -4.0 |
| 3004 | 6296 | 7591 | 83% | 685 | 823 | 83% | 2.0 | 4.0 | 2.0 |
| 3005 | 6841 | 14742 | 46% | 806 | 1054 | 76% | 5.0 | 5.0 | 0.0 |
| 3006 | 5161 | 4381 | 118% | 563 | 328 | 172% | 2.5 | 8.0 | 5.5 |
| 3007 | 6210 | 8572 | 72% | 250 | 915 | 27% | 4.0 | 5.0 | 1.0 |
| 3008 | 2634 | 7282 | 36% | 423 | 591 | 72% | 1.8 | 6.0 | 4.2 |
| 3009 | 4099 | 8667 | 47% | 530 | 806 | 66% | 3.0 | 6.0 | 3.0 |
| 3010 | 5854 | 6730 | 87% | 473 | 449 | 105% | 1.3 | 6.0 | 4.7 |
| 3011 | 3432 | 8157 | 42% | 372 | 882 | 42% | 3.0 | 5.0 | 2.0 |
| 3012 | 4287 | 4419 | 97% | 595 | 613 | 97% | 1.5 | 5.0 | 3.5 |
| 3013 | 3604 | 7244 | 50% | 556 | 570 | 98% | 3.0 | 4.0 | 1.0 |
| 3014 | 4110 | 5884 | 70% | 719 | 787 | 91% | 1.5 | 6.0 | 4.5 |
| 3015 | 4180 | 10551 | 40% | 425 | 920 | 46% | 3.0 | 5.0 | 2.0 |
| 3016 | 5254 | 6346 | 83% | 576 | 531 | 109% | 1.8 | 5.0 | 3.2 |
| Mean | 4992 | 7960 | 68% | 553 | 690 | 87% | 3.0 | 5.4 | 2.4 |
| Median | n/a | n/a | n/a | n/a | n/a | n/a | 2.5 | 5.0 | 2.8 |
| % CV | 27% | 34% | 36% | 30% | 29% | 41% | 0.7 | 0.2 | 94% |
| Geometric Mean | 4820 | 7551 | 65% | 529 | 662 | 80% | 2.5 | 5.3 | n/a |

*AUC and $C_{max}$ values have been corrected for carry-over effect.

In Table 11 above, the ratio of mean $AUC_{0-\infty}$, $C_{max}$, and $T_{max}$ are 1.59, 1.25, and 1.8, respectively, for fed subjects to fasted subjects. Furthermore, administration of the SDD formulation produced a coefficient of variation in $AUC_{0-\infty}$ and $C_{max}$ of less than 35% in fasted subjects (i.e., 27% and 30%, respectively) and in fed subjects (i.e., 34% and 29%, respectively). Finally, administration of the SDD composition to fed and fasted subjects produced a coefficient of variation in $AUC_{\infty}$ of less than 40% (i.e., 36%) and in $C_{max}$ of less than 60% (i.e., 41%).

Figure 11A:
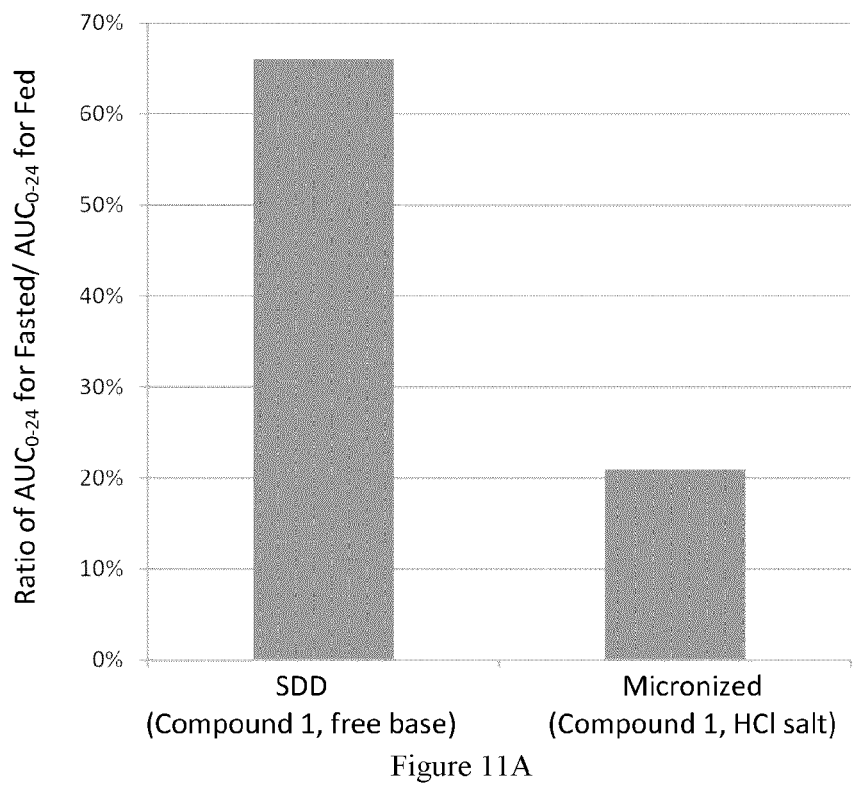
FIGS. 11A-11B are graphs comparing $AUC_{0-24}$ values for two formulations in fasted or fed conditions. Data are provided for compound 1 (free base) in an SDD formulation ("SDD") to compound 1 (HCl salt) in a micronized formulation ("Micronized").
Figure 11B:
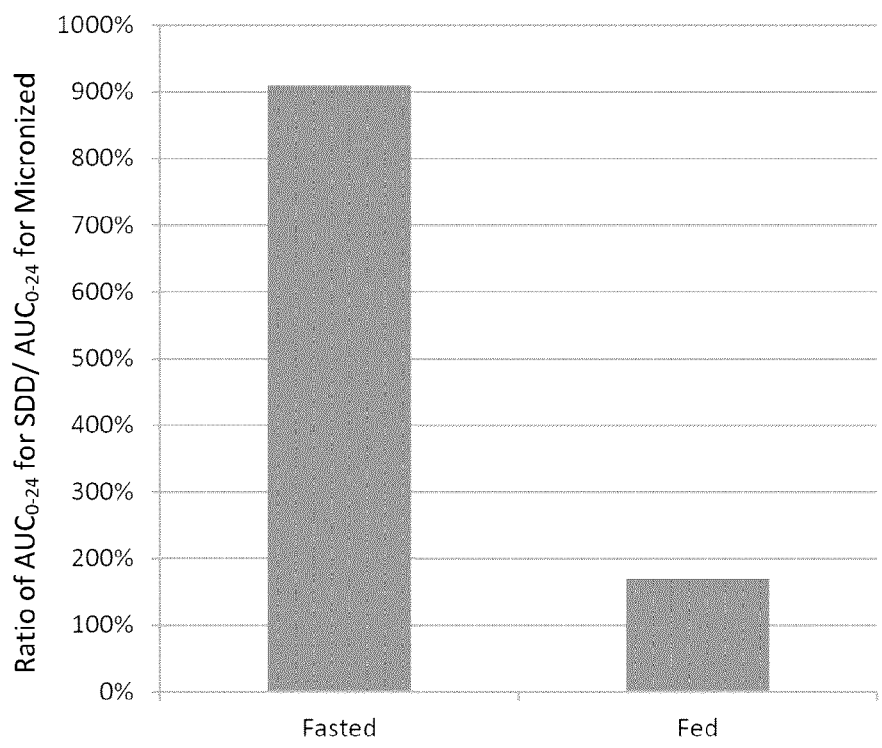

FIGS. 11A-11B show that compound 1 in an SDD formulation (as a free base) has improved PK properties, compared to a micronized formulation (as an HCl salt). As shown in FIG. 11A, the ratio of these values for fasted versus fed subjects was about three-fold higher for the SDD formulation compared to the micronized formulation. Thus, use of the SDD formulation reduced the food effect of compound 1, as compared to the micronized formulation. Furthermore, the SDD formulation provided improved AUC values relative to the micronized formulation. As shown in FIG. 11B, the $AUC_{0-24}$ values for the SDD formulation were more than 900% and 150% greater for fasted and fed states, respectively, than that for the micronized formulation. Additional data comparing SDD and micronized formulations are provided in Table 12. Overall, both $AUC_{0-24}$ and $C_{max}$ for the SDD formulation were increased, and significant improvements were observed in intersubject variability (e.g., improved CV) relative to the micronized formulation.

TABLE 12

| Formulation | $AUC_{0-24}$ (hr*ng/mL)* | | $C_{max}$ (ng/mL)* | | Mean $T_{max}$ (hr)* | |
| --- | --- | --- | --- | --- | --- | --- |
| | Fasted | Fed | Fasted | Fed | Fasted | Fed |
| SDD (free base), 225 mg dose[a] | 2574 (30%) | 3954 (27%) | 553 (30%) | 690 (29%) | 3.0 | 5.0 |
| Micronized (HCl salt), 200 mg dose[b] | 489 (82%) | 2311 (26%) | 65 (94%) | 336 (33%) | 3.0 | 5.0 |
| Micronized (HCl salt), 400 mg dose[c] | 394 (42%) | 2703 (39%) | 51 (56%) | 389 (35%) | 3.0 | 7.0 |

*CV provided in parentheses.
[a]Data for $AUC_{0-24}$, $C_{max}$, and $T_{max}$ for SDD are corrected for the carry-over effect and truncated Period 2 (as in Table 11 above).
[b]Data for $AUC_{0-24}$ and $C_{max}$ from a 200 mg dose were normalized to a 225 mg dose.
[c]Data for $AUC_{0-24}$ and $C_{max}$ from a 400 mg dose were normalized to a 225 mg dose.

Table 13 provides additional data that are corrected for carry-over effect and includes all the data from both periods (i.e., samples from entire Period 1 and Period 2).

TABLE 13*

| Treatment | Period | Subject | $C_{max}$ (ng/mL) | $AUC_{0-24}$ (hr*ng/mL) | $AUC_{0-120}$ (hr*ng/mL) | $AUC_{0-168}$ (hr*ng/mL) | $AUC_{0-\infty}$ (hr*ng/mL) |
| --- | --- | --- | --- | --- | --- | --- | --- |
| Fasted | 1 | 3002 | 916 | 3648 | 4582 | 4864 | 5544 |
| | | 3003 | 431 | 3479 | 4757 | 5159 | 7399 |
| | | 3005 | 806 | 4473 | 5940 | 6226 | 6841 |
| | | 3008 | 423 | 1725 | 2162 | 2279 | 2637 |
| | | 3009 | 530 | 2654 | 3417 | 3599 | 4099 |
| | | 3011 | 372 | 2107 | 2868 | 3014 | 3432 |
| | | 3013 | 556 | 2275 | 3064 | 3237 | 3604 |
| | | 3015 | 425 | 2793 | 3660 | 3813 | 4180 |
| | | Mean | 557 | 2894 | 3806 | 4024 | 4717 |
| | | CV % | 36 | 32 | 32 | 32 | 36 |
| Fasted | 2 | 3001 | 528 | 2186 | 2743 | 2916 | 5019 |
| | | 3004 | 685 | 3233 | 4219 | 4480 | 6296 |
| | | 3006 | 563 | 2046 | 2867 | 3009 | 5161 |
| | | 3007 | 250 | 1876 | 2706 | 2922 | 6210 |
| | | 3010 | 473 | 2617 | 3612 | 3825 | 5854 |
| | | 3012 | 595 | 1808 | 2291 | 2438 | 4287 |
| | | 3014 | 719 | 2107 | 2769 | 2969 | 4110 |
| | | 3016 | 576 | 2159 | 2993 | 3170 | 5254 |
| | | Mean | 549 | 2254 | 3025 | 3216 | 5274 |
| | | CV % | 26 | 21 | 20 | 20 | 16 |
| Fasted | 1 | 3001 | 608 | 3169 | 4091 | 4361 | 5298 |
| | | 3004 | 823 | 4363 | 5935 | 6313 | 7591 |
| | | 3006 | 328 | 2876 | 3538 | 3740 | 4381 |
| | | 3007 | 915 | 3577 | 4968 | 5400 | 8572 |
| | | 3010 | 449 | 3949 | 5473 | 5820 | 6730 |
| | | 3012 | 613 | 2809 | 3562 | 3778 | 4419 |
| | | 3014 | 787 | 4160 | 5154 | 5371 | 5884 |
| | | 3016 | 531 | 3524 | 4710 | 5067 | 6346 |
| | | Mean | 632 | 3553 | 4679 | 4981 | 6153 |
| | | CV % | 32 | 16 | 19 | 19 | 24 |

TABLE 13*-continued

| Treatment | Period | Subject | $C_{max}$ (ng/mL) | $AUC_{0-24}$ (hr*ng/mL) | $AUC_{0-120}$ (hr*ng/mL) | $AUC_{0-168}$ (hr*ng/mL) | $AUC_{0-\infty}$ (hr*ng/mL) |
|---|---|---|---|---|---|---|---|
| Fasted | 2 | 3002 | 649 | 4450 | 5887 | 6278 | 10031 |
| | | 3003 | 519 | 3381 | 4691 | 5239 | 11462 |
| | | 3005 | 1054 | 6737 | 8707 | 9139 | 14742 |
| | | 3008 | 591 | 2947 | 3984 | 4272 | 7282 |
| | | 3009 | 806 | 3857 | 5116 | 5451 | 8667 |
| | | 3011 | 882 | 4716 | 5994 | 6236 | 8157 |
| | | 3013 | 570 | 3102 | 4528 | 4916 | 7244 |
| | | 1515 | 920 | 5605 | 6819 | 7126 | 10551 |
| | | Mean | 749 | 4349 | 5716 | 6082 | 9767 |
| | | CV % | 26 | 30 | 27 | 25 | 26 |

*Values were corrected for the carry-over effect.

Additional studies can be conducted to determine absolute bioavailability of a single dose of compound 1 in a SDD formulation using a microdose of $^{14}C$-labeled compound 1 (free base).

Example 8

Manufacturing Process for Hot Melt Extrusion Formulations

Various hot melt extrusion (HME) formulations were prepared. The preferred polymers were found to be Kollidon® VA 64 (Copovidone), HPMCAS-MF (Hypromellose Acetate Succinate), and Kollidon® K30 (Povidone, PVP). Dissolution properties of these formulations are provided below in Example 9.

Briefly, the following process was developed to prepare an HME formulation with 20% (w/w) compound 1 with HPMCAS-MF. Vitamin E TPGS was pre-milled to reduce particle size down to ≤600 micron, and compound 1 was pre-sieved. Then, a pre-blend was prepared having 20% (w/w) sieved compound 1, 75% (w/w) HPMCAS-MF, and 5% (w/w) milled vitamin E TPGS. The pre-blend was processed using a co-rotating twin screw extruder having the following heating zone set points: 75° C., 110° C., 130° C., 140° C., and 95° C.; and the resultant extrudate was collected and processed further by milling (pelletizing) to reduce its particle size to ≤500 microns. Approximately half of the milled/pelletized extrudate was sieved and blended with half of the microcrystalline cellulose. Then, various pharmaceutically acceptable excipients (i.e., lactose, sodium lauryl sulphate, colloidal silicon dioxide, and croscarmellose sodium) were added and blended. The remaining milled/pelletized extrudate and microcrystalline cellulose were added and blended, where the resultant blend was co-milled and further processed by adding a lubricant (i.e., magnesium stearate). Finally, the blend was used to fill hard gelatin shell capsules.

Each capsule contained 75 mg of compound 1 (free base) in a HPMCAS-MF and Vitamin E TPGS amorphous solid dispersion prepared by hot melt extrusion (HME). The quantitative composition of these HME capsules is shown in Table 14.

TABLE 14

| Component | Function | Standard | Quantity per Capsule (mg) |
|---|---|---|---|
| Compound 1 (free base) | API | C of A | 75.00 |
| Hypromellose acetate succinate Type MF (HPMCAS-MF) | Polymer component of the solid dispersion | Ph. Eur., NF, JP | 281.25 |
| Vitamin E TPGS (d-alpha tocopheryl polyethylene glycol 1000 succinate) | Surfactant | Ph. Eur., NF, JP | 18.75 |
| Lactose monohydrate | Binder-Filler | Ph. Eur., NF, JP | 74.74 |
| Microcrystalline cellulose | Binder-Filler | Ph. Eur., NF, JP | 74.74 |
| Croscarmellose sodium | Disintegrant | Ph. Eur., NF, JP | 17.00 |
| Sodium lauryl sulphate | Wetting agent | Ph. Eur., NF, JP | 4.24 |
| Colloidal silicon dioxide | Flow aid/Glidant | NF | 2.14 |
| Magnesium stearate | Lubricant | Ph. Eur., NF, JP | 2.14 |
| Capsule Shell, hard gelatin white opaque size 00 | Dosage form | | Na |
| | | Total Fill Weight: | 550.0 |

Abbreviations:
API = Active Pharmaceutical Ingredient;
C of A—Certificate of Analysis;
Ph. Eur. = European Pharmacopoeia;
NF = National Formulary;
JP = Japanese Pharmacopeia The formulation development materials were tested for dissolution enhancement and for stability. The 1:4 ratio of API:polymer with a 5% surfactant was confirmed suitable. Solid-state characterization was performed on these formulations, including modulated dynamic scanning calorimetry (mDSC) polarized light microscopy, kinetic solubility, and X-ray powder diffraction (XRRD), each to confirm that the API was dispersed in an amorphous form.

Example 9

Dissolution Studies of Hot Melt Extrusion Formulations

Supersaturation dissolution kinetics provides valuable information regarding the performance of different matrix polymers in combination with an active agent. In particular, such studies could provide insight on which formulations could provide enhanced bioavailability. Accordingly, dissolution studies were conducted on the following three HME formulations: Kollidon® VA 64 (Copovidone), HPMCAS-MF (Hypromellose Acetate Succinate), and Kollidon® K30 (Povidone, PVP).

Briefly, the target concentration of the dissolution sample solution was 1.1 mg/mL, or ten times the estimated sink dissolution sample solution concentration produced by a 100 mg dose when dissolved in 900 mL of dissolution media. Triplicate preparations of about 10 mg of extrudate (2 mg of compound 1 in the three HME formulations) were transferred into separate micro-centrifuge tubes. About 1.8 mL of dissolution media was preheated to 37° C. and added to each tube, where the tube was then placed into an incubator shaker at 37° C. and 250 rpm. Samples were centrifuged at 13,000 rpm for one minute, and 25 µL aliquots of the clear supernatant were transferred into HPLC vials and diluted with 1.0 mL of HPLC mobile phase (30%/70% of pH 6.6 buffer/acetonitrile) at 10' (minutes), 20', 40', 1 hr (hour), 1.5 hrs, 2 hrs, 4 hrs, and 24 hrs. An isocratic HPLC method was applied for quantitation against a five point calibration curve in the range of 5.5-220 µg/mL (C18, 5 µm, 4.6×150 mm column, and UV 216 nm detection). The HPLC sample solution target concentration was 27.1 µg/mL. Table 15 provides these data.

TABLE 15

| Sample | Processing Conditions | $C_{max}$ (µg/mL) | SD | $T_{max}$ | $AUC_{0-4\,hr}$ (mg * hr/mL) |
|---|---|---|---|---|---|
| Control (free base) | na | 2.645 | 2.0 | 2 hours | 0.008 |
| 20% compound 1/ 80% Kollidon ® VA64 (Copovidone) | 150° C., no vacuum | 178.6 | 15.8 | 20 minutes | 0.483 |
| | 150° C., vacuum | 150.5 | 21.1 | 40 minutes | 0.445 |
| | 140° C., no vacuum | 116.5 | 8.1 | 40 minutes | 0.309 |
| 20% compound 1/ Kollidon ® K30 (Povidone) | 150° C., no vacuum | 115.2 | 62.1 | 40 minutes | 0.203 |
| | 150° C., vacuum | 32.8 | 1.2 | 20 minutes | 0.092 |
| | 140° C., no vacuum | 101.0 | 13.5 | 40 minutes | 0.137 |
| 20% compound 1/ 80% HPMCAS-MF | 150° C., no vacuum | 691.8 | 22.5 | 4 hours | 1.68 |
| | 150° C., vacuum | 647.4 | 26.2 | 4 hours | 1.63 |
| | 140° C., no vacuum | 661.6 | 29.0 | 4 hours | 1.66 |

As shown in Table 15, HPMCAS-MF (20% (w/w) compound 1) outperformed the other two polymers (copovidone or PVP) with a $C_{max}$ of 647-692 µg/mL. All the tested formulations provided enhanced $C_{max}$ values, as compared to the Control (free base, compound 1).

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A pharmaceutical composition in unit dosage form for oral administration, said composition comprising from about 20 mg to about 250 mg of substantially amorphous 1-(4-benzhydrylpiperazine-1-yl)-3,3-diphenylpropan-1-one and a pharmaceutically acceptable matrix polymer,
   wherein said pharmaceutical composition comprises a solid dispersion of said 1-(4-benzhydrylpiperazine-1-yl)-3,3-diphenylpropan-1-one and said pharmaceutically acceptable matrix polymer,
   wherein said pharmaceutically acceptable matrix polymer comprises a polymer selected from the group consisting of a cellulose derivative, a polyacrylate, a polyvinyl pyrrolidone, a polyvinyl acetate, and a copolymer of a polyvinyl pyrrolidone and a polyvinyl acetate,
   wherein the weight ratio of said 1-(4-benzhydrylpiperazine-1-yl)-3,3-diphenylpropan-1-one to said pharmaceutically acceptable matrix polymer is from about 1:6 to about 1:1.5.

2. The pharmaceutical composition of claim 1, wherein at least 90% of said 1-(4-benzhydrylpiperazine-1-yl)-3,3-diphenylpropan-1-one is in amorphous form.

3. The pharmaceutical composition of claim 1, wherein the weight ratio of said 1-(4-benzhydrylpiperazine-1-yl)-3,3-diphenylpropan-1-one to said pharmaceutically acceptable matrix polymer is from about 1:4 to about 1:2.

4. The pharmaceutical composition of claim 1, wherein said matrix polymer is said cellulose derivative.

5. The pharmaceutical composition of claim 4, wherein said cellulose derivative is a cellulose acetate having from about 10% to about 50% acetyl.

6. The pharmaceutical composition of claim 5, wherein said cellulose acetate is selected from the group consisting of cellulose acetate phthalate (CAP), methylcellulose acetate phthalate, hydroxypropylmethyl cellulose acetate, and hydroxypropylmethyl cellulose acetate succinate (HPMCAS).

7. The pharmaceutical composition of claim 4, wherein said cellulose derivative is selected from the group consisting of an alkyl cellulose, a hydroxyalkyl cellulose, a hydroxyalkylalkyl cellulose, a hydroxyalkylalkyl cellulose ester, a carboxyalkyl cellulose, a carboxyalkylalkyl cellulose, and a carboxyalkyl cellulose ester.

8. The pharmaceutical composition of claim 1, wherein said matrix polymer is said polyacrylate selected from the group consisting of a polymethacrylate, a methacrylate copolymer, and an ethacrylate copolymer.

9. The pharmaceutical composition of claim 1, wherein said matrix polymer is said polyvinyl acetate selected from the group consisting of a polyvinyl acetate ester and a polyethylene glycol-polyvinylcaprolactam-polyvinylacetate copolymer.

10. The pharmaceutical composition of claim 9, wherein said polyvinyl acetate ester is polyvinylacetate phthalate (PVAP).

11. The pharmaceutical composition of claim 1, wherein said matrix polymer is said copolymer of a polyvinyl pyrrolidone and a polyvinyl acetate and said copolymer has from 10:90 to 70:30 ratio of N-vinyl-2-pyrrolidone to vinyl acetate.

12. The pharmaceutical composition of claim 1, further comprising a plasticizer selected from the group consisting of a polyalkylene oxide, a copolymer of ethylene oxide and propylene oxide, and a polyethoxylated glyceryl ester.

13. The pharmaceutical composition of claim 1, further comprising a surfactant.

14. The pharmaceutical composition of claim 13, wherein said surfactant is selected from the group consisting of a polyethoxylated ester of one or more fatty acids, a polyethoxylated alkyl ether, a polyethoxylated glyceryl ester, a polyoxyethylene glyceryl ester of one or more fatty acids, a sorbitan ester, a polyethoxylated sorbitan ester, a polyethoxylated vitamin analog, and an ethoxylated propoxylated block copolymer.

15. The pharmaceutical composition of claim 14, wherein said polyethoxylated vitamin analog is D-alpha-tocopheryl PEG 1000 succinate.

16. The pharmaceutical composition of claim 1, wherein the solid dispersion is formed by spray drying a liquid mixture comprising said 1-(4-benzhydrylpiperazine-1-yl)-3,3-diphenylpropan-1-one and said pharmaceutically acceptable matrix polymer.

17. The pharmaceutical composition of claim 1, wherein the solid dispersion is formed by hot melt extrusion of a mixture comprising said 1-(4-benzhydrylpiperazine-1-yl)-3,3-diphenylpropan-1-one and said pharmaceutically acceptable matrix polymer.

18. The pharmaceutical composition of claim 1, wherein said unit dosage form comprises from about 20 mg to about 100 mg of 1-(4-benzhydrylpiperazine-1-yl)-3,3-diphenylpropan-1-one.

19. A method to treat pain, said method comprising administering to a subject in need of such treatment an effective amount of the pharmaceutical composition of claim 1.

20. The method of claim 19, wherein said pain is inflammatory pain or neuropathic pain.

21. The method of claim 19, wherein said pain is chronic pain.

22. The method of claim 19, wherein said pain is post-herpetic neuralgia, diabetic neuropathic pain, neuropathic cancer pain, HIV-associated neuropathy, erythromelalgia, failed back-surgery syndrome, trigeminal neuralgia, phantom limb pain, multiple sclerosis related pain, Parkinson disease related pain, post-stroke pain, post-traumatic spinal cord injury pain, lumbosacral radiculopathy, cervical radiculopathy, brachial radiculopathy, pain in dementia, osteoarthritic pain, fibromyalgia syndrome, migraine, cluster headache, tension headache syndrome, facial pain, interstitial cystitis, irritable bowel syndrome, chronic pelvic pain syndrome, lower back pain, neck and shoulder pain, burning mouth syndrome, or complex regional pain syndrome.

23. The method of claim 19, wherein said unit dosage form is administered to achieve a daily amount of up to about 1,600 mg of 1-(4-benzhydrylpiperazine-1-yl)-3,3-diphenylpropan-1-one.

24. The method of claim 23, wherein said daily amount is up to about 400 mg of 1-(4-benzhydrylpiperazine-1-yl)-3,3-diphenylpropan-1-one.

25. A method of preparing a pharmaceutical composition of claim 1, said method comprising:
preparing a mixture or a solution comprising 1-(4-benzhydrylpiperazine-1-yl)-3,3-diphenylpropan-1-one and a pharmaceutically acceptable matrix polymer selected from the group consisting of a cellulose derivative, a polyacrylate, a polyvinyl pyrrolidone, a polyvinyl acetate, and a copolymer of a polyvinyl pyrrolidone and a polyvinyl acetate;
heating said mixture to form a homogenous molten mass;
extruding said molten mass; and
cooling said molten mass to form a solid dispersion.

26. The method of claim 25, wherein said mixture or said solution further comprises a solvent.

27. The method of claim 25, wherein said mixture or said solution further comprises a surfactant.

28. The method of claim 25, wherein said mixture or said solution further comprises a pharmaceutically acceptable excipient.

29. The method of claim 25, wherein said method further comprises filling said unit dosage form with said solid dispersion.

* * * * *